(12) United States Patent
Bukhryakov

(10) Patent No.: US 11,897,827 B1
(45) Date of Patent: Feb. 13, 2024

(54) CARBON ISOTOPE EXCHANGE MEDIATED BY VANADIUM COMPLEXES

(71) Applicant: Konstantin Bukhryakov, Miami, FL (US)

(72) Inventor: Konstantin Bukhryakov, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/199,565

(22) Filed: May 19, 2023

Related U.S. Application Data

(60) Provisional application No. 63/427,173, filed on Nov. 22, 2022.

(51) Int. Cl.
*B01J 31/22* (2006.01)
*C07B 59/00* (2006.01)
*C07F 9/00* (2006.01)

(52) U.S. Cl.
CPC .......... *C07B 59/001* (2013.01); *B01J 31/2282* (2013.01); *C07F 9/00* (2013.01); *B01J 2231/005* (2013.01); *C07B 2200/05* (2013.01)

(58) Field of Classification Search
CPC ........... C07C 5/00; C07C 5/22; C07C 5/2213; C07C 5/23; C07C 5/27; C07C 5/2705; C07B 59/001; B01J 31/2282; C07F 9/00
See application file for complete search history.

(56) References Cited

FOREIGN PATENT DOCUMENTS

| CN | 105126835 A | * 12/2015 |
| JP | 2008020434 A | * 1/2008 |

OTHER PUBLICATIONS

Belov, Dmitry S. et al. "Synthesis and Activity of Vanadium Oxo NHC Alkylidenes. Remarkable Preference for Degenerate Metathesis and Application for Carbon Isotope Exchange." Organometallics 41(21):2897-2902, (Year: 2022).
Belov, Dmitry S. et al. "Ring-Closing Olefin Metathesis Catalyzed by Well-Defined Vanadium Alkylidene Complexes." Chemistry—A European Journal 27(14):4578-4582, (Year:2021).
(Continued)

*Primary Examiner* — Sharon Pregler
(74) *Attorney, Agent, or Firm* — SALIWANCHIK, LLOYD & EISENSCHENK

(57) ABSTRACT

The subject invention provides catalytical compounds/complexes, compositions comprising such compound/complex, synthesis of the compounds/complexes, and methods of using such compounds/complexes as catalysts in, for example, carbon isotope exchange (CIE) on target bioactive molecules. Methods that allow CIE directly on drug candidates are of great importance to chemistry, biology, and medicine. Especially valuable are catalytic procedures that rely on a limited collection of available labeled materials. The instant method comprises converting a methyl group to terminal $=CH_2$ utilizing transfer dehydrogenation catalysts to enable V-based olefin metathesis, followed by a hydrogenation step. The one-pot strategy allows the formal methylation/demethylation sequence and can be applied to an assortment of alkyl-containing compounds.

20 Claims, 48 Drawing Sheets

A. Carbon isotope exchange via olefin metathesis

(56) References Cited

OTHER PUBLICATIONS

Belov, Dmitry S. et al. "Synthesis of Vanadium Oxo Alkylidene Complex and Its Reactivity in Ring-Closing Olefin Metathesis Reactions." Organometallics 40(17): 2939-2944, (Year: 2021).

Tejeda, Gabriela et al. "Vanadium Imido NHC Complexes for Ring-Closing Olefin Metathesis Reactions." Organometallics 41(4): 361-365, (Year: 2022).

* cited by examiner

A. Carbon isotope exchange via olefin metathesis

B. Cross-metathesis

C. Regioselectivity of MCB formation

A. V imido phosphine catalysts:

B. V imido NHC catalysts:

C. Productivity in ring-closing metathesis:

| cat | 1' | 2' | 3' | 4' | 5' | 6' | 7' | 8' | 14 | 10' |
|---|---|---|---|---|---|---|---|---|---|---|
| max TON | 2 | 13 | 6 | 8 | 19 | 15 | 170 | 140 | 59 | 0 |

Mes = 2,4,6-Me$_3$C$_6$H$_2$; Ts = p-CH$_3$C$_6$H$_4$SO$_2$

D. V oxo phosphine catalyst:

14

E. V oxo NHC catalyst:

F. Productivity in cross-metathesis:

A. Alkylidene exchange

B. Cross-metathesis is unfavorable

C. Evidence of degenerate metathesis

A. Cross-metathesis

CARBON ISOTOPE EXCHANGE MEDIATED BY VANADIUM COMPLEXES

CROSS-REFERENCE TO RELATED APPLICATION

This application claims the benefit of U.S. Provisional Application Ser. No. 63/427,173 filed Nov. 22, 2022, which is hereby incorporated by reference herein in its entirety.

BACKGROUND OF THE INVENTION

The incorporation of carbon-14 ($^{14}C$, t½=5730 years) to drug candidates is one of the essential tools for studying drug absorption, distribution, metabolism, and excretion (ADME) and pharmacokinetics properties of novel pharmaceuticals. Recent advances in mass spectrometry and nuclear magnetic resonance facilitated the use of stable carbon isotope $^{13}C$ for similar purposes.

$^{14}C$-labeled compounds are also used to study the environmental fate of pharmaceuticals and to calibrate $^{33}P$-labelled oligonucleotides to assess gene expression. Incorporation of $^{14}C$ to fatty acids, proteins, sugars, and vitamins has been applied for nutrition studies. Short-living $^{11}C$ (t½=20.3 min) has been extensively used for positron emission tomography (PET). It is preferred for studies involving compounds that do not contain fluorine ($^{18}F$, t½=109.8 min.) to avoid any structural modification of target compounds.

Various methods and isotopically labeled reagents have been utilized to introduce labeled carbon atoms to pharmaceuticals. The most practical and desirable methods include late-stage functionalization, preferably in the last step of the synthesis, utilizing readily available reagents containing labeled atoms, such as CO, $CO_2$, KCN, and $CH_3I$.

Carbon isotope exchange (CIE), performed directly on the target molecule, is an ideal method to introduce carbon isotope efficiently. For example, *CO can be utilized in Pd-catalyzed decarbonylation/carbonylation reactions to produce acid chlorides. *$CO_2$ can be utilized to produce carboxylic acids, and Zn(*CN)$_2$ can be used in decyanation/cyanation reactions to obtain nitriles. New CIE transformations using readily available $^{14}C$ and $^{11}C$ sources are highly desirable to complement and significantly expand current approaches limited to carboxylic acid derivatives.

Olefin metathesis (OM) is a vital reaction that utilizes heterogeneous and homogeneous transition metal catalysts. Since its discovery, the OM reaction has found numerous applications in total synthesis, industrial processes, pharmaceutical, and material chemistry. Olefins Conversion Technology (OCT) is one of the most important industrial applications of OM that produces over nine million tons of propylene from ethylene and 2-butenes each year by utilizing silica-supported tungsten oxide ($WO_3/SiO_2$). $WO_3/SiO_2$ has also been employed for the industrial production of 1-hexene and neohexene. Another important process, the Shell Higher Olefin Process (SHOP), produces over a million tons of plasticizers and detergents annually by utilizing $MoO_3/Al_2O_3$ or $Re_2O_7/Al_2O_3$.

Essential well-defined homogeneous catalysts for OM are based on Ru, Mo, and W alkylidene complexes and have been applied in the synthesis of polymers, petrochemicals, agrochemicals, and conversion of low-molecular-weight alkanes to diesel fuel via "alkane metathesis." In addition, some of those catalysts are applied in the eco-friendly conversion of renewable seed oil feedstock into biofuel and linear α-olefins, that are utilized to produce cosmetics, soaps, detergents, polymer additives, and coatings.

Ru, Mo, and W-based homogeneous catalysts are the most prominent due to their high activity and functional group stability. Mo and W oxo species are at the heart of many large-scale processes involving OM, although the precise structure of the active species often remains elusive. In contrast, well-defined W oxo alkylidenes, known for four decades, had limited application in homogenous catalysis due to the higher susceptibility toward bimolecular decomposition than imido complexes.

Tandem alkane dehydrogenation/olefin metathesis can be applied to convert low molecular weight (MW) to high MW alkanes in the C9-C19 range. The process consists of two steps: Ir-based dehydrogenation/hydrogenation and Mo-promoted olefin metathesis (OM). A one-pot sequence utilizing W-based OM catalysts has been applied in reactions with alkyl arenes. However, the currently used OM catalysts are unsuitable for CIE due to the high preference for cross metathesis. Thus, the transition to more abundant first-row metals, such as Vanadium (V), is desirable due to the low cost, decreased environmental footprint, and reduced toxicity. Additionally, first-row metal alkylidenes can offer a unique reactivity, such as C—H bond activation, which has the potential to be coupled with OM.

V is the 20th most abundant element in the Earth's crust. The abundance of V is ~$10^2$ times higher compared to Mo and W and ~$10^5$ times higher than Ru. As a result, it is substantially less expensive than the rare metals that are currently used. Additionally, purification, isolation, and recycling of precious metals consume energy and generate a significant amount of waste. Thus, the use of V-based catalysts will make valuable olefins more accessible to consumers.

V alkylidenes are a promising class of compounds that have shown reactivity in OM, especially in ring-opening metathesis polymerization (ROMP) of cyclic olefins. For example, V imido alkylidenes have been applied for the olefin metathesis involving internal olefins. Thus, there is a need to promote V alkylidene chemistry and develop new highly efficient and selective homogenous well-defined catalysts and reliable V-based CIE.

BRIEF SUMMARY OF THE INVENTION

The subject invention provides catalytical compounds/complexes and/or salts thereof, compositions comprising such compound/complex and/or salts thereof, synthesis of the compounds/complexes, and methods of using such compounds/complexes and/or salts thereof as catalysts in, for example, CIE on target bioactive molecules.

In one embodiment, the subject invention provides a method for exchanging a carbon isotope in a compound comprising a terminal methyl group, the method comprising converting the terminal methyl group of the compound to a terminal $CH_2$ moiety, i.e., $=CH_2$, exchanging the terminal $CH_2$ moiety, i.e., $=CH_2$, to a labeled terminal *$CH_2$ moiety, i.e., $=$*$CH_2$, in the presence of a labeled carbon (*C) source and a V-based catalyst, and optionally, converting the labeled terminal *$CH_2$ moiety, i.e., $=$*$CH_2$, to a labeled terminal methyl group, i.e.,—*$CH_3$, wherein the conversion of terminal —$CH_3$ to $=CH_2$ occurs via a dehydrogenation reaction in the presence of a first catalyst, such as pincer Ir-based transfer hydrogenation catalysts, with or without a hydrogen acceptor (e.g., t-BuCH=$CH_2$ and/or norbornene) or Co-based photocatalytic dehydrogenation system in the presence of photocatalysts (e.g., 2-chloroanthraquinone) and ligands (e.g., dimethylglyoxime); and wherein the conversion of terminal $=$*$CH_2$ to—*$CH_3$ occurs via a hydrogenation reaction in the presence of a hydrogen donor, and a second catalyst, such as pincer Ir-based catalysts or Pd/C, and wherein the first catalyst and the second catalysts may be the same or different.

In one embodiment, the method further comprises reacting the compound comprising the labeled terminal *CH$_2$ moiety, i.e., =*CH$_2$, with a molecule or functional group to form a compound having an internal *C.

In specific embodiments, the *C source is selected from *C labeled methylation reagents and *C labeled terminal olefins, the *C being $^{11}$C, $^{13}$C or $^{14}$C.

In one embodiment, the V-based catalyst has a general structure of formula (I):

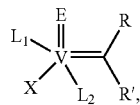
(I)

wherein E is O, NR" or S; L$_1$ and L$_2$ are each independently selected from phosphines, N-heterocyclic carbenes (NHC), pyridines, and nitriles, wherein one of L$_1$ and L$_2$ may be absent; X is selected from halogens, alkoxides, thioalkoxides, sulfonates, NCO, NCS, CN, NO$_3$, and pyrrolides; R and R' are each independently selected from hydrogen, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from hydrogen, alkyl, substituted alkyl, aryl, and substituted aryl; and R" is selected from, for example, hydrogen, alkyl, substituted alkyl, aryl, substituted aryl, heterocycles, and substituted heterocycles.

In one embodiment, the V-based catalyst of the subject invention has a structure of (IV):

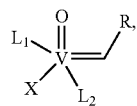
(IV)

Wherein L$_1$ and L$_2$ are each independently selected from, for example, phosphines, NHC, pyridines, ethers, thioethers, and nitriles, wherein one of L$_1$ and L$_2$ may be absent; X is absent or selected from, for example, halogens, alkoxides, thioalkoxides, sulfonates, NCO, NCS, CN, NO$_3$, and pyrrolides; and R is selected from, for example, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from, for example, hydrogen, alkyl, substituted alkyl, aryl, and substituted aryl.

In one embodiment, the V-based catalyst of the subject invention has a structure of (V):

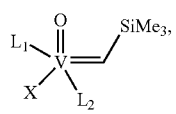
(V)

wherein L$_1$ and L$_2$ are each independently selected from phosphines, NHC, pyridines, ethers, thioethers, and nitriles, wherein one of L$_1$ and L$_2$ may be absent; and X is absent or selected from halogens, alkoxides, thioalkoxides, sulfonates, NCO, NCS, CN, NO$_3$, and pyrrolides.

In one embodiment, L1 and/or L2 are phosphines having a general structure of P(R$_1$)(R$_2$)(R$_3$), where R$_1$, R$_2$, and R$_3$ are each independently selected from, for example, hydrogen, alkyl, substituted alkyl, aryl and substituted aryl. Preferably, L1 and/or L2 are PMe$_3$ or PEt$_3$.

In one embodiment, L1 and/or L2 are NHCs selected from

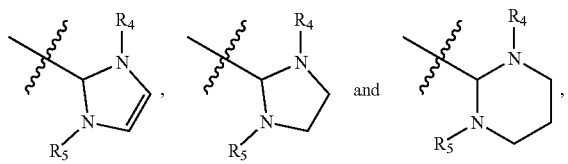

wherein R$_4$ and R$_5$ are independently selected from, for example, hydrogen, alkyl, substituted alkyl, cycloalkyl, substituted cycloalkyl, aryl, and substituted aryl.

In one embodiment, L1 and/or L2 are pyridines having a structure of

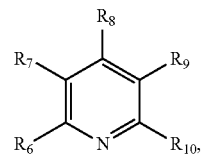

wherein R$_6$, R$_7$, R$_8$, R$_9$, R$_{10}$ are each independently selected from, for example, hydrogen, halogens, alkyl, substituted alkyl, hydorxyl, acyl, and —NH$_2$.

In one embodiment, L1 and/or L2 are nitriles selected from

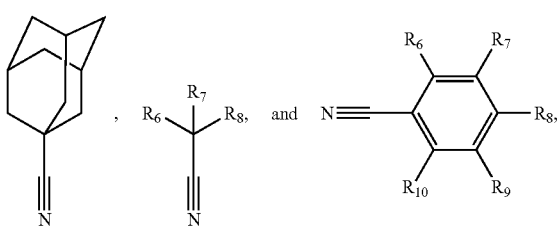

wherein R$_6$, R$_7$, R$_8$, R$_9$, R$_{10}$ are each independently selected from, for example, hydrogen, halogens, alkyl, substituted alkyl, hydorxyl, acyl, and —NH$_2$.

In some embodiments, X is selected from OAd, OPh, substituted OPh, OSiPh$_3$, substituted OSiPh$_3$, F, OBu$^t$F$_6$, NO$_3$, pyrroyl, substituted pyrroyl, SPh, substituted SPh, OC$_6$F$_5$, CN, NCO, NCS, Cl, Br, OTf, and I. Preferably, X is halogen.

In a specific embodiment, the V-based catalyst is (complex 14)

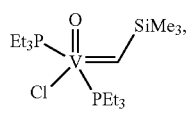

-continued

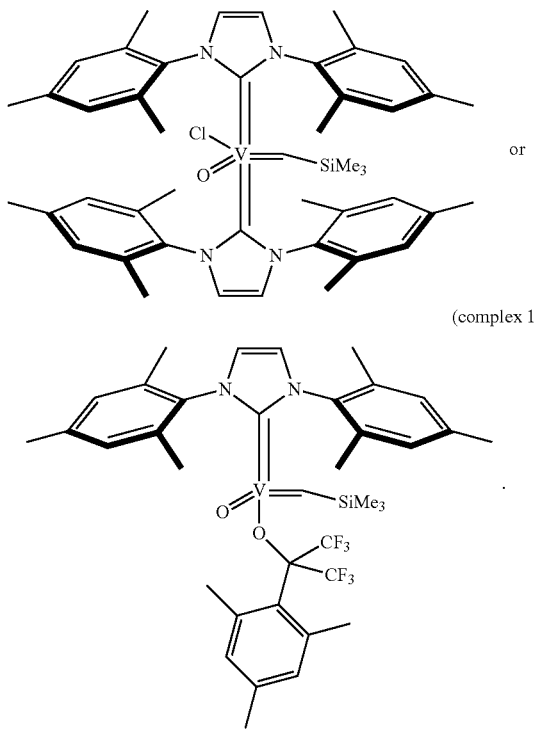

(complex 10')

(complex 11')

In certain embodiments, the V-based catalysts are selected from V imido phosphine catalysts, V imido NHC catalysts, V oxo phosphine catalysts and V oxo NHC catalysts.

In one embodiment, the subject invention provides a method for exchanging a carbon isotope in a compound comprising a terminal methyl group, the method comprising mixing/contacting the compound comprising the terminal methyl group with a first catalyst in the presence or absence of a hydrogen acceptor; adding a V-based catalyst and a labeled carbon source; and optionally, adding a hydrogen donor and a second catalyst, wherein the labeled carbon source is selected from *C labeled methylation reagents and *C labeled terminal olefins, the *C being $^{11}C$, $^{13}C$ or $^{14}C$, and wherein the first catalyst and the second catalysts may be the same or different.

Advantageously, the highly polarized V═C bond enables high regioselectivity in the formation of metallacyclobutane, leading to an efficient transfer of an isotopically labeled ═*CH$_2$ group (*C=$^{11}C$, $^{13}C$, or $^{14}C$) between terminal olefins. Compared to traditional olefin metathesis catalytic systems, where the primary product is the thermodynamically favorable internal olefin, the instant method disfavors cross-products even at elevated temperatures.

DETAILED DESCRIPTION OF THE INVENTION

The subject invention provides catalytical compounds/complexes, and/or salts thereof, compositions comprising such compound/complex and/or salts thereof, synthesis of the compounds/complexes, and methods of using such compounds/complexes and/or salts thereof as catalysts in industrial processes producing commodity and fine chemicals employed in daily life, including plastics, advanced functional materials, household chemicals, agricultural compounds, pharmaceuticals, and many others.

The subject invention provides stable and reactive compounds or complexes for use as reliable catalysts for, for example, olefin metathesis reactions and CIE. In one embodiment, the compound or complex is a Vanadium (V)-based compound or complex, preferably, a V alkylidene, which can offer a unique reactivity compared to second- and third-row counterparts.

Specifically, V alkylidenes promote C—H bond activation, which may be coupled with OM. Also, OM and C—H activation reactions are isolobal, e.g., both reactions involve similar frontier orbitals and related transition states. Advantageously, V-based catalysts of the subject invention can exhibit superior performance compared to currently used catalysts.

In one embodiment, the subject invention provides a method of utilizing V-based catalysts in CIE transformations using, for example, $^{14}$C, $^{13}$C and/or $^{11}$C sources (e.g., via =*CH$_2$ (*C=$^{11}$C, $^{13}$C, or $^{14}$C) group transferring between terminal olefins).

CIE is an emerging area that allows the incorporation of carbon isotopes directly into target compounds for metabolic and pharmacokinetic studies. The integration of carbon-11 into pharmaceuticals is an indispensable tool in positron emission tomography. The innovation of the subject invention is the development of olefin metathesis catalysts based on the first-row transition metal, vanadium, to take advantage of the highly polarized V=C bond. These V alkylidenes enable the regioselective formation of metallacyclobutane, resulting in reversible =CH$_2$ transfer between terminal olefins without the formation of cross-products and ethylene. Therefore, V-catalyzed CIE can serve as a new platform to incorporate labeled carbon atoms into a wide range of pharmaceuticals and natural products without developing new multi-step synthetic strategies.

The subject invention uses, for example, accessible labeled iodomethane (*CH$_3$I) as a carbon isotope source and can be applied to compounds containing various common functional groups. The method can be expanded to alkyl-containing bioactive molecules utilizing a tandem dehydrogenation/olefin metathesis strategy.

Figure 1A:
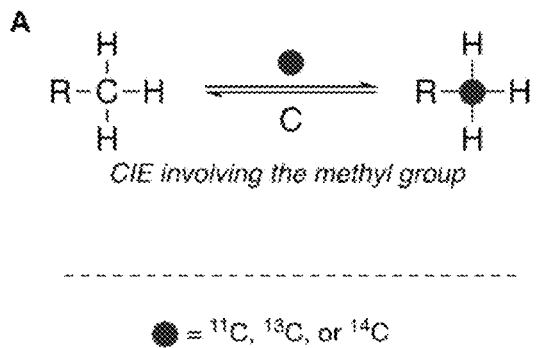
FIG. 1A shows CIE involving a methyl group.
Figure 1B:
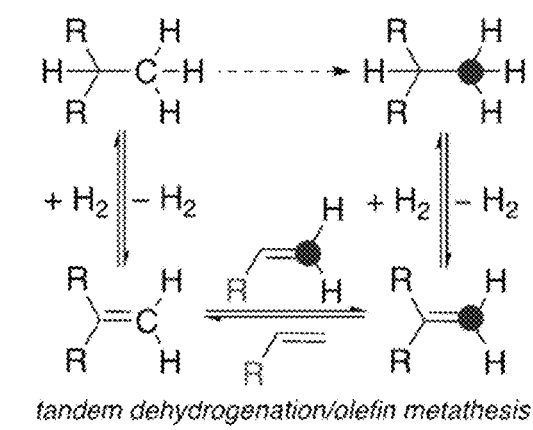
FIG. 1B shows tandem dehydrogenation/olefin metathesis.

A methyl group is incorporated into countless organic molecules and contains only one C—C bond. Thus, a general method of CIE involving the methyl group would be a breakthrough achievement in the synthesis of labeled materials (FIG. 1A). However, despite the success of catalytic C—C bond activation, general and reversible demethylation/methylation remains challenging. Advantageously, the subject invention provides a one-pot tandem dehydrogenation/olefin metathesis strategy (FIG. 1B) to overcome this challenge.

Figure 2A:
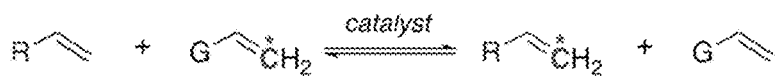
FIG. 2A shows CIE via olefin metathesis.
Figure 2B:
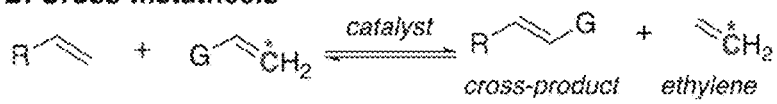
FIG. 2B shows cross-metathesis.

The key step of the instant approach is OM, which allows a reversible and facile C—C double bond breaking and forming sequence that leads to the exchange of an isotopically labeled =*CH$_2$ moiety between two olefins (FIG. 2A). However, classical OM between two terminal olefins often results in the formation of a more thermodynamically favorable cross-product and ethylene (gas) that escapes from the reaction mixture (FIG. 2B). The reverse process, ethenolysis, requires an excess of ethylene, often under high pressure, making it impractical for CIE due to the high cost of $^{13}$C-labeled ethylene (gas) and limited accessibility of $^{14}$C- and $^{11}$C-ethylene.

Figure 2C:
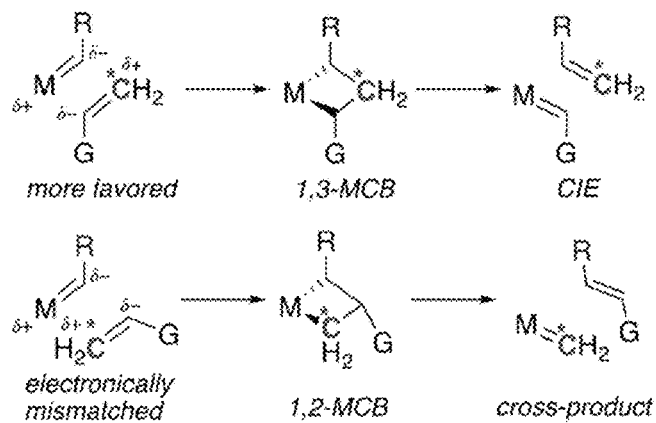
FIG. 2C shows regioselectivity of MCB formation.
Figure 3:
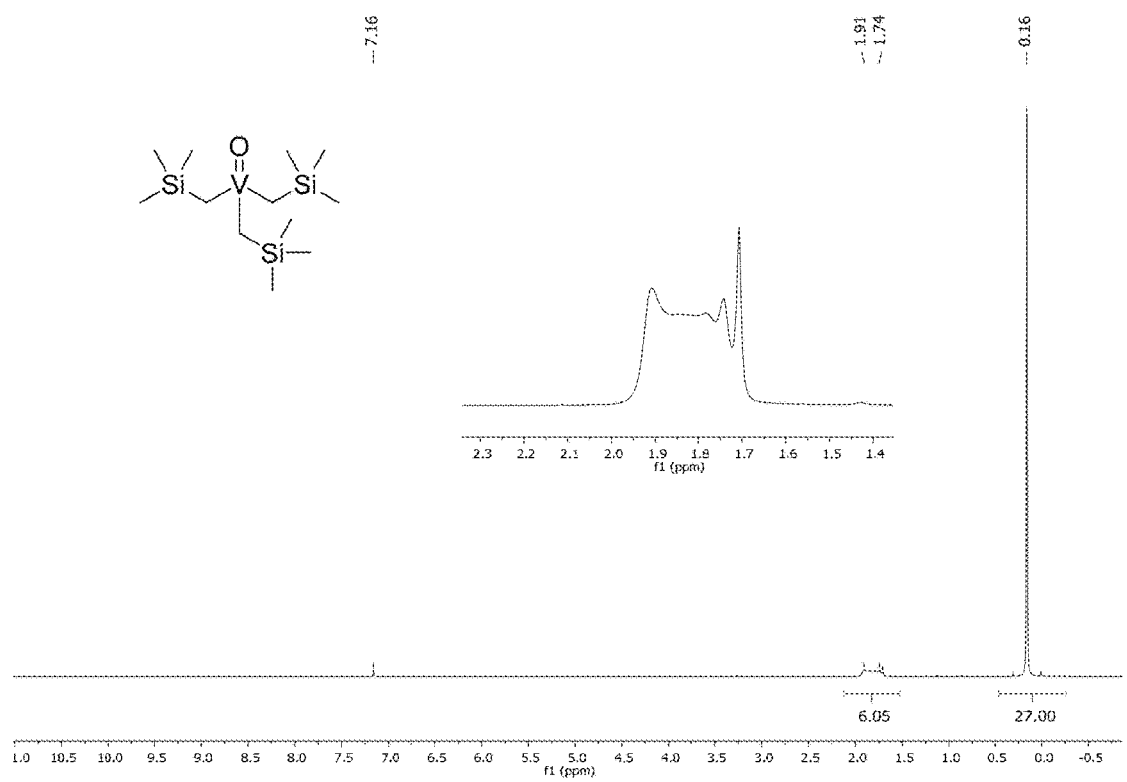
FIG. 3 shows $^1$H NMR spectrum of 12 (C$_6$D$_6$, 400 MHz, 24° C.).
Figure 4:
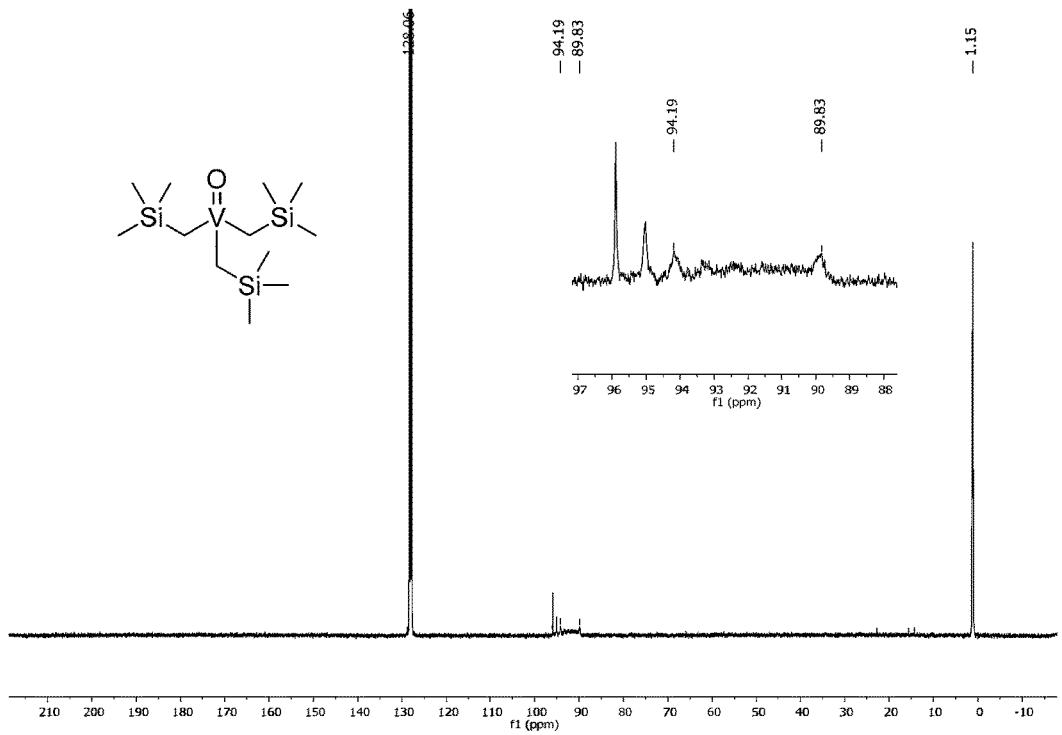
FIG. 4 shows $^{13}$C NMR spectrum of 12 (C$_6$D$_6$, 101 MHz, 24° C.).
Figure 5:
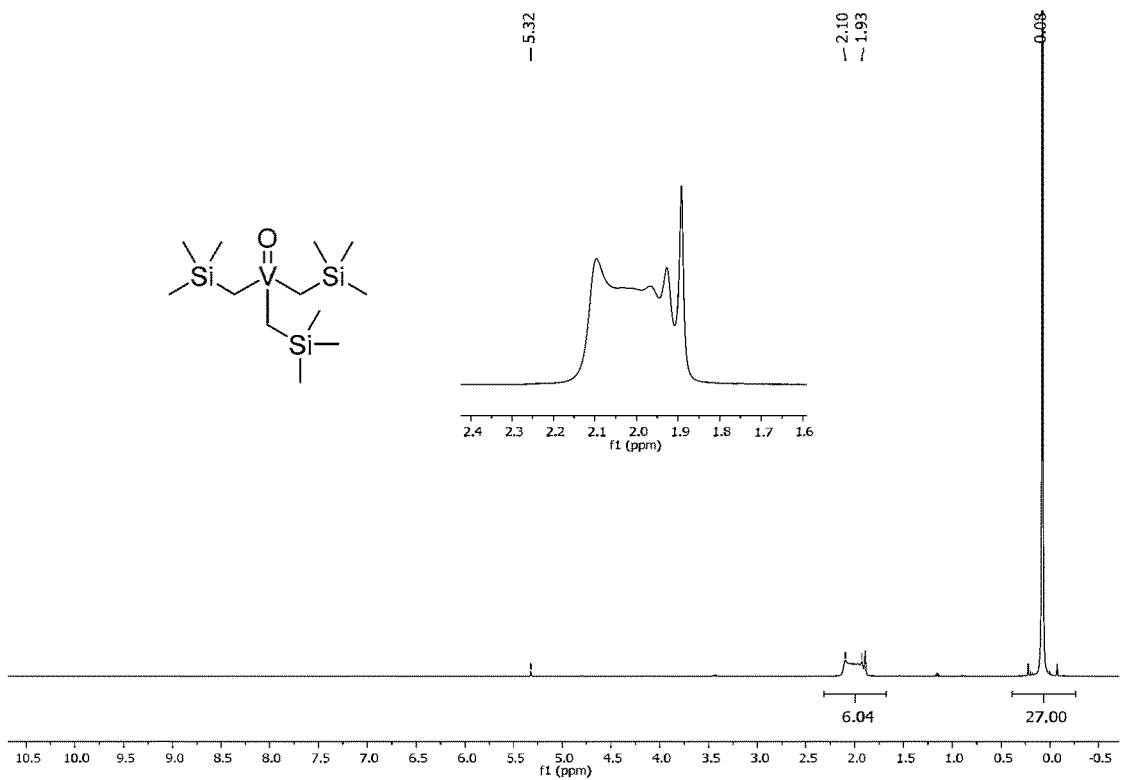
FIG. 5 shows $^1$H NMR spectrum of 12 (CD$_2$Cl$_2$, 400 MHz, 24° C.).
Figure 6:
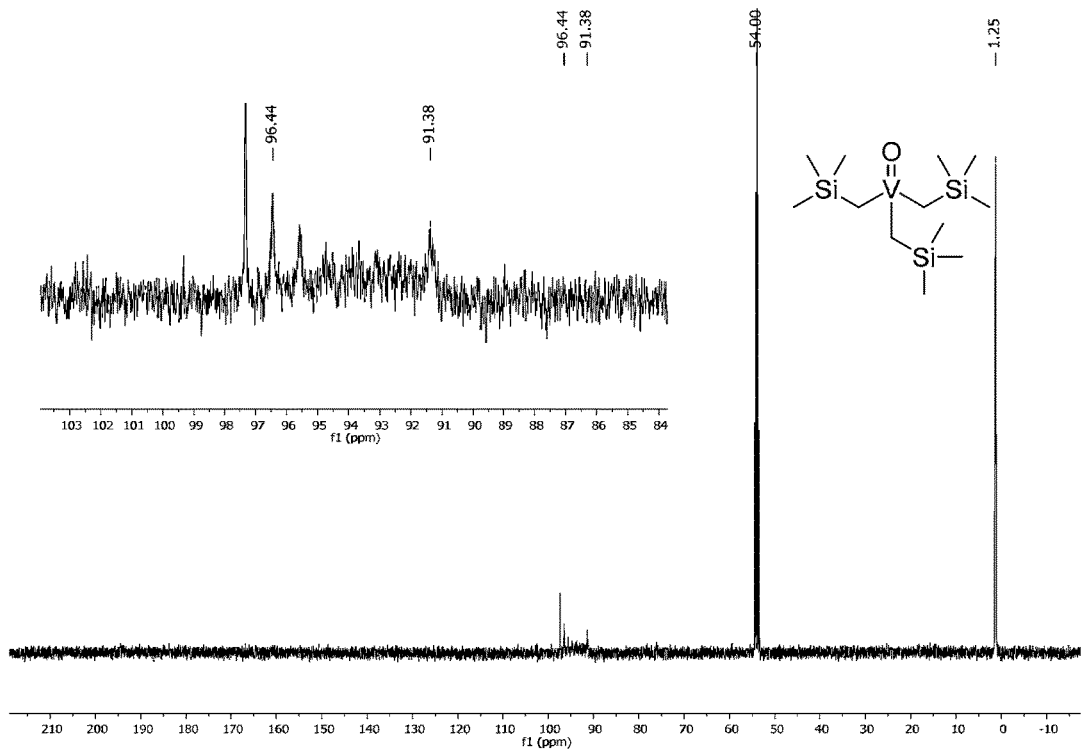
FIG. 6 shows $^{13}$C NMR spectrum of 12 (CD$_2$Cl$_2$, 101 MHz, 24° C.).

The instant method utilizes the more easy-to-handle equimolar amounts of labeled terminal olefins prepared from $^{13}$C-labeled iodomethane (liquid). A cycloaddition step between an alkylidene (complex containing M=C bond) and a terminal olefin can lead to 1,3-metallacyclobutane (MCB, 1,3-MCB) and 1,2-MCB (FIG. 2C). 1,2-MCB results in the formation of cross-product and methylidene that leads to ethylene and must be avoided for CIE reactions. Advantageously, using a first row (3d) transition metal, such as vanadium, which is a more electropositive metal than Ru, Mo, or W, can polarize the M=C bond for the exclusive formation of 1,3-MCB to promote degenerate metathesis and disfavor cross-metathesis.

In one embodiment, the subject invention provides a method for exchanging a carbon isotope in a compound, the method comprising a sequence of reactions including dehydrogenation, olefin metathesis, and/or optionally, hydrogenation, wherein the dehydrogenation reaction occurs in the presence of a first catalyst (e.g., an Ir- or Co-based catalyst), with or without a hydrogen acceptor (such as olefin), and/or a first solvent, the olefin metathesis occurs in the presence of a catalyst, preferably, a V-based catalyst and a labeled carbon source, and the hydrogenation reaction occurs in the presence of a hydrogen donor, a second catalyst (e.g., an Ir-based catalyst or Pd/C) and/or a second solvent.

In one embodiment, the compound subject to CIE comprises a terminal carbon that can be exchanged to a labeled carbon, such as $^{13}C$, $^{14}C$, and $^{11}C$, wherein the terminal carbon is, for example, in a terminal methyl group or a terminal $CH_2$ moiety.

In one embodiment, the subject invention provides a method for exchanging a carbon isotope in a compound comprising a terminal methyl group, the method comprising converting the terminal methyl group of the compound to a terminal $CH_2$ moiety, i.e., $=CH_2$, in the presence of a first catalyst (e.g., an Ir- or Co-based catalyst), with or without a hydrogen acceptor, exchanging the terminal $CH_2$ moiety, i.e., $=CH_2$, to a labeled terminal *$CH_2$ moiety, i.e., $=$*$CH_2$, in the presence of a *C source and a V-based catalyst, and optionally, converting the labeled terminal *$CH_2$ moiety, i.e., $=$*$CH_2$, to a labeled terminal methyl group, i.e.,—*$CH_3$, in the presence of a hydrogen donor and a second catalyst (e.g., an Ir-based catalyst or Pd/C), where the first and second catalysts can be the same or different.

In one embodiment, the method for exchanging a carbon isotope in a compound comprising a terminal methyl group comprises mixing/contacting the compound comprising the terminal methyl group with a catalyst (e.g., an Ir- or Co-based catalyst) in the presence or absence of a hydrogen acceptor; adding a V-based catalyst and a labeled carbon source; and optionally, adding a hydrogen donor and/or a second catalyst (e.g., an Ir-based catalyst or Pd/C) to the mixture.

In one embodiment, the subject invention provides a method for labeling a compound with a *C, the method comprising providing a compound having a terminal methyl group, converting the terminal methyl group of the compound to a terminal $CH_2$ moiety, i.e., $=CH_2$, in the presence of a first catalyst with or without a hydrogen acceptor, exchanging the terminal $CH_2$ moiety, i.e., $=CH_2$, to a labeled terminal *$CH_2$ moiety, i.e., $=$*$CH_2$, in the presence of a *C source and a V-based catalyst, and optionally, converting the labeled terminal *$CH_2$ moiety, i.e., $=$*$CH_2$, to a labeled terminal methyl group, i.e., —*$CH_3$, in the presence of a hydrogen donor, and/or a second catalyst.

In one embodiment, the subject invention provides a method for labeling a compound with a *C, the method comprising mixing/contacting the compound with a catalyst in the presence or absence of a hydrogen acceptor; adding a V-based catalyst and a labeled carbon source; and optionally, adding a hydrogen donor to the mixture. In specific embodiments, the catalyst is selected from pincer Ir-based transfer hydrogenation catalysts, and Co-based photocatalytic dehydrogenation system.

In one embodiment, the subject invention provides a method for exchanging a carbon isotope in a compound comprising a terminal $CH_2$ moiety, i.e., $=CH_2$, the method comprising exchanging the terminal $CH_2$ moiety, i.e., $=CH_2$, to a labeled terminal *$CH_2$ moiety, i.e., $=$*$CH_2$, in the presence of a *C source and a V-based catalyst, and optionally, converting the labeled terminal *$CH_2$ moiety, i.e., $=$*$CH_2$, to a labeled terminal methyl group, i.e., —*$CH_3$, in the presence of a hydrogen donor and/or a catalyst.

In a further embodiment, the step of exchanging the terminal $CH_2$ moiety, i.e., $=CH_2$, to a labeled terminal *$CH_2$ moiety, i.e., $=$*$CH_2$ comprises mixing/contacting the compound comprising the terminal $CH_2$ moiety, i.e., $=CH_2$, with a V-based catalyst and a labeled carbon source.

In one embodiment, the subject invention provides a method for labeling a compound with a *C, the method comprising providing a compound having a terminal $CH_2$ moiety, i.e., $=CH_2$, exchanging the terminal $CH_2$ moiety, i.e., $=CH_2$, to a labeled terminal $CH_2$ moiety, i.e., $=$*$CH_2$, in the presence of a *C source and a V-based catalyst, and optionally, converting the labeled terminal $CH_2$ moiety, i.e., $=$*$CH_2$, to a labeled terminal methyl group, i.e., —*$CH_3$, in the presence of a hydrogen donor, and/or a catalyst.

In some embodiments, the compound comprising the terminal $=$*$CH_2$ can be utilized to react with other molecules or functional groups to form a compound having an internal *C, such as in the form of —*$CH_2$—, or $=$*CH—.

In certain embodiments, the compound can be, for example, a bioactive molecule or drug. In specific embodiments, the hydrogen acceptor is selected from olefins. In a specific embodiment, the hydrogen acceptor is an olefin having a terminal $CH_2$ moiety, for example, t-BuCH=$CH_2$, or norbornene. In some embodiments, the *C source is selected from *C labeled alkylation reagents, e.g., *C labeled methylation reagents, and labeled terminal olefins comprising *C, wherein *C is $^{11}C$, $^{13}C$ or $^{14}C$.

In certain embodiments, the dehydrogenation and/or hydrogenation reaction occurs in the presence of a catalyst, preferably, an Ir-based catalyst, such as $IrH_2$, Pd/C, or Co-based photocatalytic dehydrogenation system in the presence of photocatalysts (e.g., 2-chloroanthraquinone) and ligands (e.g., dimethylglyoxime).

In some embodiments, the hydrogen acceptor is absent. The dehydrogenation reaction leads to the production of $H_2$ escaping from the reaction mixture. In a specific embodiment, the hydrogen doner is $H_2$. In a specific embodiment, the hydrogenation reaction occurs under a hydrogen atmosphere.

In one embodiment, the V-based catalyst is selected from the V complex of the subject invention, the V complex having a general structure of formula (I):

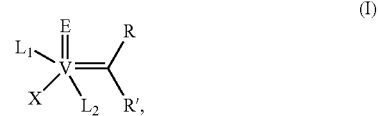

wherein E is NR", O or S; $L_1$ and $L_2$ are neutral ligands, preferably, each independently selected from, for example, phosphines, NHC, pyridines, nitriles, ethers, thioethers, and substituted thereof, wherein one of $L_1$ and $L_2$ may be absent; X is absent or an anionic ligand selected from, for example, halogens, alkoxides, thioalkoxides, sulfonates, NCO, NCS, CN, NO$_3$, and pyrrolides; R and R' are each independently selected from, for example, hydrogen, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from hydrogen, alkyl, substituted alkyl, aryl, and substituted aryl, preferably, R is selected from trialkylSi, OAlkyl, OAryl, perfluorinated alkyl and perfluorinated aryl; and R" is selected from, for example, hydrogen, alkyl, substituted alkyl, aryl, substituted aryl, heterocycles, and substituted heterocycles.

In specific embodiments, $L_1$ and $L_2$ are each independently selected from phosphines, NHC, pyridines, ethers, thioethers and nitriles; X is halogen; and R is selected from alkyl, aryl, heterocycles, trialkylSi, OAlkyl, OAryl, and perfluorinated alkyl. In a preferred embodiment, X is Cl; R is SiMe$_3$ and R' is hydrogen.

In one embodiment, the subject invention provides a compound or complex having a general structure of formula (II):

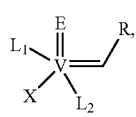

(II)

wherein E is NR", O or S; $L_1$ and $L_2$ are neutral ligands, preferably, each independently selected from, for example, phosphines, NHC, pyridines, nitriles, ethers, thioethers and substituted thereof, wherein one of $L_1$ and $L_2$ may be absent; X is absent or an anionic ligand selected from, for example, halogens, alkoxides, thioalkoxides, sulfonates, NCO, NCS, CN, NO$_3$, and pyrrolides; R is selected from, for example, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from hydrogen, alkyl, substituted alkyl, aryl, and substituted aryl, preferably, R is selected from trialkylSi, OAlkyl, OAryl, perfluorinated alkyl and perfluorinated aryl; and R" is selected from, for example, hydrogen, alkyl, substituted alkyl, aryl, substituted aryl, heterocycles, and substituted heterocycles.

In one embodiment, the subject invention provides V oxo alkylidene complexes having a general structure of formula (III):

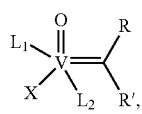

(III)

wherein $L_1$ and $L_2$ are neutral ligands, preferably, each independently selected from, for example, phosphines, NHC, pyridines, nitriles, ethers, thioethers and substituted thereof, wherein one of $L_1$ and $L_2$ may be absent; X is absent or an ionic ligand selected from, for example, halogens, alkoxides, thioalkoxides, sulfonates, NCO, NCS, CN, NO$_3$, and pyrrolides; and R and R' are independently selected from, for example, alkyl, substituted alkyl, aryl, substituted aryl, heterocycles, substituted heterocycles, —OR$^a$, —Si (R$^b$)$_3$ and —NR$^c$R$^d$, wherein R$^a$, R$^b$, R$^c$ and R$^d$ are independently selected from hydrogen, alkyl, substituted alkyl, aryl, and substituted aryl, preferably, R is selected from trialkylSi, OAlkyl, OAryl, perfluorinated alkyl and perfluorinated aryl.

The E group, e.g., the oxo ligand or imido ligand, is necessary to stabilize transition metals in their high oxidation states by extensive π-donation. However, the relatively small oxo ligand can bridge between two metal centers and encourage bimolecular decomposition, which may discourage the development of oxo alkylidenes.

The subject invention provides strategies that can avoid such bimolecular decomposition. The first strategy is introducing disubstituted alkylidene to increase the steric protection around a metal center. Noteworthy, the resulting complexes are of interest from a fundamental standpoint. Thus, disubstituted alkylidenes are essential intermediates in the synthesis of tri- and tetrasubstituted olefins. The second and third approaches are modifications in the size and electronic properties of neutral and anionic ligands. Another essential feature of an oxo ligand is the ability to coordinate Lewis acids, which lowers the oxo ligand's donor ability to the metal, increases electrophilicity of the metal center, and results in higher OM activity.

In one embodiment, the subject invention provides V oxo alkylidene complexes having a general structure of formula (IV):

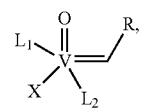

(IV)

wherein $L_1$ and $L_2$ are neutral ligands, preferably, each independently selected from, for example, phosphines, NHC, pyridines, nitriles, ethers, thioethers and substituted thereof, wherein one of $L_1$ and $L_2$ may be absent; X is absent or an ionic ligand selected from, for example, halogens, alkoxides, thioalkoxides, sulfonates, NCO, NCS, CN, NO$_3$, and pyrrolides; and R is selected from, for example, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from hydrogen, alkyl, substituted alkyl, aryl, and substituted aryl, preferably, R is selected from trialkylSi, OAlkyl, OAryl, perfluorinated alkyl and perfluorinated aryl.

In preferred embodiments, $L_1$ and $L_2$ are each independently selected from phosphines, NHC, pyridines, ethers, thioethers and nitriles; X is halogen; and R is selected from alkyl, aryl, heterocycles, trialkylSi, OAlkyl, OAryl, and perfluorinated alkyl. In a preferred embodiment, X is Cl; R is SiMe$_3$ and R' is hydrogen.

In one embodiment, the subject invention provides V oxo alkylidene complexes having a general structure of formula (V):

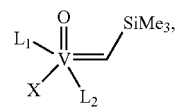

(V)

wherein L₁ and L₂ are neutral ligands, preferrably, each independently selected from, for example, phosphines, NHC, pyridines, nitriles, ethers, thioethers and substituted thereof, wherein one of L₁ and L₂ may be absent; and X is an ionic ligand selected from, for example, halogens, alkoxides, thioalkoxides, sulfonates, NCO, NCS, CN, NO₃, and pyrrolides.

In specific embodiments, L₁ and L₂ are each independently phosphines having a general structure of P(R₁)(R₂)(R₃), where R₁, R₂, and R₃ are each independently selected from hydrogen, alkyl, substituted alkyl, aryl and substituted aryl. In a preferred embodiment, L₁ and/or L₂ are PMe₃ or PEt₃.

In some embodiments, NHCs can be saturated or unsaturated NHCs. In a specific embodiment, the NHC is

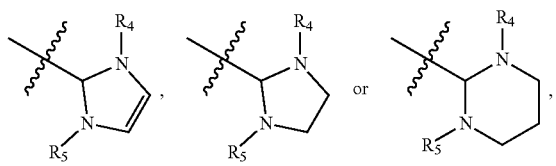

wherein R₄ and R₅ are independently selected from hydrogen, alkyl, substituted alkyl, cycloalkyl, substituted cycloalkyl, aryl, and substituted aryl.

The NHC is a neutral ligand having high σ-donating abilities and controllable steric properties, which can prevent β-H elimination and bimolecular decomposition. Also, NHC complexes may be utilized to prepare air-stable, highly active, selective, and functional group tolerant metal alkylidenes. Saturated NHC ligands are better σ-donors than their unsaturated counterparts, that can affect catalytic activity. Thus, larger NHCs maybe preferred for small oxo V complexes.

In certain embodiments, pyridines have a structure of

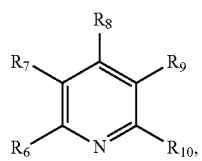

wherein R₆, R₇, R₈, R₉, R₁₀ are each independently selected from, for example, hydrogen, halogens, alkyl, substituted alkyl, hydorxyl, acyl, and —NH₂.

Using a pyridine as a ligand that readily dissociates during the initiation step is an attractive method to prepare active catalysts. The variation of substituents can easily control the binding constant of pyridine derivatives (Py). Also, pyridine is a relatively small ligand. As a result, pyridine-containing alkylidenes can accommodate larger NHC or anionic ligands X than phosphine-containing counterparts.

In certain embodiments, nitriles are selected from, for example,

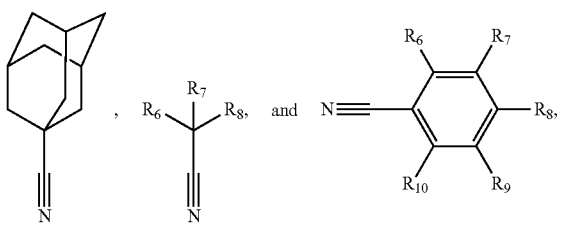

wherein R₆, R₇, R₈, R₉, R₁₀ are each independently selected from hydrogen, halogens, alkyl, substituted alkyl, alkoxides, aryl, substituted aryl, hydorxyl, acyl, and —NH₂.

In specific embodiments, the alkoxide is selected from, for example,

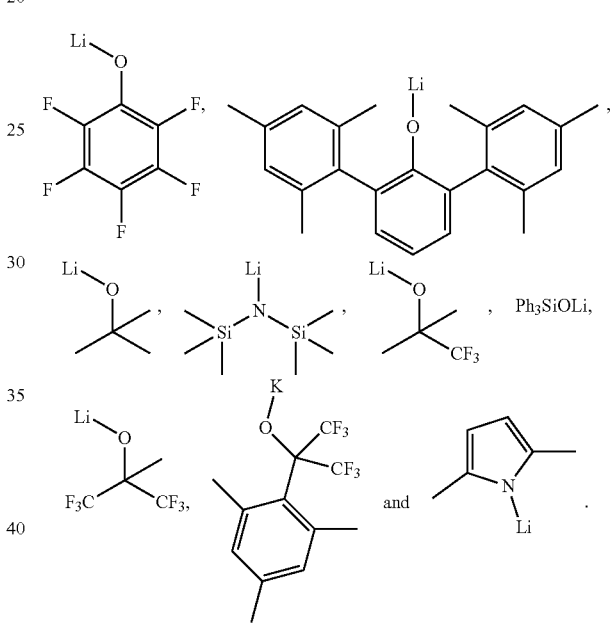

The anionic ligand (X) is an important part of the catalysts that affects their activity, selectivity, and stability. Bulky anionic groups can be introduced for V oxo complexes to limit bimolecular decomposition. The ligand donor parameter (LDP) can be used to compare electronic properties (smaller LDP corresponds to more electron-donating X) and the buried volume parameter (% Vbur, 3.5 Å) can be used to estimate steric properties of anionic ligands (Table 1).

TABLE 1

Electronic and steric properties of anionic ligands.

| ligand | LDP | % $V_{bur}$, 3.5 Å |
| --- | --- | --- |
| OAd | 10.83 | 21.4 |
| OPh | 12.38 | 18.6 |
| OSiPh₃ | 13.28 | 22.2 |
| F | 13.39 | 11.9 |
| OBu$^t_{F6}$ | 13.89 | 23.6 |
| NO₃ | 14.15 | 19.7 |
| pyrrolyl | 14.16 | 20.4 |
| SPh | 14.22 | 21.2 |
| OC₆F₅ | 14.32 | 20.9 |

TABLE 1-continued

Electronic and steric properties of anionic ligands.

| ligand | LDP | % $V_{bur}$, 3.5 Å |
|---|---|---|
| CN | 14.40 | 16.7 |
| NCO | 14.51 | 13.4 |
| NCS | 14.86 | 13.5 |
| Cl | 15.05 | 16.8 |
| Br | 15.45 | 18.1 |
| OTf | 15.75 | 21.6 |
| I | 15.80 | 19.2 |

Electron-withdrawing abilities and atom size increase in the row F<Cl<Br<I. Therefore, the use of Br, I, and electron-withdrawing sulfonates (OTf, OSO$_2$Ar) paired with bulky NHC can be beneficial for V oxo complexes to increase activity and prevent bimolecular decomposition.

In some embodiments, X is selected from OAd, OPh, substituted OPh, OSiPh$_3$, substituted OSiPh$_3$, F, OBu$^f$F$_6$, NO$_3$, pyrroyl, substituted pyrroyl, SPh, substituted SPh, OC$_6$F$_5$, CN, NCO, NCS, Cl, Br, OTf, and I.

In specific embodiments, X is selected from, for example,

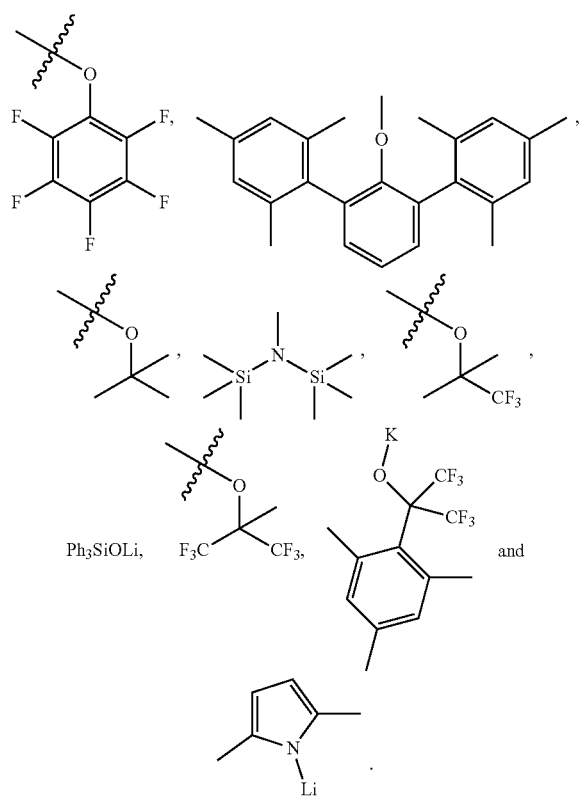

In a specific embodiment, the compound/complex of the subject invention is

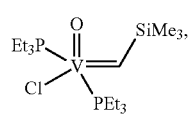

which includes syn/anti isomers. In a further embodiment, the compound/complex of the subject invention is a mixture of syn/anti isomers. The syn and anti isomers in the mixture are at a ratio of at least 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1 or any ratio in between. In a specific embodiment, the syn and anti isomers in the mixture are at a ratio of 97:3.

In a preferred embodiment, the compound/complex of the subject invention is

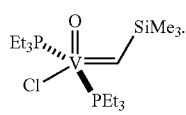

In one embodiment, the subject invention provides V imido alkylidene complexes having a general structure of formula (VI):

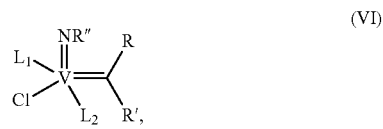

wherein L$_1$ and L$_2$ are neutral ligands, preferably, each independently selected from, for example, phosphines, NHC, pyridines, nitriles, ethers, thioethers and substituted thereof, wherein one of L$_1$ and L$_2$ may be absent; X is absent or an ionic ligand selected from, for example, halogens, alkoxides, thioalkoxides, sulfonates, NCO, NCS, CN, NO$_3$, and pyrrolides; and and R and R' are independently selected from, for example, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from hydrogen, alkyl, substituted alkyl, aryl, and substituted aryl, preferably, R is selected from trialkylSi, OAlkyl, OAryl, perfluorinated alkyl, perfluorinated aryl, and substituted thereof.

In one embodiment, R" is selected from, for example, hydrogen, alkyl, substituted alkyl, aryl, substituted aryl, heterocycles, and substituted heterocycles. In specific embodiments, NR" is selected from, for example,

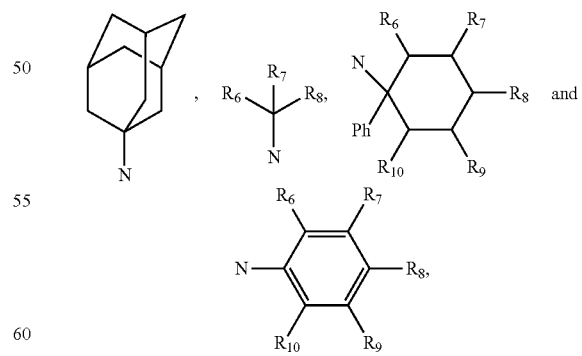

wherein R$_6$, R$_7$, R$_8$, R$_9$, R$_{10}$ are each independently selected from hydrogen, halogens, alkyl, substituted alkyl, alkoxides, aryl, substituted aryl, hydorxyl, acyl, and —NH$_2$, preferably, R$_6$, R$_7$, R$_8$, R$_9$, R$_{10}$ are each independently selected from hydrogen, halogens, OMe, Me, Et, i-Pr, Cy, Ph, and CF$_3$.

In one embodiment, the V-based catalyst is selected from the V complex of the subject invention, the V complex having a general structure of formula (VII):

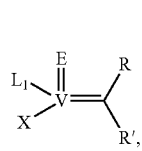
(VII)

wherein E is NR", O or S; $L_1$ is a neutral ligand, preferrably, selected from, for example, phosphines, NHC, pyridines, nitriles, ethers, thioethers, and substituted thereof; X is absent or an anionic ligand selected from, for example, halogens, alkoxides, thioalkoxides, sulfonates, NCO, NCS, CN, $NO_3$, and pyrrolides; R and R' are each independently selected from, for example, hydrogen, alkyl, substituted alkyl, aryl, substituted aryl, heterocycles, substituted heterocycles, $-OR^a$, $-Si(R^b)_3$ and $-NR^cR^d$, wherein $R^a$, $R^b$, $R^c$ and $R^d$ are independently selected from hydrogen, alkyl, substituted alkyl, aryl, and substituted aryl, preferrably, R is selected from trialkylSi, OAlkyl, OAryl, perfluorinated alkyl and perfluorinated aryl; and R" is selected from, for example, hydrogen, alkyl, substituted alkyl, aryl, substituted aryl, heterocycles, and substituted heterocycles.

In specific embodiments, the V based catalysts are selected from V imido phosphine catalysts, V imido NHC catalysts, V oxo phosphine catalysts and V oxo NHC catalysts. In a preferred embodiment, the V imido phosphine catalysts are selected from, for example,

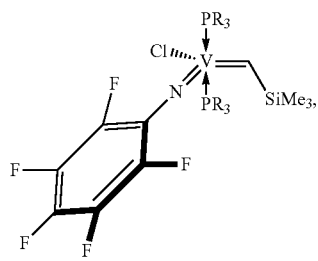

wherein R is alkyl, substituted alkyl, aryl, or substituted aryl;

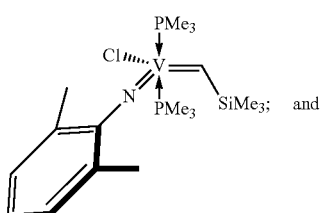
and

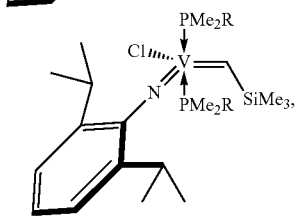

wherein R is alkyl, substituted alkyl, aryl, or substituted aryl.

In a specific embodiment, the V imido phosphine catalyst is

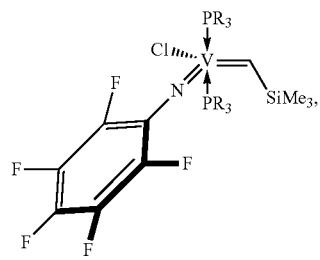

wherein R is methyl or ethyl. In a specific embodiment, the V imido phosphine catalyst is

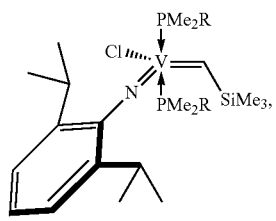

wherein R is methyl or phenyl.

In a preferred embodiment, the V imido NHC catalysts are selected from, for example,

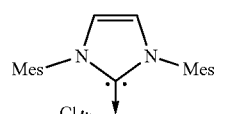

6'

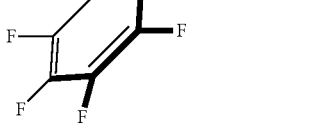

7'

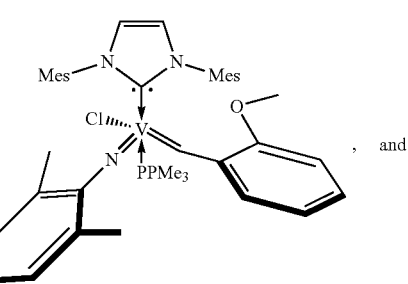
, and

-continued

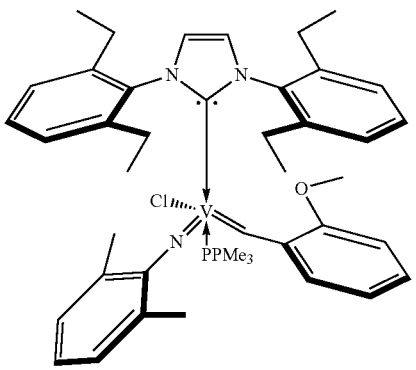

In a specific embodiment, the V oxo phosphine catalyst is complex 14

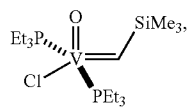

and the V oxo NHC catalyst is complex 10'

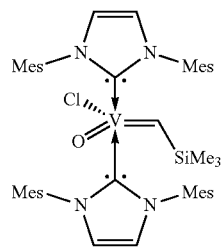

or complex 11'

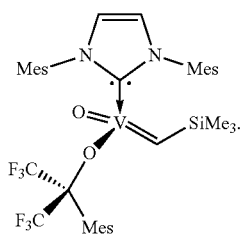

In one embodiment, the subject invention provides a composition comprising the V-based compound or complex of the subject invention.

In one embodiment, the composition further comprises a carrier, diluent, or excipient with which the V-based compound or complex can be formulated or dissolved. The carriers, diluents or excipients may include, for example, aqueous vehicles, non-aqueous vehicles, stabilizers, and solubility enhancers. In a specific embodiment, the carrier, diluent or excipient may be a solvent, e.g., an organic solvent such as toluene, pentane, or ether.

In certain embodiments, the V-based compound or complex of the subject invention is in a solid form or a liquid form when dissolved in a solvent.

In a specific embodiment, the subject invention provides a composition comprising

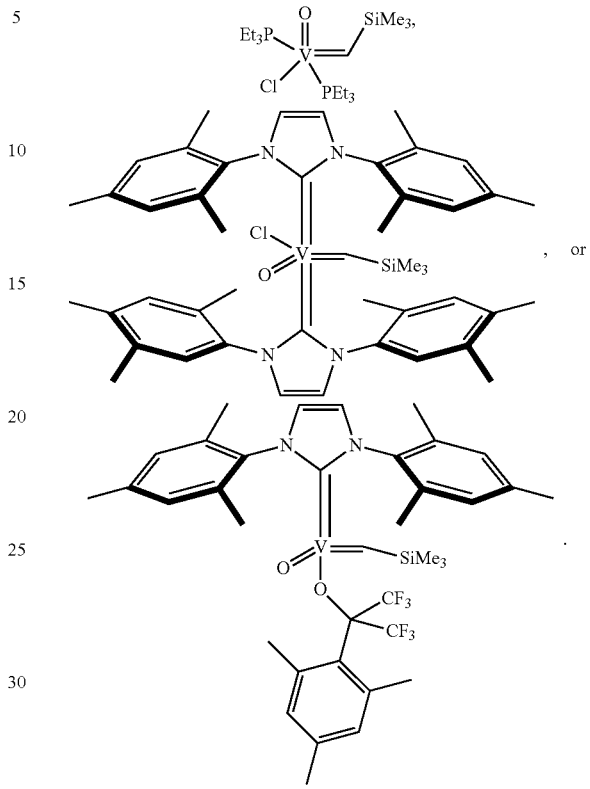

, or

In a specific embodiment, the subject invention provides a composition comprising

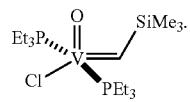

In specific embodiments, the solvent is selected from, for example, CDCl$_3$, CD$_2$Cl$_2$, C$_6$D$_6$, toluene, C$_6$H$_5$F, THF, ether, DME, dichloroethane, and pentane.

In a specific embodiment, X is absent, and the compound/compound is positively charged having the structure of formula (VII):

(VII)

wherein E is NR", O or S; L$_1$ and L$_2$ are neutral ligands, preferably, each independently selected from, for example, phosphines, NHC, pyridines, nitriles, ethers, thioethers, and substituted thereof; R and R' are each independently selected from, for example, hydrogen, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from hydrogen, alkyl, substituted alkyl, aryl, and substituted aryl, preferably, R is selected from trialkylSi, OAlkyl, OAryl, perfluorinated alkyl and perfluorinated aryl; and R" is selected from, for example, hydrogen, alkyl, substituted alkyl, aryl, substituted aryl, heterocycles, and substituted heterocycles.

In one embodiment, the subject invention provides a method for synthesizing the compounds or complex of the subject invention. The method provides strategies to rationally address the stability and reactivity of V alkylidenes to develop reliable catalysts for olefin metathesis reactions.

One approach to increase asymmetry is to exchange one anionic ligand to a weakly-coordinating anion in the presence of a neutral ligand or remove the anionic ligand to form a cationic alkylidene complex. In contrast, alkylidene complexes based on d0 M(V) transition metals (group 5 elements: V, Nb, Ta) containing oxo ligand, anionic ligand, and neutral ligand have the required asymmetry naturally.

In one embodiment, the subject invention provides a method to access a new class of V catalysts for olefin metathesis. The method comprises the oxidization of a V(III) compound to a V(V) oxo compound by an oxidizing agent such as styrene oxide, propylene oxide and trimethylamine oxide, the protonation of the V(V) oxo compound with one or more neutral ligands in the presence of an acid, or with one or more neutral ligands in a salt form, the alpha-hydrogen abstraction induced by the coordination of the one or more neutral ligands, and the exchange for an anionic ligand to form the V oxo alkylidene.

In a specific embodiment, the V(III) compound is a trialkylvanadium and the V(V) oxo compound is trialkyloxovanadium.

In one embodiment, the method for synthesizing the V catalyst of the subject invention comprises: mixing a trialkylvanadium with an oxidizing agent to form a trialkyloxovanadium; adding one or more neutral ligands and an acid, or adding a salt of the one or more neutral ligands; and adding a compound to provide an anionic ligand.

In one embodiment, the method for synthesizing the V catalyst of the subject invention comprises: mixing a trialkylvanadium with an oxidizing agent to form a trialkyloxovanadium; adding a mixture of one or more neutral ligands and an acid; adding one or more neutral ligands in a solvent; and adding a compound to provide an anionic ligand.

In a specific embodiment, the trialkylvanadium is $V(CH_2SiMe_3)_3$. The trialkyloxovanadium is $VO(CH_2SiMe_3)_3$. The oxidizing agent is styrene oxide, propylene oxide or trimethylamine oxide. The one or more neutral ligands are selected from, for example, phosphines, NHC, pyridines, ethers, thioethers and nitriles. The acid is trifluoromethanesulfonic acid, triethylphosphonium triflate or HCl. The anionic ligand donor is $BnNEt_3Cl$.

In a preferred embodiment, the neutral ligand is triethylphosphine.

In one embodiment, the method for synthesizing the V catalyst of the subject invention comprises: providing a trialkyloxovanadium; adding one or more neutral ligands and triethylphosphonium triflate, or adding a salt of the one or more neutral ligands; and adding a compound to provide an anionic ligand.

In one embodiment, the method for synthesizing the V catalyst of the subject invention comprises: providing a trialkyloxovanadium; adding a mixture of one or more neutral ligands and triethylphosphonium triflate, or adding a salt of the one or more neutral ligands; adding one or more neutral ligands in a solvent; and adding a compound to provide an anionic ligand.

In one embodiment, the method for synthesizing the V catalyst of the subject invention comprises 1) mixing $VO(CH_2SiMe_3)_3$ with one or more neutral ligands, e.g., $L_1$ and $L_2$, in the presence of an acid to form a V oxo compound comprising an anion from the acid, wherein the step 1) further occurs in the presence of a solvent, and the acid is triflic acid, or triethylphosphonium triflate; 2) adding a donor of an anionic ligand, which leads to the exchange of the anion, e.g., triflate anion, with the anionic ligand (e.g., chloride ligand), preferably, the donor of the anionic ligand being any quaternary ammonium salt chlarides, more preferrably, the donor of the anionic ligand being $BnNEt_3Cl$.

In one embodiment, the method for synthesizing the compound of the subject invention comprises the protonation of $VO(CH_2SiMe_3)_3$ by $PEt_3$*TfOH in dichloromethane, the alpha-hydrogen abstraction induced by the coordination of $PEt_3$, and the exchange of the triflate anion for chloride in the presence of $BnNEt_3Cl$ to form $VO(CHSiMe_3)(PEt_3)_2Cl$. The resulting complex is catalytically active and could be modified further for specific applications.

In a specific embodiment, the method for synthesizing a V catalyst comprising mixing $VO(CH_2SiMe_3)_3$ with $PEt_3$*TfOH; and adding $BnNEt_3Cl$.

In a specific embodiment, the method for synthesizing a V catalyst comprising mixing $VO(CH_2SiMe_3)_3$ with $PEt_3$*TfOH; adding $PEt_3$ and $CH_2Cl_2$; and adding $BnNEt_3Cl$.

In one embodiment, the subject invention provides a method for synthesizing a cationic V-based compound/complex, the method comprising providing a V-based compound/complex of the subject invention; and adding BArF salts.

In specific embodiments, the solvent is selected from, for example, $CDCl_3$, $CD_2Cl_2$, $C_6D_6$, toluene, $C_6H_5F$, THF, ether, DME, and pentane.

In one embodiment, the compound/complex of the subject invention is used at a concentration of, for example, about 0.1 mol % to about 25 mol %, about 0.2 mol % to about 25 mol %, about 0.5 mol % to about 25 mol %, about 0.5 mol % to about 20 mol %, about 0.5 mol % to about 15 mol %, about 1 mol % to about 20 mol %, about 1 mol % to about 15 mol %, about 1 mol % to about 10 mol %, about 2 mol % to about 15 mol %, about 2 mol % to about 10 mol %, about 2 mol % to about 8 mol %, or about 1 mol % to about 5 mol %.

In certain embodiments, the V alkylidenes of the subject invention may be used for 1) the synthesis of advanced materials, e.g., functional conjugated polymers; 2) the conversion of renewable oil feedstock (e.g., fatty acid esters) to the valuable olefins; 3) the conversion of low-molecular-weight alkanes to diesel fuel; or 4) the development of heterogeneous catalysts for industrial applications.

In one embodiment, V alkylidenes of the subject invention may be used to the C—H activation of alkanes to develop unique tandem C—H activation/olefin metathesis transformations and to activate electron-deficient olefins containing perfluoroalkyl groups.

In one embodiment, the catalysts of the subject invention may be applied in the eco-friendly conversion of renewable seed oil feedstock into biofuel and linear αα-olefins, that are utilized to produce cosmetics, soaps, detergents, polymer additives, and coatings.

Acyclic diene metathesis (ADMET) allows the synthesis of advanced materials, such as electroactive, conjugated, liquid-crystalline, telechelic, hyperbranched, and biorenewable polymers that have found numerous applications. The reverse process, the depolymerization of unsaturated polymers in the presence of olefins, is an attractive method to convert polymers to valuable olefins or other polymers. The catalysts of the subject invention may be used to synthesize conjugated polymers that find use in the fabrication of optoelectronic and electrochemical devices.

In one embodiment, the subject invention provides methods of use of the V-based compounds/complexes of the subject invention for ring-opening metathesis polymerization (ROMP) and cross-metathesis.

In one embodiment, the subject invention provides a method for ring-opening metathesis polymerization of cycloalkenes, the method comprising mixing the cycloalkenes with the V-based catalyst of the subject invention.

In one embodiment, the subject invention provides a method for synthesizing conjugated polymers, the method comprising mixing the monomer of alkenes with the V-based catalyst of the subject invention.

In one embodiment, the subject invention provides a kit comprising the V-based compound or complex of the subject invention. The kit may further comprise a solvent, a container, and an instruction for use the V-based compound or complex.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting of" or "consists essentially of" indicate that the claim encompasses embodiments containing the specified materials or steps and those that do not materially affect the basic and novel characteristic(s) of the claim. Use of the term "comprising" contemplates other embodiments that "consist of" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

General Experimental Details

All air- and moisture-sensitive materials were manipulated in a nitrogen-filled MBraun glovebox or on a dual-manifold Schlenk line. All glassware was dried in an oven prior to use (160° C.). Tetrahydrofuran (THF), diethyl ether, $iPr_2O$, pentane, and toluene were distilled from Na/benzophenone under nitrogen and stored under 3 Å molecular sieves in the glovebox. $CH_2Cl_2$ was distilled over $CaH_2$ under nitrogen and stored under 3 Å molecular sieves in the glovebox. $CDCl_3$, $CD_2Cl_2$, $C_6D_6$ and tol-$d_8$ were dried over 3 Å molecular sieves in the glovebox. $^1H$ NMR spectra were obtained on Bruker 400 MHz spectrometers, and $^{13}C$ NMR spectra were obtained on 101 MHz machines. Chemical shifts for $^1H$ and $^{13}C$ spectra are reported as parts per million and referenced to the residual $^1H$ or $^{13}C$ resonances of the deuterated solvent ($^1H$ δ: $C_6D_6$ 7.16, $CDCl_3$ 7.26; $CD_2Cl_2$ 5.32, DMSO 39.52 $^{13}C$ δ: $C_6D_6$ 128.06, $CDCl_3$ 77.16, $CD_2Cl_2$ 54.00, DMSO 39.52). All NMR data is reported as follows: chemical shift, multiplicity (s=singlet, d=doublet, t=triplet, q=quartet, br=broad, m=multiplet), and coupling constants (Hz), integration. Ultra-High Resolution MS analysis was conducted on a Bruker Solarix FT-ICR-MS instrument operated under positive (+) ion mode equipped with an ESI source. Spectra were internally calibrated utilizing Agilent ESI-L with 3 calibration points, allowing a mass error of <1 ppm with standard deviation of 0.057 ppm.

Starting Materials

Reagents were purchased at the highest commercial quality and used without further purification unless otherwise stated. Vanadium (III) chloride (97%), Styrene oxide (97+%), Hydrogen chloride (1N solution in diethyl ether) was purchased from Acros Organics; (trimethylsilyl)methymagnesium chloride (1M solution in diethyl ether), diallylamine (>98.0%), 4-methoxynenzenesulfonyl chloride (>98%), trifluoromethanesulfonic acid (>98%) were purchased from TCI America; and p-toluenesulfonyl chloride, dansyl chloride (96%), sodium hydride were purchased from Alfa Aesar. 4-Dimethylaminopyridine was purchased from Oakwood chemicals. Triethylphosphine were purchased from Strem Chemical Inc. 3,5-dimethylisoxazole-4-sulfonyl chloride (98%), 8-quinolinsulfonyl chloride (98%) were purchased Combi-Blocks. Triethylamine was purchased from Fisher chemical. Thiophene-2-sulfonyl chloride (96%) was purchased from Matrix Scientific.

Experimental Details $((CH_3)_3SiCH_2)_3VO$ (12).

$VCl_3$ (1.00 g 6.36 mmol) was suspended in THF (64 mL) and reaction mixture was stirred at 60° C. for ~24 h to get a pink solution. The flask was transferred to a freezer (−35° C.) for several hours (during this time most of $VCl_3(THF)_3$ (8) precipitated from solution). The flask was transferred from a freezer and $TMSCH_2MgCl$ (3; 1 M solution in ether, 19.7 mL, 19.7 mmol, 3.1 equiv) was added in the course of ~1-2 min to a vigorously stirred suspension (during the addition pink color changes to dark violet). The reaction mixture was stirred for 5 minutes at room temperature (to ensure dissolution of all material) and transferred to a freezer (−35° C.) for several hours (or overnight). The solvent was evaporated, and the residue was extracted with ether (3×50 mL) and filtered from inorganic material. Ether was evaporated to give (TMSCH$_2$)$_3$V*THF as a violet solid.

(TMSCH$_2$)$_3$V*THF was dissolved in toluene (200 mL, high dilution is important, attempts to increase concentration results in decreased yield) and styrene oxide (2.19 mL, 19.1 mmol, 3.0 equiv.) was added in a single portion (after addition quick change of color to green followed by slow change of color to yellow). The solution was heated to reflux for a short period of time (~1 min) cooled to room temperature and left overnight. Toluene was evaporated (warming to 40-50° C. is acceptable to increase the rate of evaporation). Pentane (100 mL) was added to the residue and the mixture was thoroughly stirred with spatula. White precipitate (polymer from styrene oxide) was filtered and washed with additional amount of pentane (2×50 mL). Pentane was evaporated and the residue was dissolved in a hot ether (12-15 mL), solution was filtered through syringe filter to a vial and transferred to a freezer (−35° C.). (TMSCH$_2$)$_3$VO (VO(CH$_2$SiMe$_3$)$_3$) (12) was precipitated as bright yellow needles. The precipitate was filtered off and washed with cold (−35° C.) ether (2×5 mL) and dried in vacuum. Additional product can be recovered by concentration of filtrate to ⅓ to ⅕ of a volume. M=1.057 g (51%).

The product is very light sensitive (80% decomposition was observed after 72 hours at RT in transparent vial). Compound was stored in a glovebox freezer (−35° C.) in a vial wrapped in aluminum foil. Surprisingly, the yield was not affected when the reaction mixture was protected from light.

TMSCH$_2$Li (2) can be used in the reaction instead of TMSCH$_2$MgCl (3), but the yield was reduced by ~15%. It is possible that LiCl cannot be completely separated from reaction mixture, and it interferes with the oxidation step.

The NMR spectra of 12 are shown in FIGS. 3-6.
$^1$H NMR: (C$_6$D$_6$, 400 MHz) δ=0.16 (s, 27H), 1.74-1.91 (br., 6H).
$^{13}$C NMR: (C$_6$D$_6$, 100 MHz) δ=1.2, 89.8-94.2 (br.).
$^1$H NMR: (CD$_2$Cl$_2$, 400 MHz) δ=0.08 (s, 27H), 1.93-2.10 (br., 6H).
$^{13}$C NMR: (CD$_2$Cl$_2$, 100 MHz) δ=1.3, 91.4-96.4 (br.).
ClVO(PEt$_3$)$_2$CHSi(CH$_3$)$_3$ (14)

Figure 7:
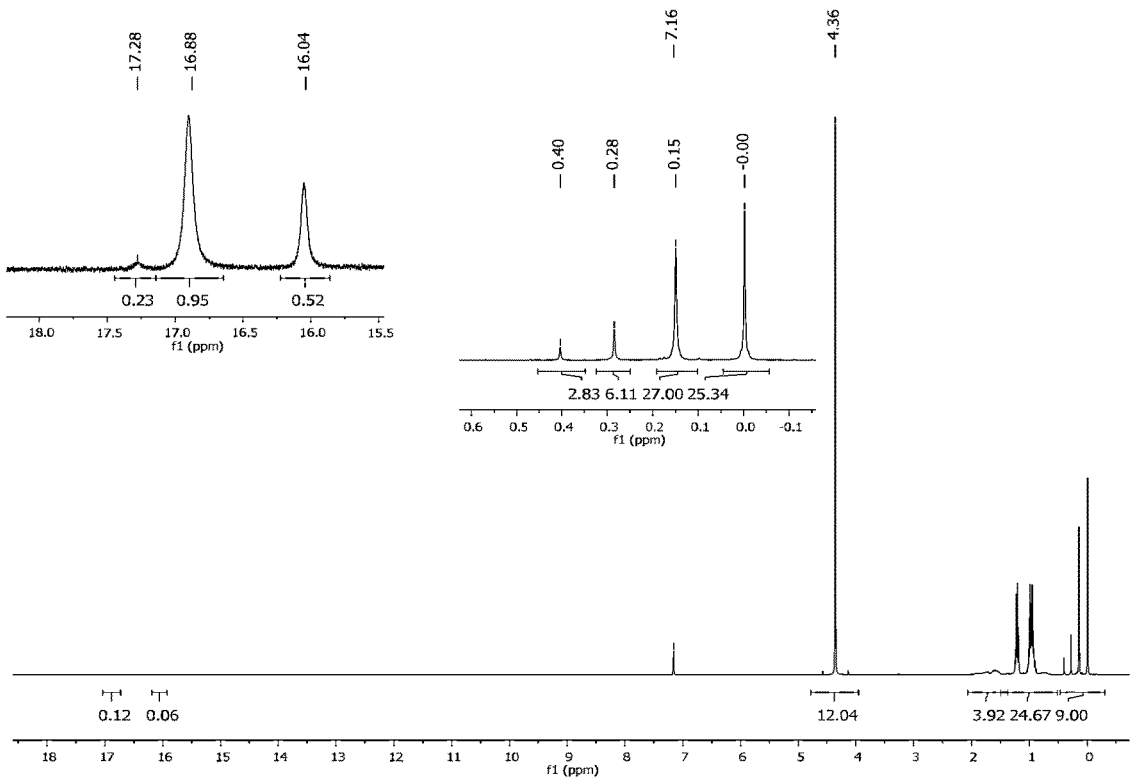
FIG. 7 shows the characteristic signals in $^1$H NMR spectrum used to monitor the progress conversion of 12 to 13+14 (C$_6$D$_6$, 400 MHz, 24° C.).

(TMSCH$_2$)$_3$VO (12; 753 mg, 2.29 mmol) was placed in a 20 mL vial with a stirring bar. Cold solid Et$_3$P*TfOH (738 mg, 2.75 mmol, 1.2 equiv) was added followed by Et$_3$P (1.69 mL, 11.46 mmol, 5 equiv) and CH$_2$Cl$_2$ (3.0 mL). The vial was protected from light using aluminum foil and stirred for ~6 days at room temperature. The progress of the reaction was occasionally checked by $^1$H NMR (sample ~50 µL of reaction mixture was dissolved in 1 mL of C$_6$D$_6$) (FIG. 7). Characteristic chemical shifts of TMS groups: starting material 0.15 ppm, (CH$_3$)$_4$Si 0.00 ppm, TfO-V ═CHTMS 0.28 ppm, Cl—V ═CHTMS 0.40 ppm (FIG. 7).

When the reaction is complete BnNEt$_3$Cl (522 mg, 2.29 mmol) was added, and reaction mixture was stirred for 30 min. Solvent was evaporated and residue was extracted with pentane (3×20 mL) and filtered. Filtrate was evaporated and dissolved in iPr$_2$O (~1 mL), insoluble material was filtered through syringe filter. Filtrate was transferred to a freezer (−35° C.). After overnight the product crystallized as big yellow crystals. The solvent was removed using syringe and crystals were quickly washed with very small (~0.5 mL) amount of cold (−35° C.) iPr$_2$O and dried in vacuum. M=464 mg (48%).

Occasionally a small amount of dark green crystal of impurity Cl$_2$VO(PEt$_3$)$_2$ was observed (CCDC2093139). The crystals of impurity were separated manually.

Figure 8:
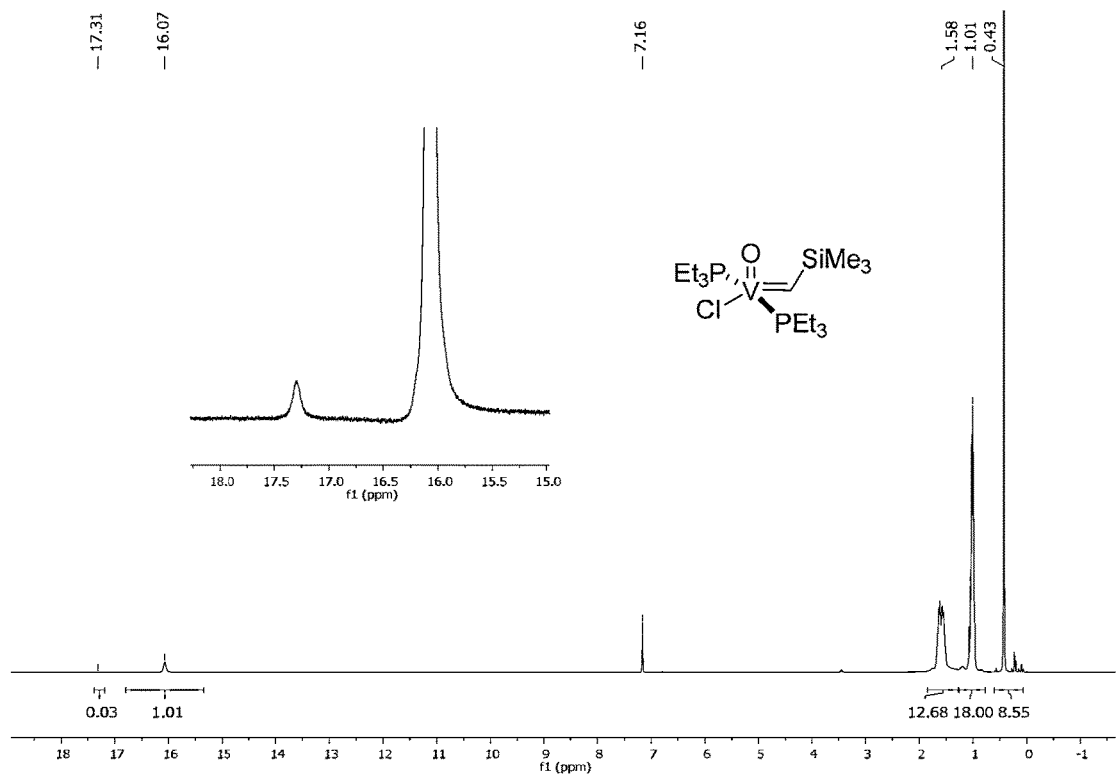
FIG. 8 shows $^1$H NMR spectrum of 14 (C$_6$D$_6$, 400 MHz, 24° C.).
Figure 9:
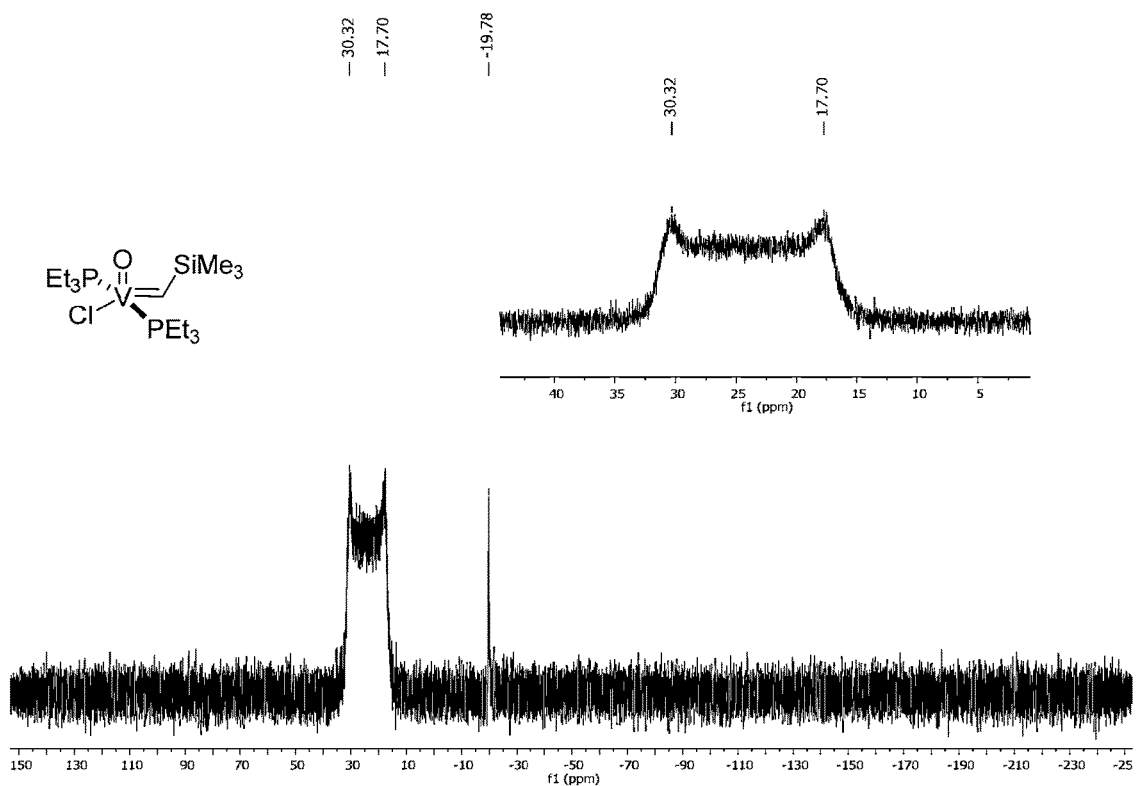
FIG. 9 shows $^{31}$P NMR spectrum of 14 (C$_6$D$_6$, 162 MHz, 24° C.).
Figure 10:
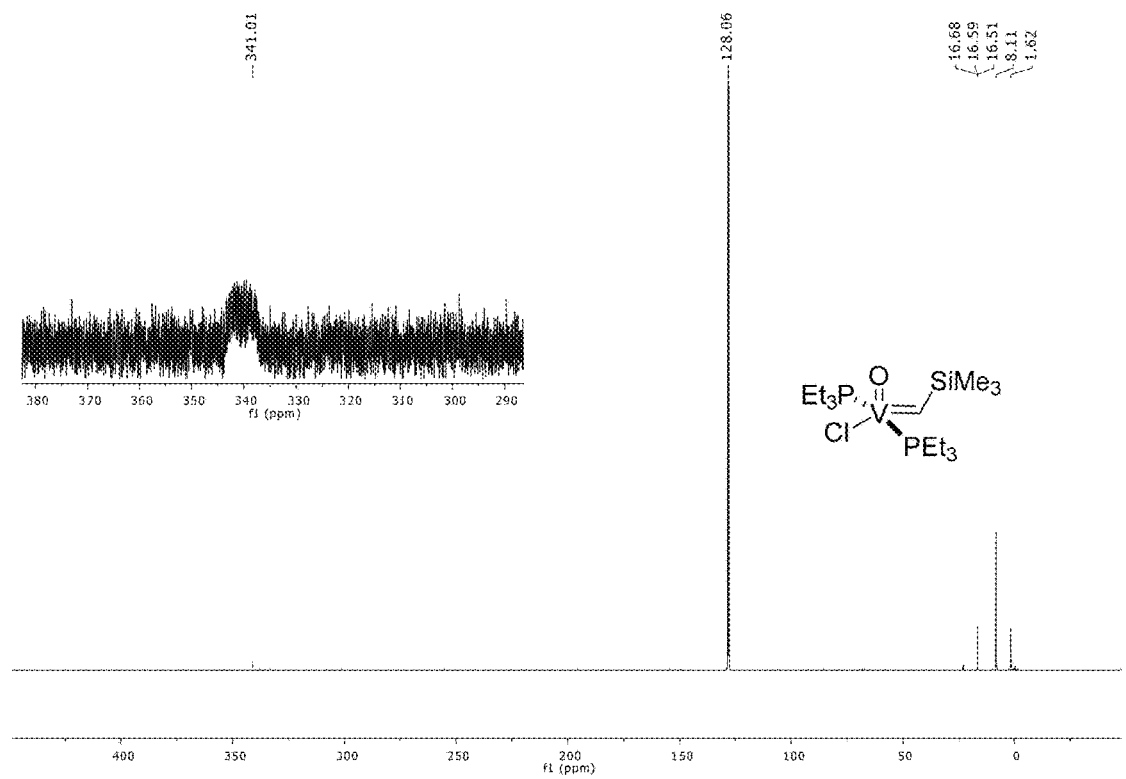
FIG. 10 shows $^{13}$C NMR spectrum of 14 (C$_6$D$_6$, 101 MHz, 24° C.).

The NMR spectra of 14 are shown in FIGS. 8-10.
$^1$H-NMR: (400 MHz, C$_6$D$_6$) δ=0.43 (s, 9H), 0.94-1.10 (m, 18H), 1.48-1.70 (m, 12H), 16.07 (s, 1H, V ═CH$_{syn}$), 17.31 (s, 0.03H, V ═CH$_{anti}$).
$^{31}$P NMR (162 MHz, C$_6$D$_6$): δ=17.3-30.9 (br. m).
$^{13}$C NMR (100 MHz, C$_6$D$_6$) δ=337.5-343.2 (br.), 16.6 (t, J=8.6 Hz), 8.1, 1.6.
Anal. Calcd for C$_{16}$H$_{40}$ClOP$_2$SiV: C, 45.23%; H, 9.49%, Found: C, 45.36%; H, 9.61%.
Cl—(VO)(IMes)2 ═CHSiMe3 (10')

Figure 23A:
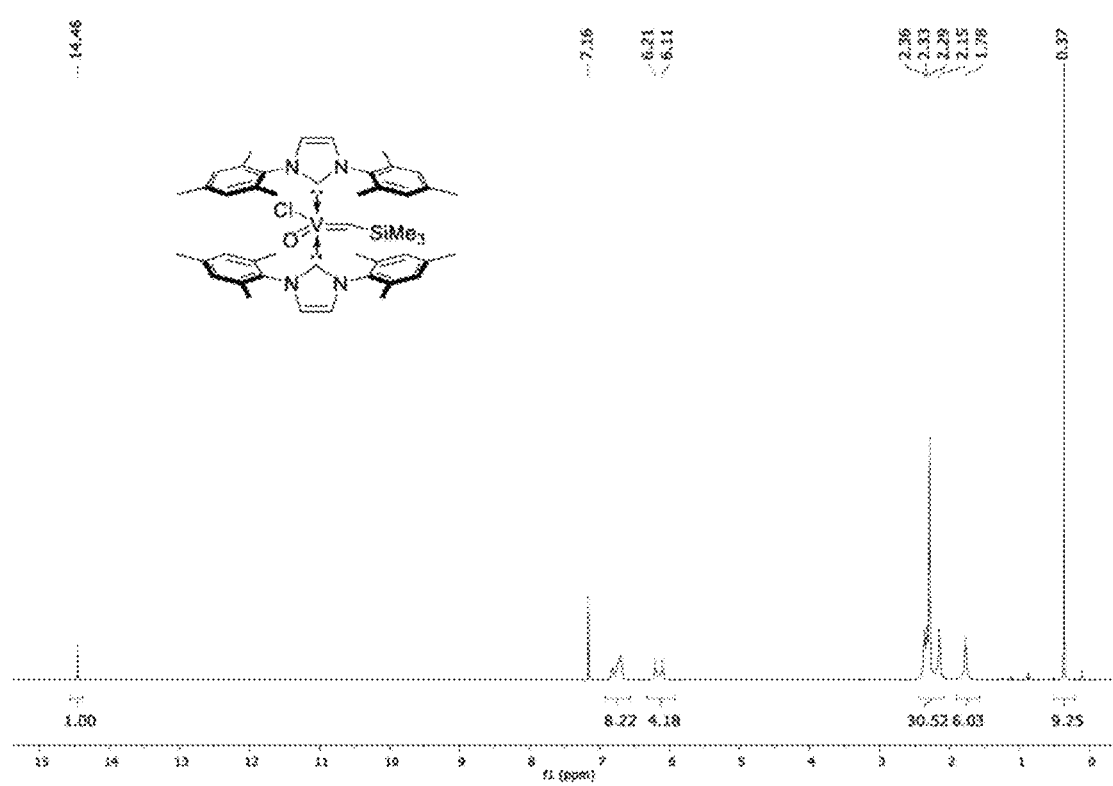
FIG. 23A shows $^1$H NMR spectrum 10' (C$_6$D$_6$, 400 MHz, 24° C.).
Figure 23B:
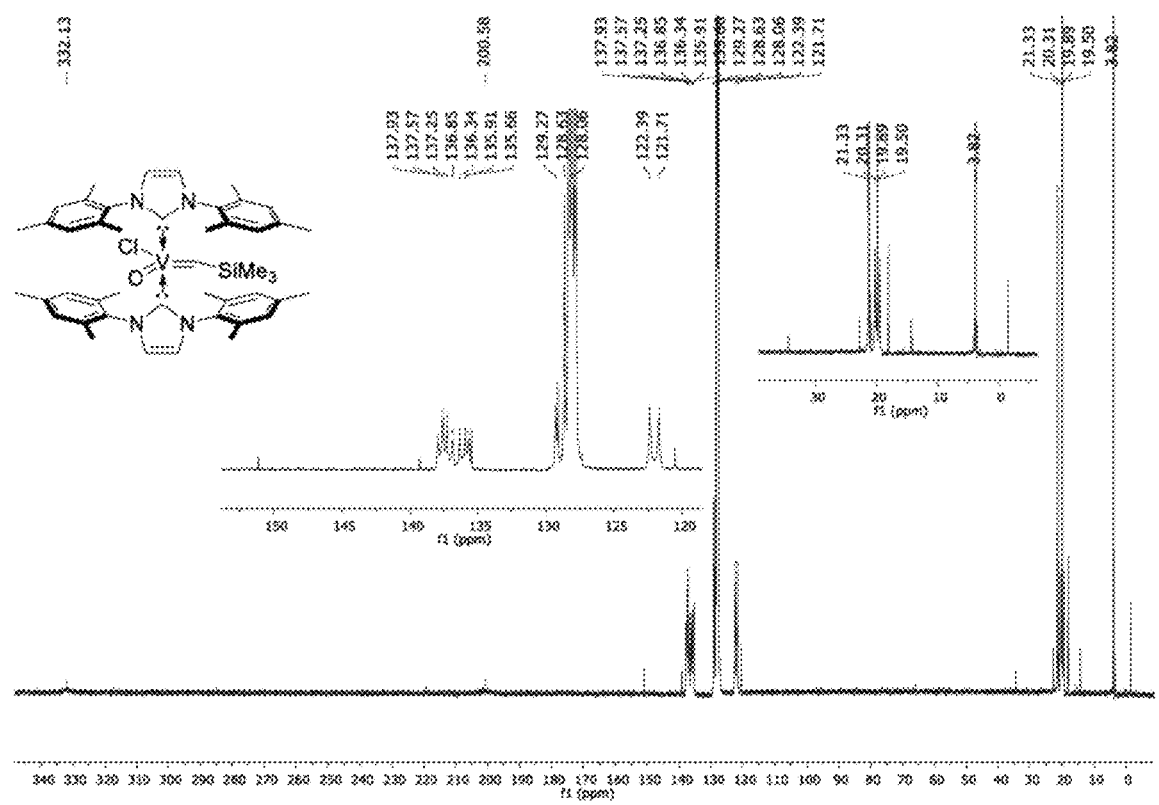
FIG. 23B shows $^{13}$C NMR spectrum of 10' (C$_6$D$_6$, 101 MHz, 24° C.).

IMes (891 mg, 2.94 mmol, 2.0 equiv.) was dissolved in a minimum amount of n-hexane at room temperature (~90 mL). The resulted solution was added to a vigorously stirred solution of complex 141 (624 mg, 1.47 mmol, 1.0 equiv.) in a minimum amount of n-hexane. The reaction mixture was stirred for 1 minute and rapidly filtered through syringe filter to a vial. The vial was immediately transferred to a freezer (−35° C.). After overnight the yellow crystals were filtered off and dried under vacuum. M=914 mg (78%) (FIG. 23).
$^1$H NMR: (C$_6$D$_6$, 400 MHz) δ=0.37 (s, 9H), 1.78 (br. s, 6H), 2.15 (br. s, 6H), 2.29 (br. s, 12H), 2.33 (br. s, 6H), 2.36 (br. s, 6H), 6.11 (br. s, 2H), 6.21 (br. s, 2H), 6.60-6.90 (m, 8H), 14.46 (s, 1H).
$^{13}$C NMR: (C$_6$D$_6$, 100 MHz) δ=332.1 (br.), 200.6 (br.), 137.9, 137.6, 137.3, 136.9, 136.3, 135.9, 135.66, 129.3, 128.6, 122.4, 121.7, 21.3, 20.3, 19.9, 19.5, 3.8.
Anal. Calcd for C46H58ClN4OSiV: C, 69.28%; H, 7.33%; N, 7.03%, Found: C, 69.42%; H, 7.18%; N, 7.00.

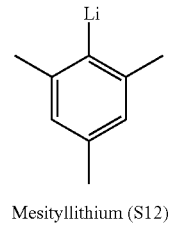

Mesityllithium (S12)

Bromomesitylene (5.00 mL, 6.50 g, 33.4 mmol, 1.0 equiv.) was mixed with ether (33 mL), cooled to −78° C. and a 2.5 M solution of n-butyllithium (14.7 mL, 36.7 mmol, 1.1 equiv.) was added dropwise over a period of five minute. After an hour at −78° C. the solution was allowed to warm up to room temperature to yield a white precipitate. Precipitate was collected, washed with ether, and dried under vacuum. M=2.70 g (64%).

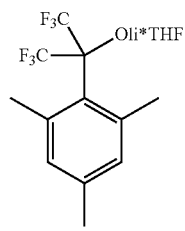

Lithium 1,1,1,3,3,3-hexafluoro-
2-mesitylpropan-2-
olate THF complex (S13)

Figure 24A:
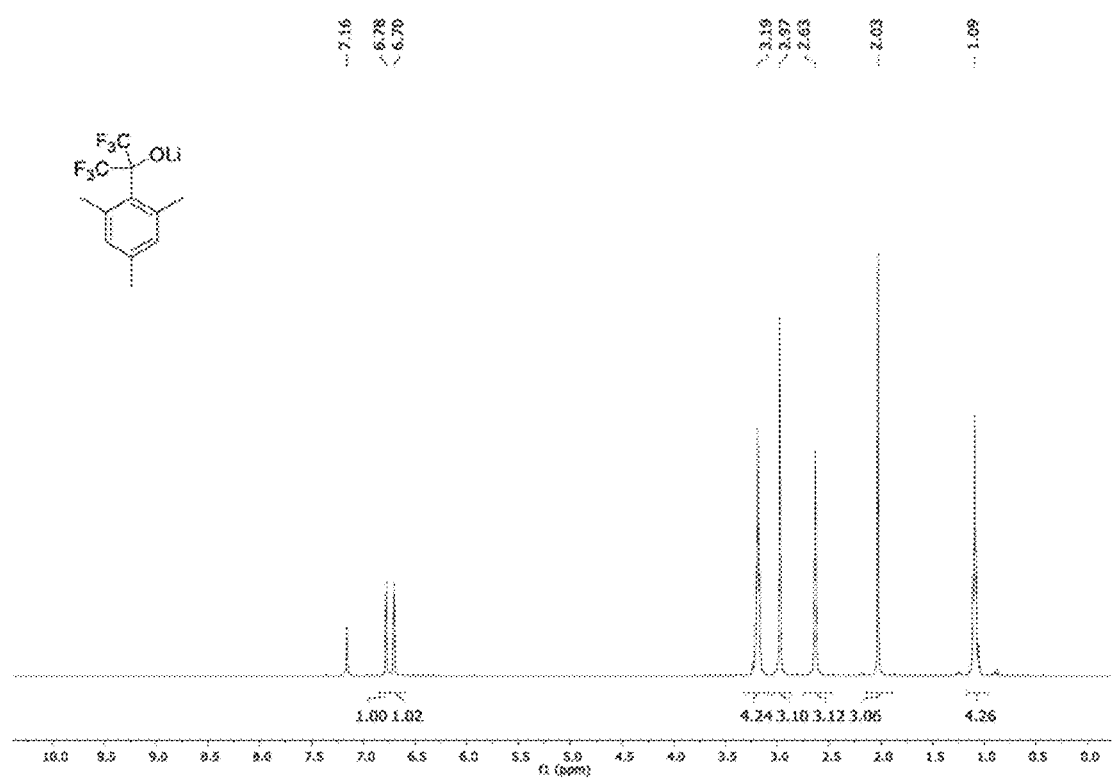
FIG. 24A shows $^1$H NMR spectrum S13 (C$_6$D$_6$, 400 MHz, 24° C.).
Figure 24B:
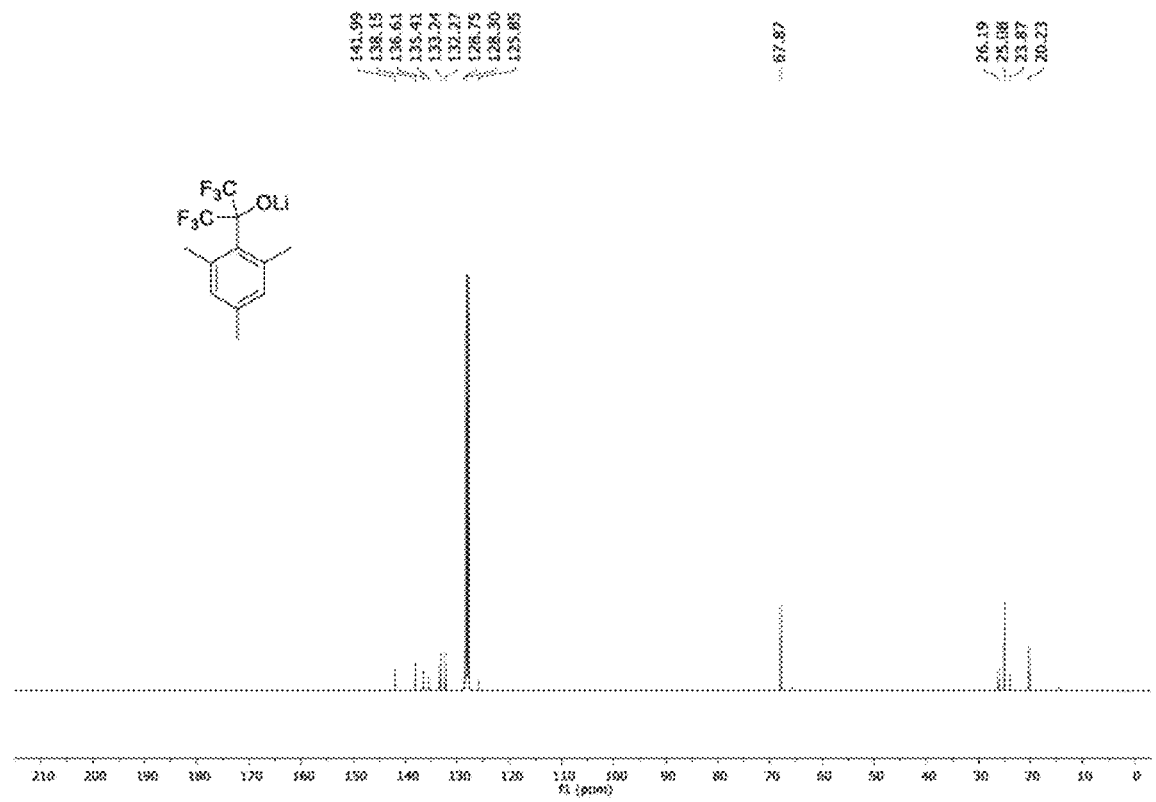
FIG. 24B shows $^{13}$C NMR spectrum of S13 (C$_6$D$_6$, 101 MHz, 24° C.).
Figure 24C:
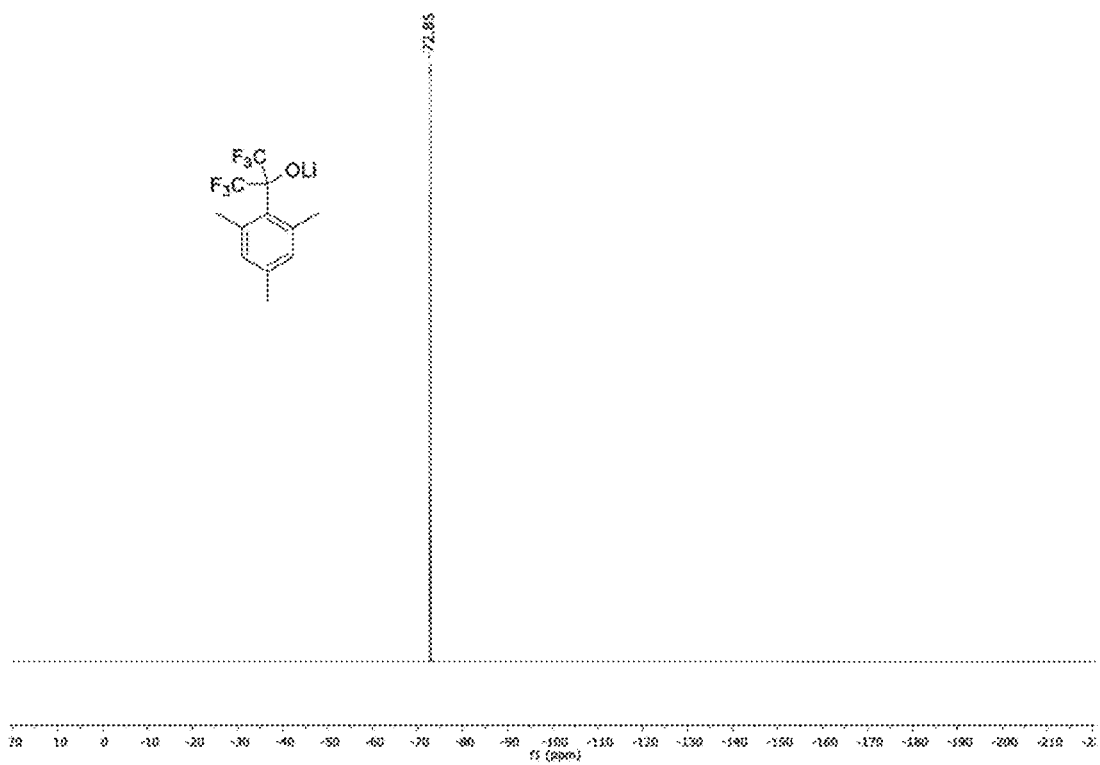
FIG. 24C shows $^{19}$F NMR spectrum of S13 (C$_6$D$_6$, 376 MHz, 24° C.).

Solid mesityllithium (4.03 g, 32.0 mmol, 1.0 equiv.) was dissolved in THF (30 mL) creating a light orange solution and was placed in a RBF (flask 1). A Schlenk flask containing ~50 mL of sulfuric acid (flask 2) was then put into the fume hood adjacent to flask 1. A hose connected to the spout of flask 2 and went through two bubblers filled with sulfuric acid then ended in a long needle which was poked into flask 1 through the septa with special care taken to make sure the needle was in the solution. Hexafluoroacetone hydrate (8.9 mL, 63.9 mmol, 2.0 equiv.) was then added dropwise through the septa of flask 2 dropwise into the sulfuric acid while the flask was being heated to 50° C. This instantly generated hexafluoroacetone gas which made its way through both bubblers and into the solution of flask 1. A 20 mL syringe was poked through the septa of flask 1 in order to relieve pressure, the syringe was emptied and reinserted as needed. After bubbling reaction mixture turned a very deep wine red and flask was warm to the touch, after a few more minutes reaction mixture turned a dark orange, then light orange. Solvent was then evaporated leaving behind a solid coated with a yellow oil. Pentane was added into the flask which dissolved the oil but precipitated out the solid. The solid was collected through filtration and washed with pentane (2×15 mL). M=3.80 g (33%) (FIG. 24).

$^1$H NMR: (C$_6$D$_6$, 400 MHz) δ=6.78 (s, 1H), 6.70 (s, 1H), 3.19 (t, J=6.5 Hz, 4H), 2.97 (s, 1H), 2.63 (s, 3H), 2.03 (s, 3H), 1.03-1.15 (m, 4H).

$^{19}$F NMR: (C$_6$D$_6$, 376 MHz) δ=−72.9.

$^{13}$C NMR: (C$_6$D$_6$, 100 MHz) δ=142.0, 138.2, 136.6, 135.4, 133.2, 132.3, 127.30 (q, J=292.2 Hz), 67.9, 26.2, 25.1, 23.9 (s, J=5.3 Hz), 20.2.

1,1,1,3,3,3-hexafluoro-2-mesitylpropan-ol (S14)

Figure 25A:
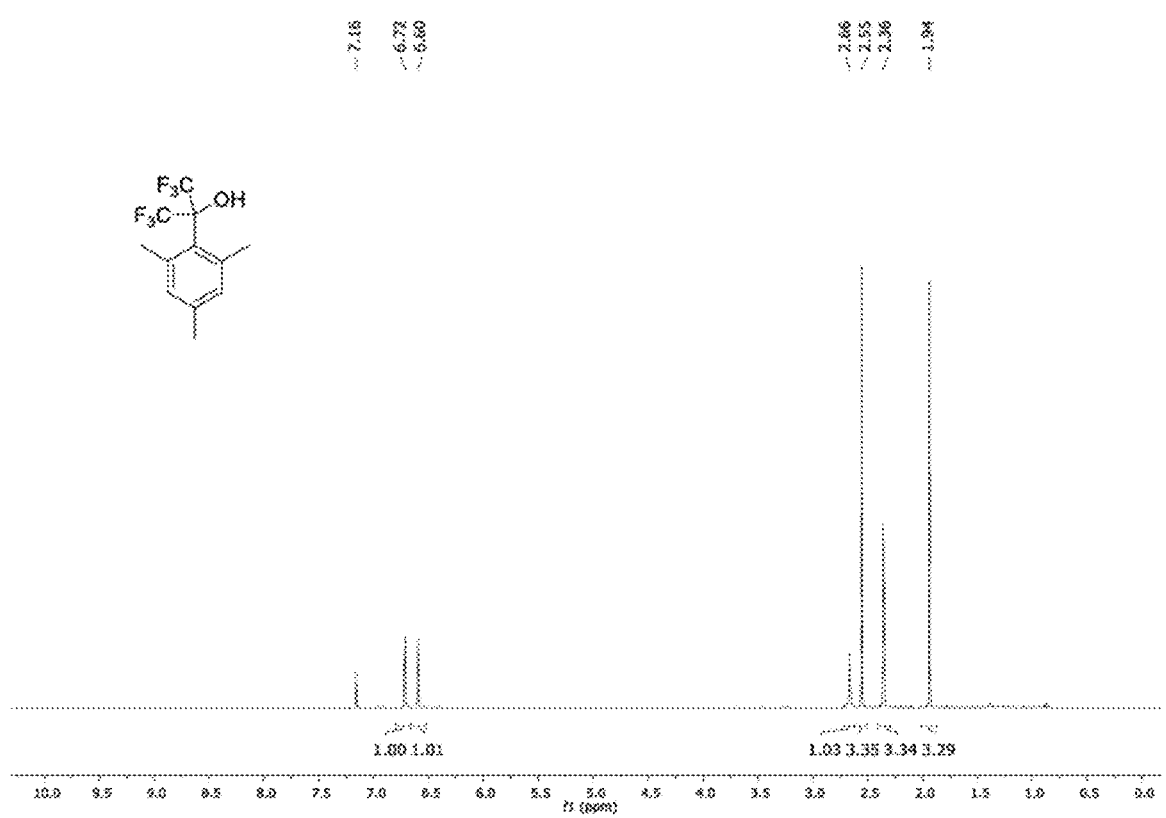
FIG. 25A shows $^1$H NMR spectrum S14 (C$_6$D$_6$, 400 MHz, 24° C.).
Figure 25B:
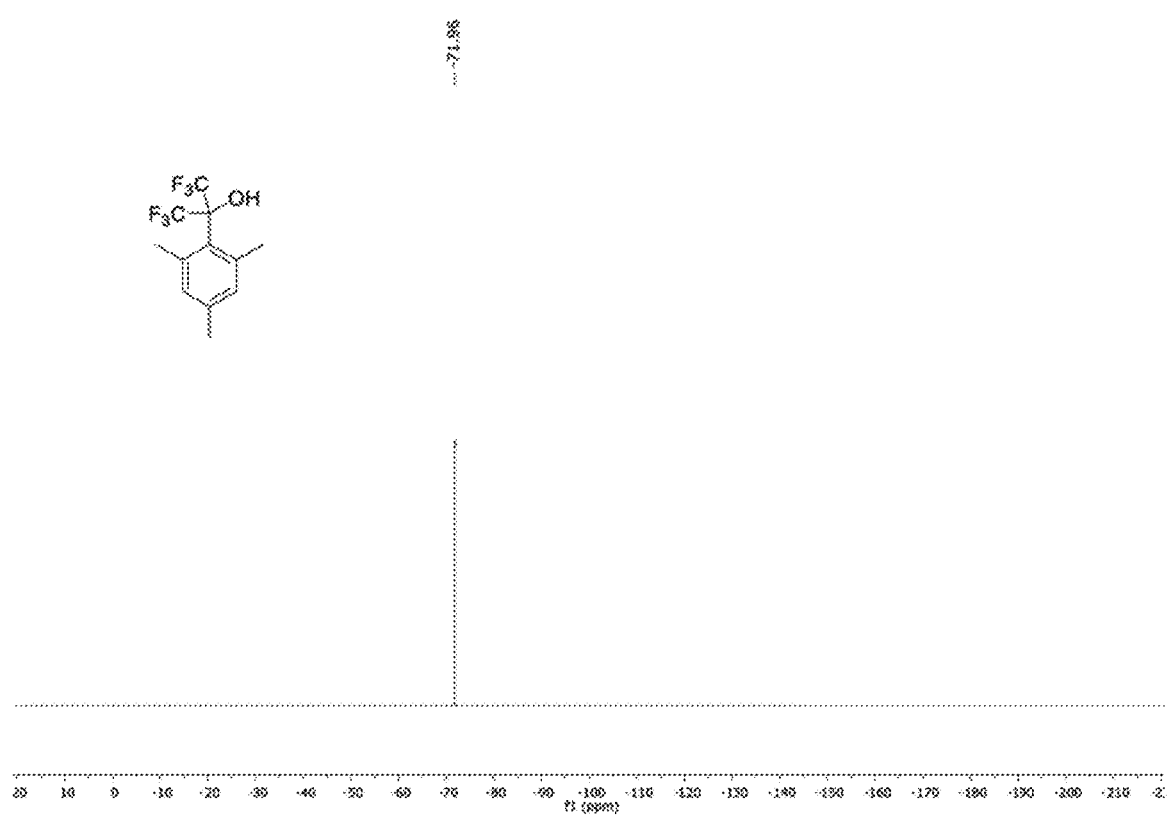
FIG. 25B shows $^{19}$F NMR spectrum of S14 (C$_6$D$_6$, 376 MHz, 24° C.).

S13 (3.80 g, 13.0 mmol, 1.0 equiv.) was dissolved in ether (40 mL) and 1M HCl in ether (16.9 mL, 16.9 mmol, 1.3 equiv.) was added in one portion. Once added a white precipitate of LiCl was formed. It was filtered off and washed with a small amount of ether. The solvent was evaporated to yield a yellow oily product. The product is volatile and should not be kept under vacuum. The residue was used in the next step without purification. M=3.72 g (100%) (FIG. 25).

$^1$H NMR: (C$_6$D$_6$, 400 MHz) δ=6.72 (s, 1H), 6.60 (s, 1H), 2.66 (s, 1H), 2.55 (s, 3H), 2.36 (s, 3H), 1.94 (s, 3H).

$^{19}$F NMR: (C$_6$D$_6$, 376 MHz) δ=−72.0.

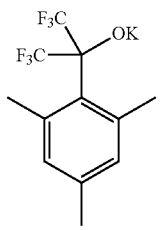

Potassium 1,1,1,3,3,3-hexafluoro-2-mesitylpropan-olate (S15)

Figure 26A:
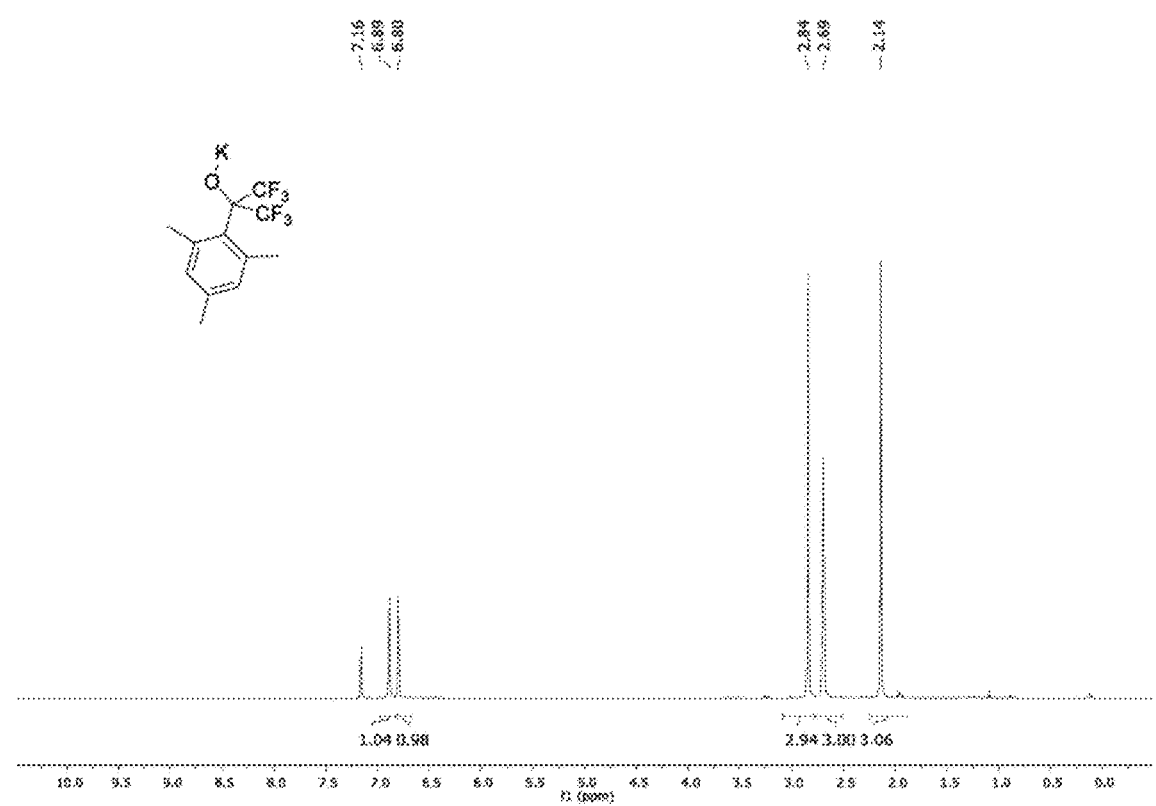
FIG. 26A shows $^1$H NMR spectrum S15 (C$_6$D$_6$, 400 MHz, 24° C.).
Figure 26B:
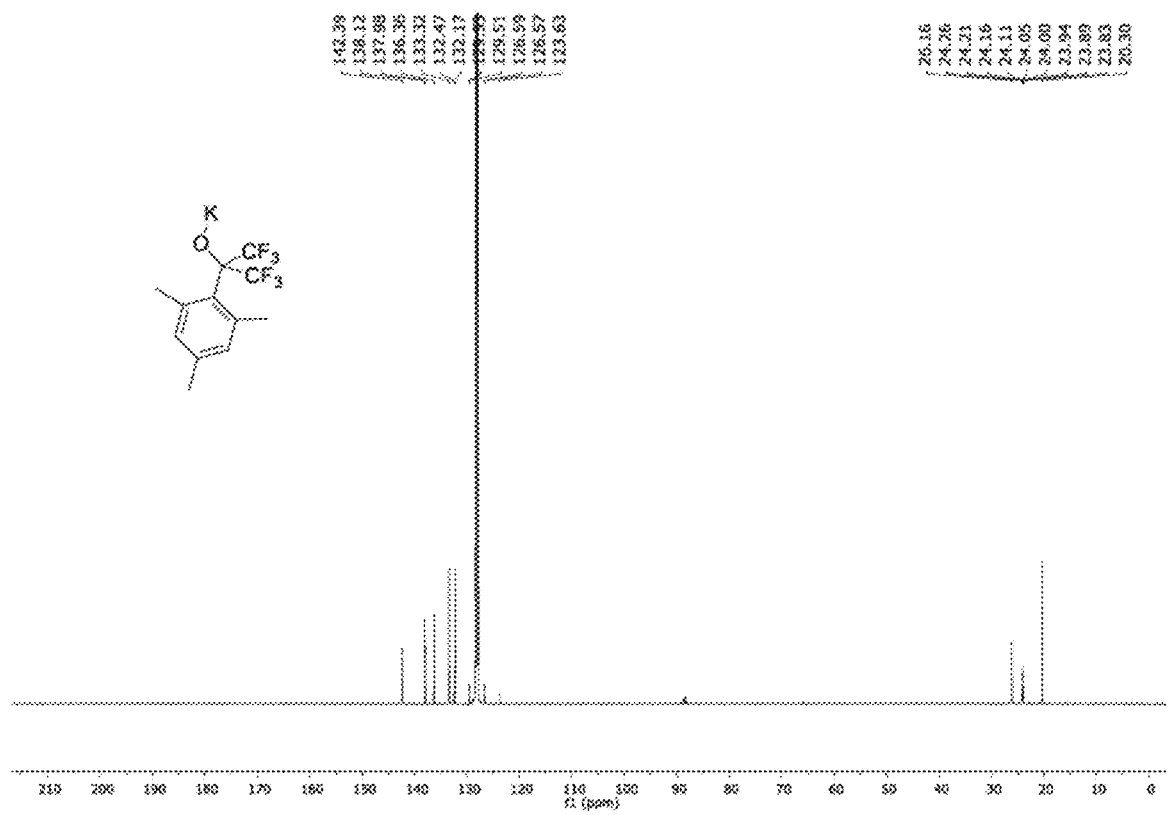
FIG. 26B shows $^{13}$C NMR spectrum of S15 (C$_6$D$_6$, 101 MHz, 24° C.).
Figure 26C:
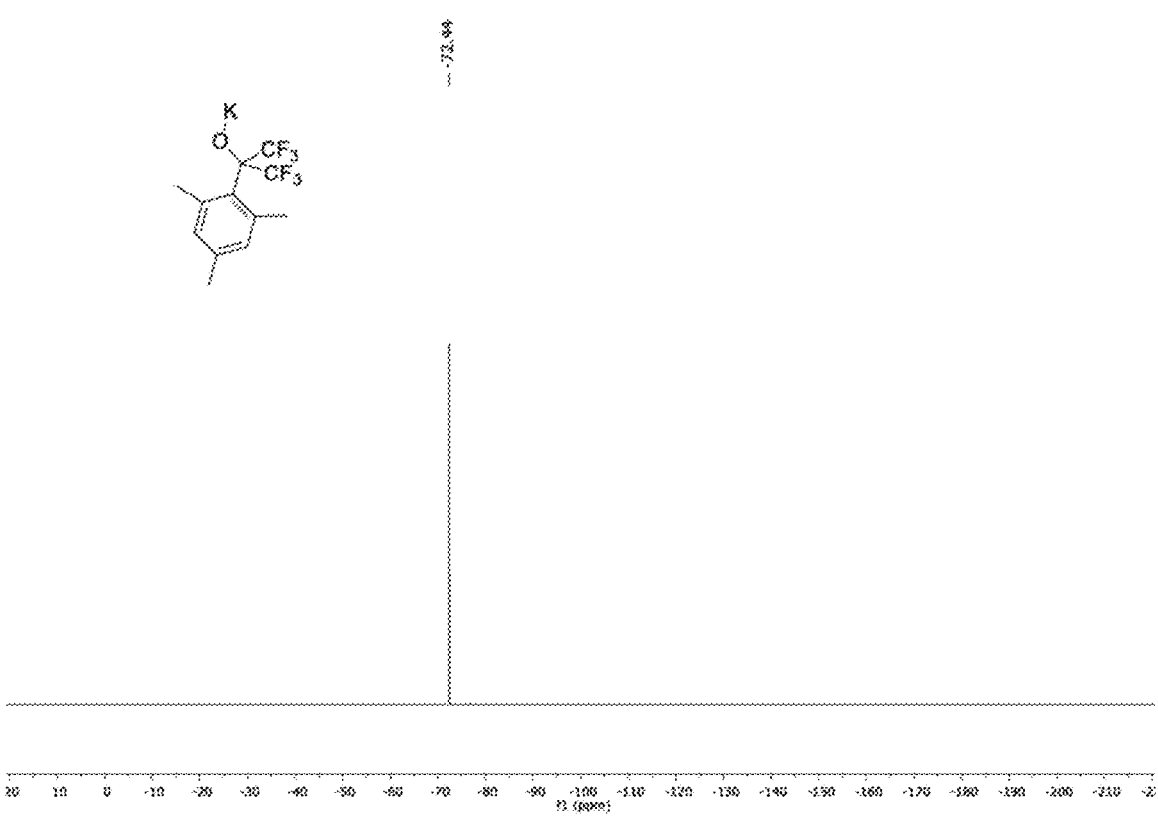
FIG. 26C shows $^{19}$F NMR spectrum of S15 (C$_6$D$_6$, 376 MHz, 24° C.).

Potassium bis(trimethylsilyl)amide (0.7 M in toluene, 20.4 mL, 1.1 equiv) was added dropwise into a cooled solution (−35° C.) of alcohol S14 (3.72 g, 13.0 mmol, 1.0 equiv.) in dry pentane. The solvent was evaporated under vacuum to yield a yellow oil. Pentane (~20 mL) was added to the flask, followed by ether (4 mL). The flask was shaken vigorously which caused the oil to dissolve and a white solid precipitated out. The flask was cooled down to −35° C. in a freezer before collecting the precipitate through filtration. M=2.29 g (54%) (FIG. 26).

$^1$H NMR: (C$_6$D$_6$, 400 MHz) δ=6.89 (s, 1H), 6.80 (s, 1H), 2.84 (s, 3H), 2.69 (s, 3H), 2.14 (s, 3H).

$^{19}$F NMR: (C$_6$D$_6$, 376 MHz) δ=−72.44.

$^{13}$C NMR: (C$_6$D$_6$, 100 MHz) δ=142.4, 138.1, 138.0, 136.4, 133.3, 132.2, 128.1 (q, J=296.2 Hz), 26.2, 24.1 (dq, J=11.0, 5.5 Hz), 20.3.

MesC(CF$_3$)$_2$O—(VO)(IMes)$_2$=CHSiMe$_3$ (11')

Solid 10' (150 mg, 0.188 mmol, 1.0 equiv.) and PhC(CF$_3$)$_2$OK (73 mg, 0.226 mmol, 1.2 equiv.) were mixed in a vial and ether (8 mL) was added. After 24 h of stirring at room temperature Me$_3$SiCH$_2$Cl (0.13 mL, 0.940 mmol, 5.0 equiv.) was added to remove free NHC. Reaction mixture was stirred for another 24 h, evaporated under vacuum and the residue was suspended in 3 mL of pentane.

Figure 27A:
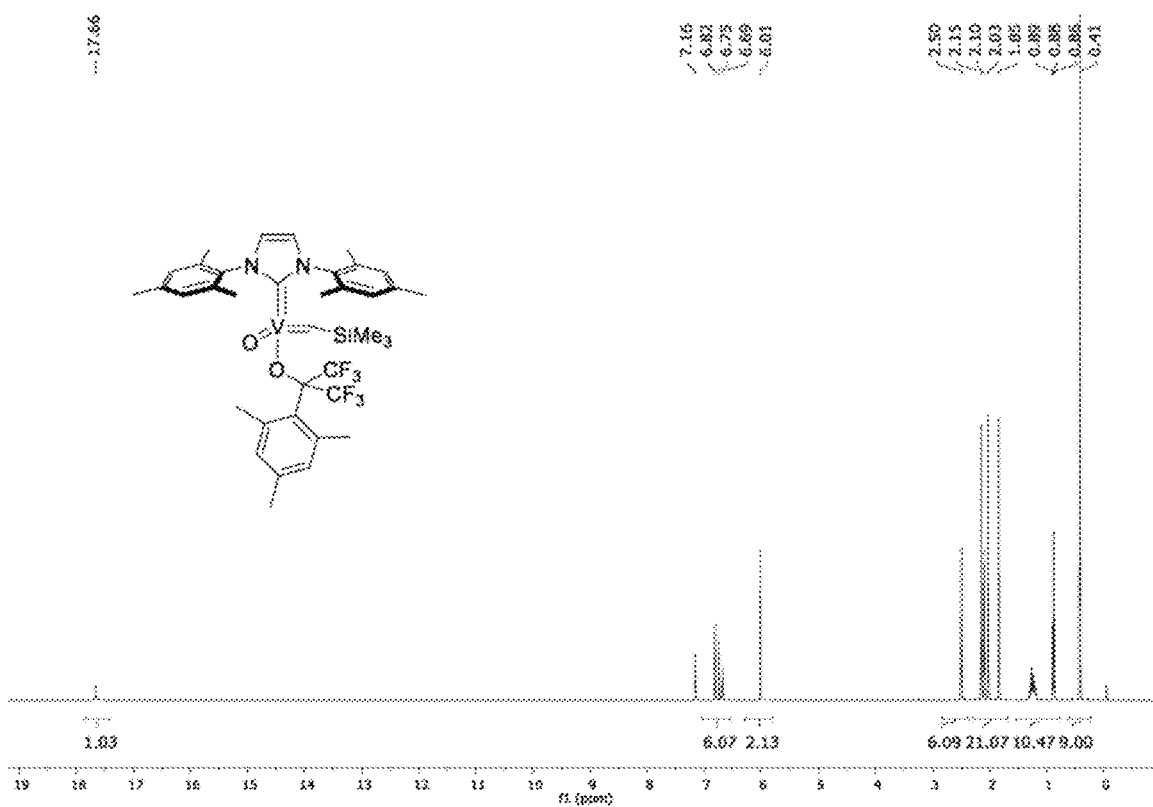
FIG. 27A shows $^1$H NMR spectrum 11' (C$_6$D$_6$, 400 MHz, 24° C.).
Figure 27B:
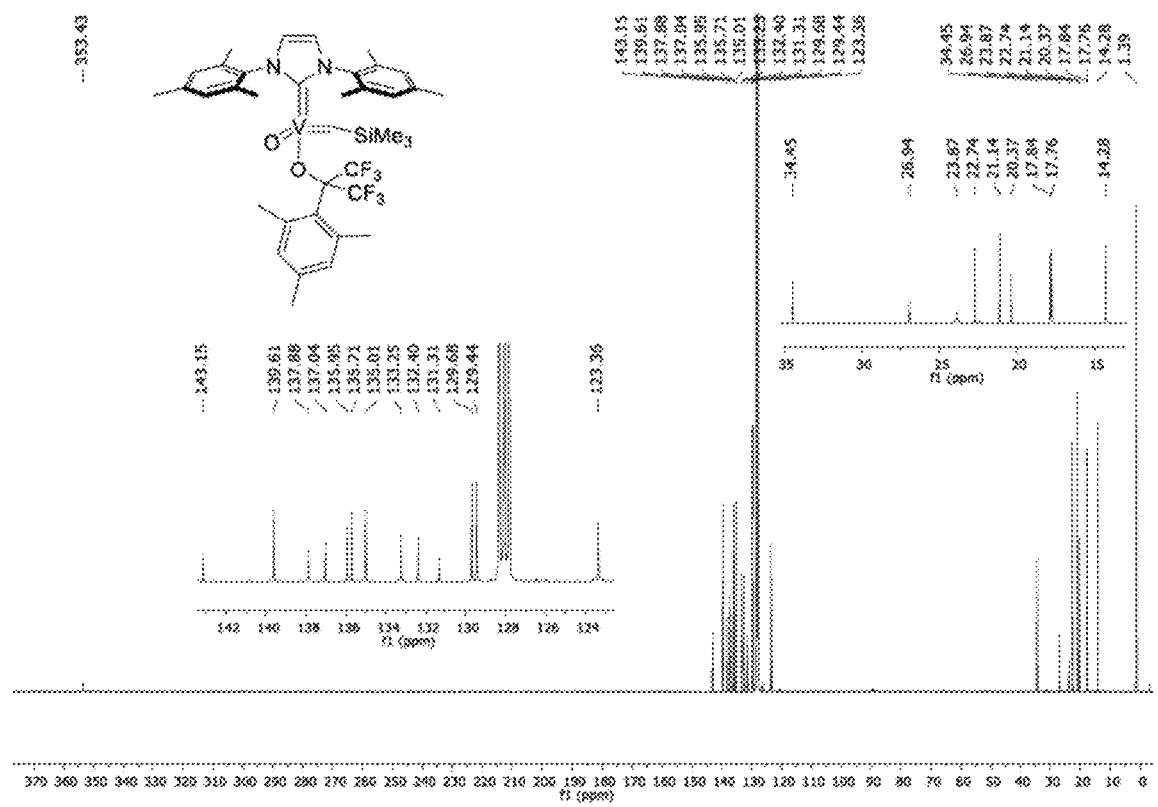
FIG. 27B shows $^{13}$C NMR spectrum of 11' (C$_6$D$_6$, 101 MHz, 24° C.).
Figure 27C:
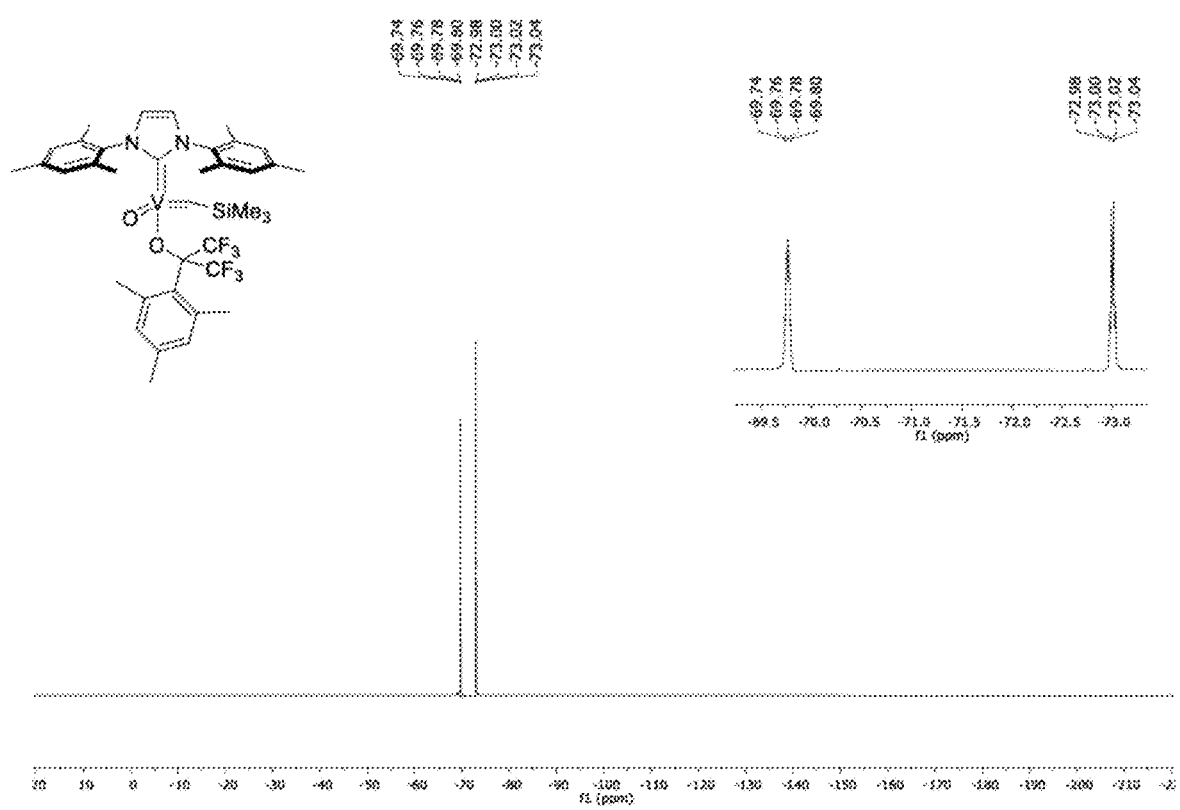
FIG. 27C shows $^{19}$F NMR spectrum of 11' (C$_6$D$_6$, 376 MHz, 24° C.).

Suspension was filtered through syringe filter and solution was placed to a freezer. After few days at −35° C. large dark violet crystals were collected by filtration and dried under vacuum. M=124 mg (89%) (FIG. 27).

$^1$H NMR: (C$_6$D$_6$, 400 MHz) δ=0.41 (s, 9H), 0.88 (t, J=7.1 Hz, 6H), 1.15-1.33 (m, 6H), 1.85 (s, 6H), 2.03 (s, 6H), 2.10 (s, 3H), 2.15 (s, 6H), 2.50 (s, 6H), 6.01 (s, 2H), 6.69 (s, 1H), 6.75 (s, 2H), 6.82 (s, 3H), 17.66 (s, 1H).

$^{19}$F NMR: (C$_6$D$_6$, 376 MHz) δ=−69.8 (q, J=7.5 Hz), −73.0 (q, J=7.4 Hz).

$^{13}$C NMR: (C$_6$D$_6$, 100 MHz) δ=1.4, 14.3 (pentane), 11.76, 11.84, 20.4, 21.1, 22.7 (pentane), 23.84 (dq, J=10.5, 5.6 Hz), 27.0 (pentane), 123.4, 129.4, 129.7, 131.3, 132.4, 133.3, 135.0, 135.7, 136.0, 137.0, 137.9, 139.6, 143.2, 353.4 (br.). CF3 signals overlaps with C$_6$D$_6$ signal.

11' crystallizes with 1 molecule of pentane as confirmed by 1H NMR and X-Ray. However during sample preparation for elemental analysis it slowly loses some of the pentane. The EA is consistent with 11·½pentane.

Anal. Calcd for (C37H45F6N2O2SiV)·0.5C5H12: C, 60.91%; H, 6.60%; N, 3.60%, Found: C, 60.51%; H, 6.84%; N, 3.46.

Scheme 1. Synthesis of S16.

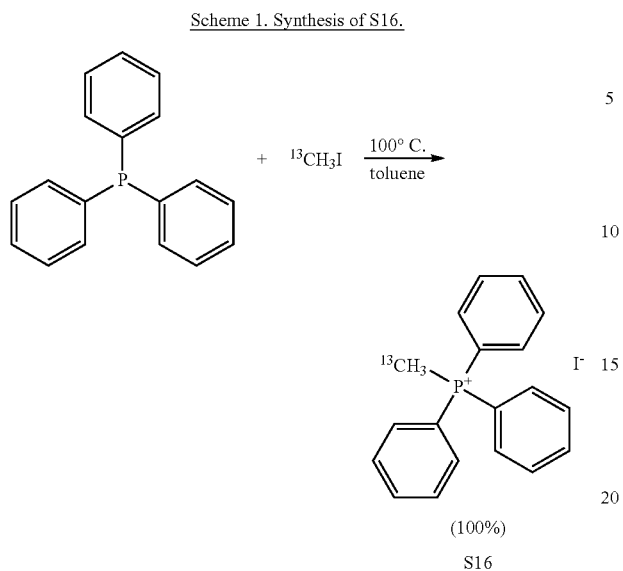

(100%)
S16

Figure 28A:
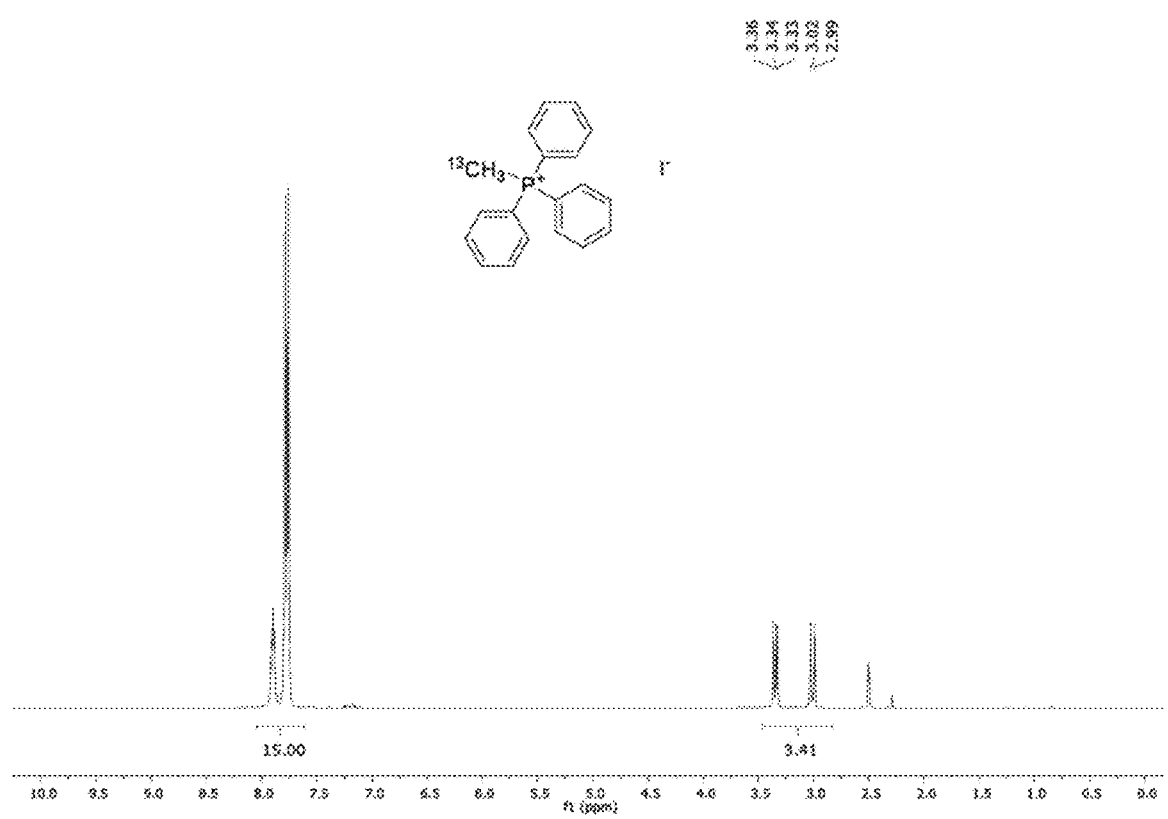
FIG. 28A shows $^1$H NMR spectrum S16 (DMSO-d6, 400 MHz, 24° C.).
Figure 28B:
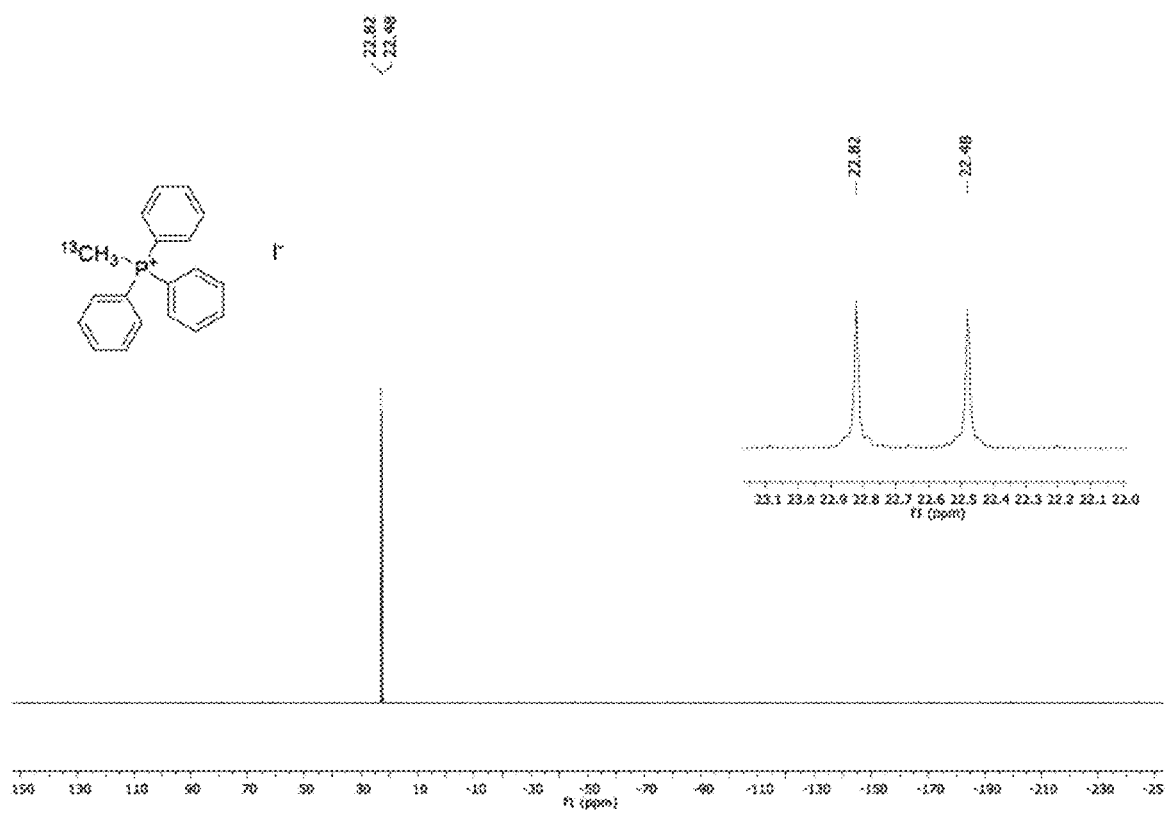
FIG. 28B shows $^{31}$P NMR spectrum of S16 (DMSO-d6, 162 MHz, 24° C.).
Figure 28C:
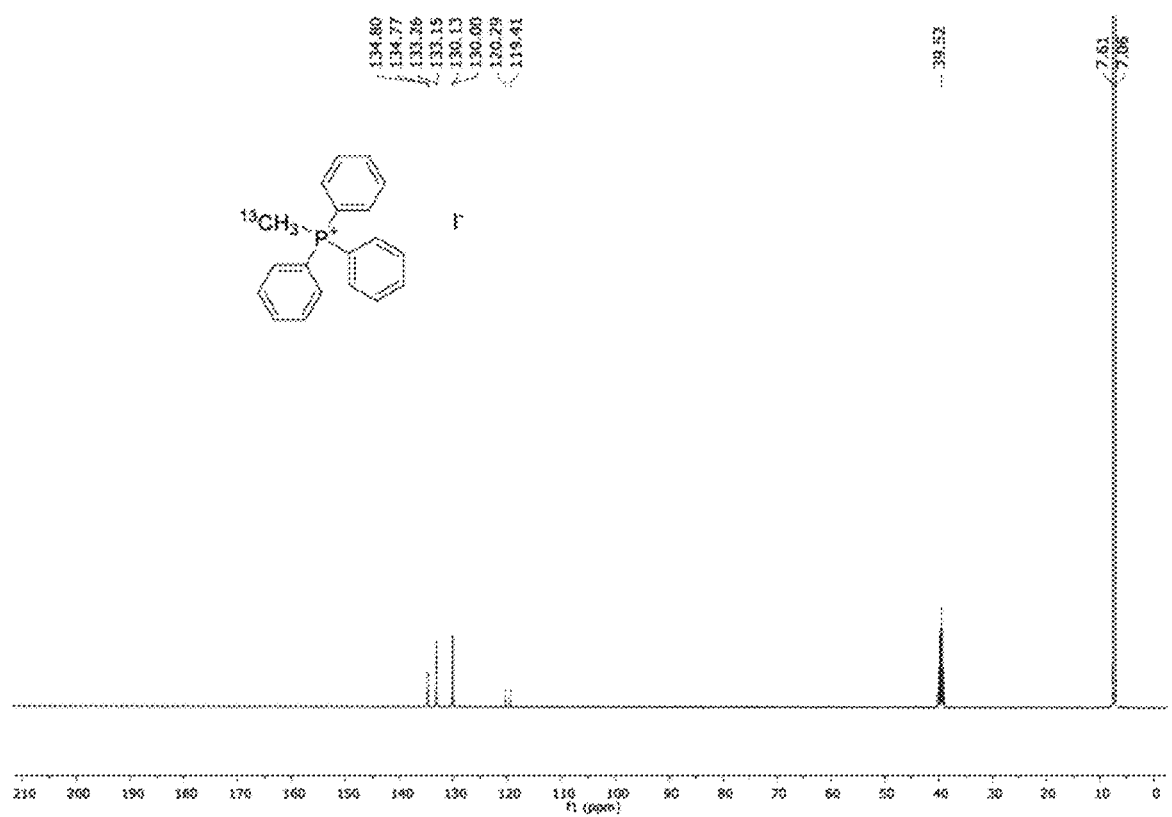
FIG. 28C shows $^{13}$C NMR spectrum of S16 (DMSO-d6, 101 MHz, 24° C.).

To a thick wall reaction vessel was added triphenyl phosphine (11.09 g, 42.3 mmol, 1.2 equiv.) and toluene (20.0 mL). To a solution was added $^{13}CH_3I$ (5.0 g, 34.9 mmol, 1.0 equiv.) and additional 5 mL of toluene was used to transfer residual iodomethane from the bottle. The formation of white precipitate starts almost immediately after mixing. The reaction vessel was tightly closed and was heated at 100° C. for 24 h with occasional shaking (magnetic stirring bar is not sufficient). The reaction mixture was then cooled to room temperature. The precipitate was filtered and washed with toluene (3×50 mL) and hexanes (3×50 mL). The resulted white solid was dried under vacuum. M=14.60 g (100%) (FIG. 28).

$^1$H NMR: (DMSO-d6, 400 MHz) δ=3.17 (dd, J=134.9, 14.6 Hz, 1H), 7.70-7.83 (m, 12H), 7.86-7.94 (m, 3H).

$^{31}$P NMR (DMSO-d6, 162 MHz) δ=22.65 (d, J=55.3 Hz).

$^{13}$C NMR: (DMSO-d6, 100 MHz) δ=134.8 (d, J=2.9 Hz), 133.2 (d, J=10.8 Hz), 130.1 (d, J=12.7 Hz), 119.9 (d, J=89.0 Hz), 7.34 (d, J=55.5 Hz).

Scheme 2. Synthesis of 13'-$^{13}$C.

(75%)

13'-$^{13}$C $^{13}$C Labeled 1-methoxy-4-vinylbenzene (13'-$^{13}$C)

Figure 29A:
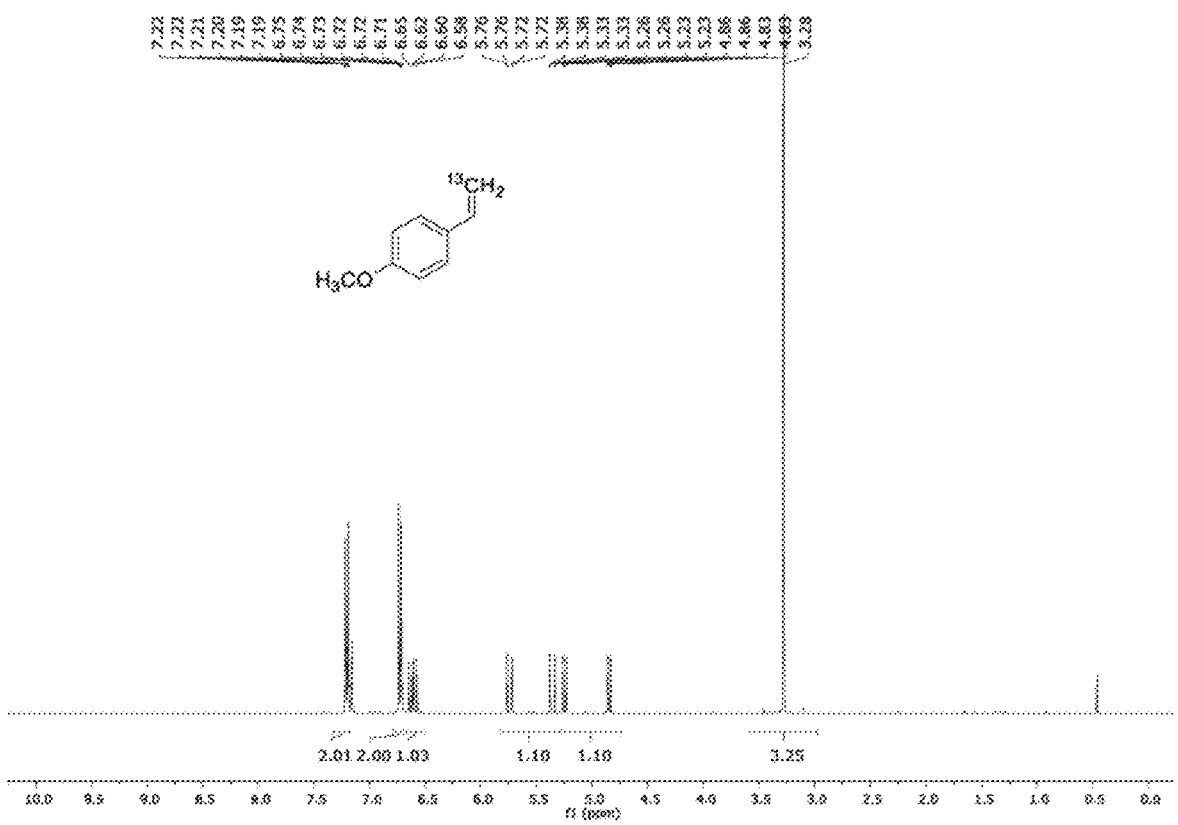
FIG. 29A shows $^1$H NMR spectrum 13'-$^{13}$C (C$_6$D$_6$, 400 MHz, 24° C.).
Figure 29B:
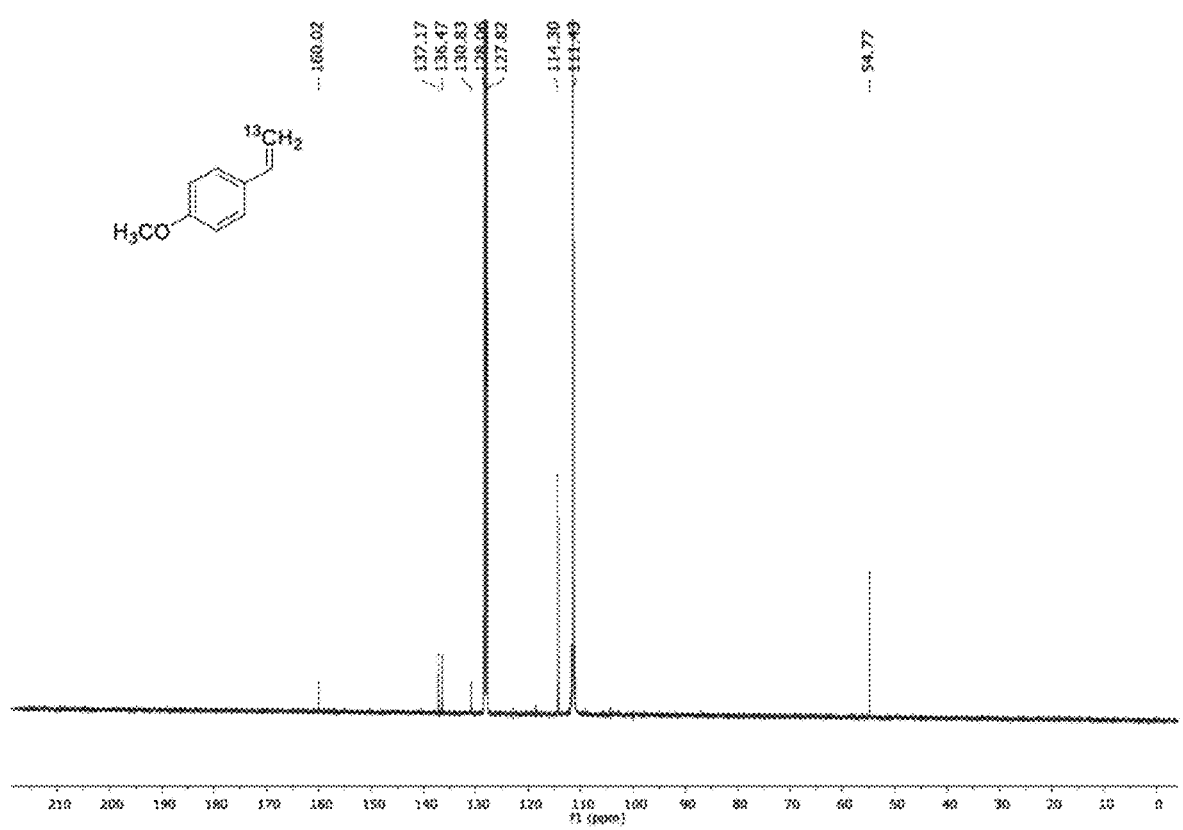
FIG. 29B shows $^{13}$C NMR spectrum of 13'-$^{13}$C (C$_6$D$_6$, 101 MHz, 24° C.).
Figure 29C:
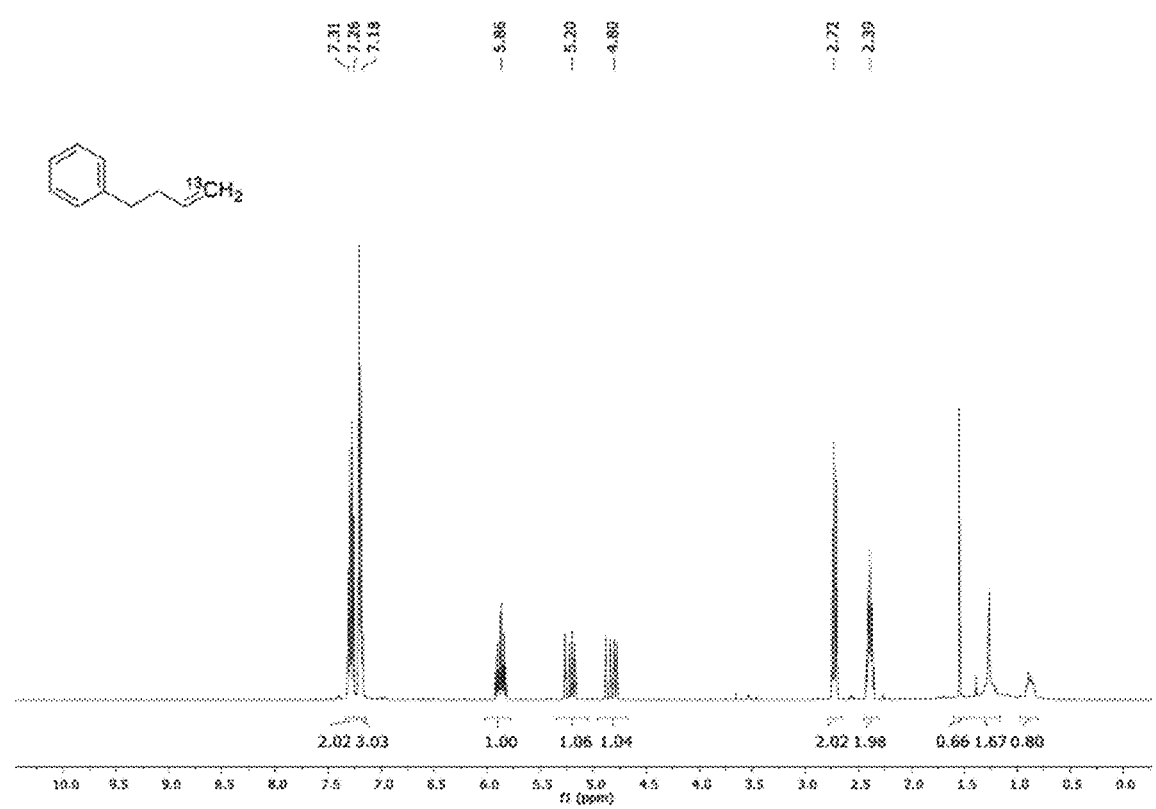
FIG. 29C shows $^1$H NMR spectrum 13'-$^{13}$C (CDCl$_3$, 400 MHz, 24° C.).

The salt ($^{13}CH_3$—$PPh_3$)+I– (1.00 g, 2.26 mmol, 1.0 equiv.) was suspended in THF (10 mL) and t-BuOK (333 mg, 2.97 mmol, 1.2 equiv.) was added to give a yellow suspension. Freshly distilled p-anisaldehyde (0.331 mL, 2.72 mmol, 1.1 equiv.) was added dropwise. Reaction mixture was stirred overnight at room temperature and 4M $LiBH_4$ in THF (~0.2 mL) was added to destroy unreacted aldehyde. Reaction mixture was dry loaded on silica gel. Flash chromatography with hexanes/ethyl acetate, 10:1 yield the title compound as a colorless liquid. M=250 mg (75%) (FIG. 29).

$^1$H NMR: ($C_6D_6$, 400 MHz) δ=7.23-7.18 (m, 2H), 6.76-6.69 (m, 2H), 6.61 (dd, J=17.6, 10.9 Hz, 1H), 5.55 (ddd, J=153.9, 17.6, 1.1 Hz, 1H), 5.05 (ddd, J=159.9, 10.9, 1.0 Hz, 1H), 3.28 (s, 3H).

$^{13}$C NMR: ($C_6D_6$, 100 MHz) δ=160.0, 136.8 (d, J=70.3 Hz), 130.8, 127.8, 114.3, 111.4 (labeled), 54.8.

Scheme 3. Synthesis of 9'-$^{13}$C.

(61%)

9'-$^{13}$C $^{13}$C Labeled but-3-en-1-ylbenzene (9'-$^{13}$C)

Figure 30:
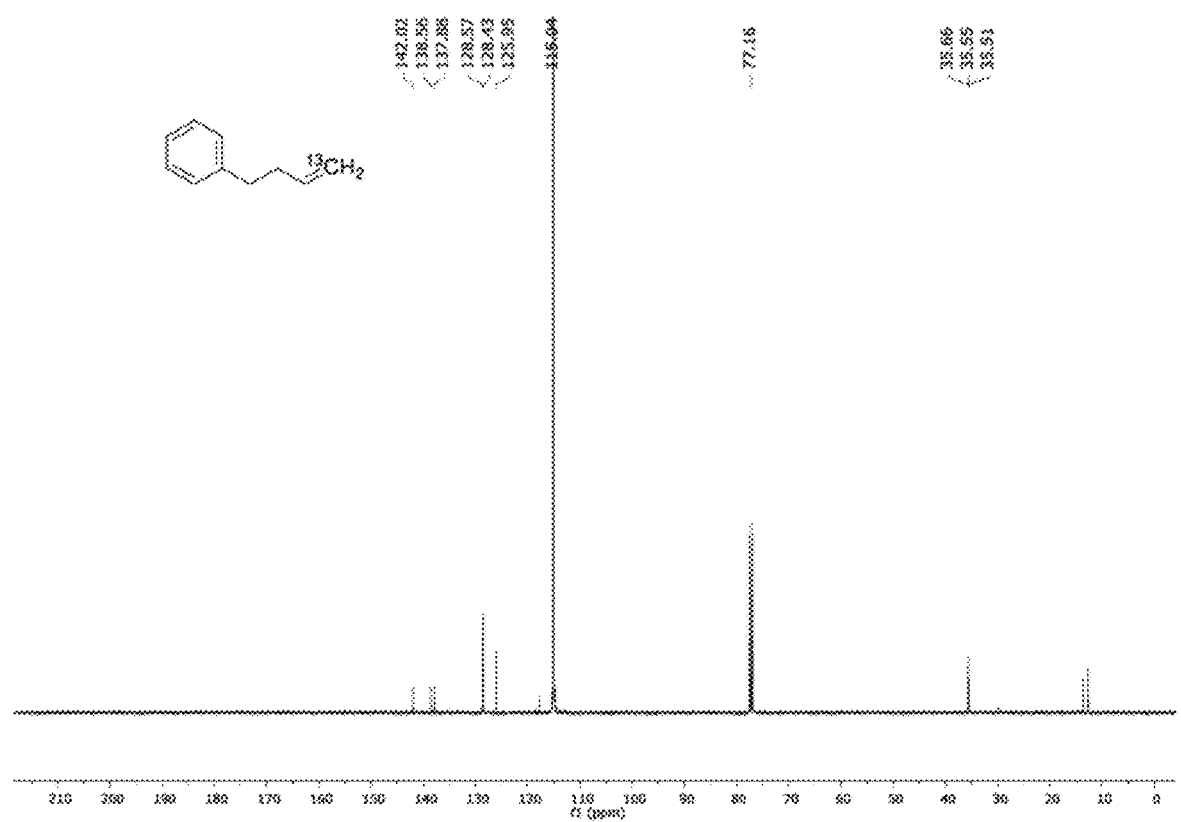
FIG. 30 shows $^{13}$C NMR spectrum of 9'-$^{13}$C (CDCl$_3$, 101 MHz, 24° C.).

The salt ($^{13}CH_3$—$PPh_3$)+I– (1.00 g, 2.26 mmol, 1.0 equiv.) was suspended in THF (10 mL) and t-BuOK (333 mg, 2.97 mmol, 1.2 equiv.) was added to give a yellow suspension. 3-phenylpropanal (0.358 mL, 2.72 mmol, 1.1 equiv.) was added dropwise. Reaction mixture was stirred overnight at room temperature and 4M $LiBH_4$ in THF (~0.2 mL) was added to destroy unreacted aldehyde. Reaction mixture was dry loaded on silica gel. Flash chromatography with hexanes yield the title compound as a colorless liquid. M=201 mg (61%) (FIG. 30).

$^1$H NMR: ($CDCl_3$, 400 MHz) δ=7.33-7.26 (m, 2H), 7.17-7.23 (m, 3H), 5.87 (ddt, J=16.9, 10.1, 6.5 Hz, 1H), 4.99 (ddq, J=153.6, 17.1, 1.7 Hz, 1H), 5.05 (dddt, J=157.5, 10.2, 2.0, 1.2 Hz, 2H), 2.72 (dd, J=9.0, 6.7 Hz, 1H), 2.39 (dddd, J=9.2, 7.7, 6.4, 4.9 Hz, 11H).

$^{13}$C NMR: ($CDCl_3$, 100 MHz) δ=142.0, 138.2 (d, J=69.3 Hz), 128.6, 128.4, 126.0, 115.0 (labeled), 35.7, 35.5 (d, J=3.8 Hz).

Scheme 4. Reaction of 11'.

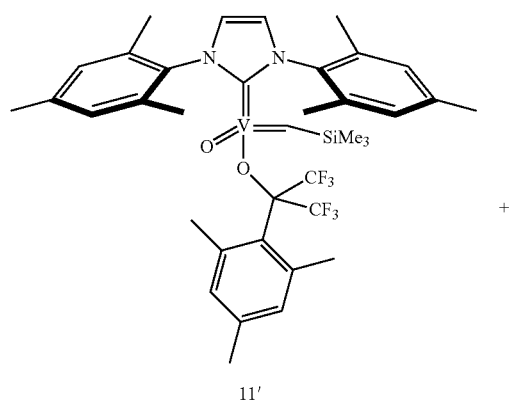

Scheme 5. Synthesis of of 10'-Ph.

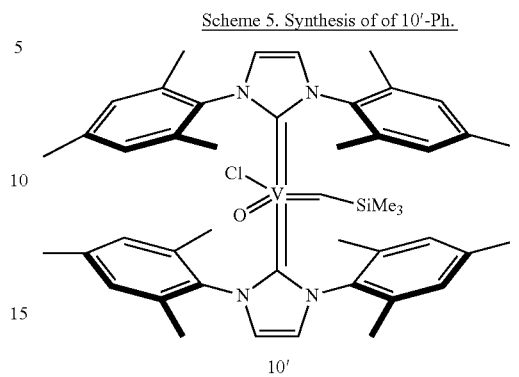

Figure 31:
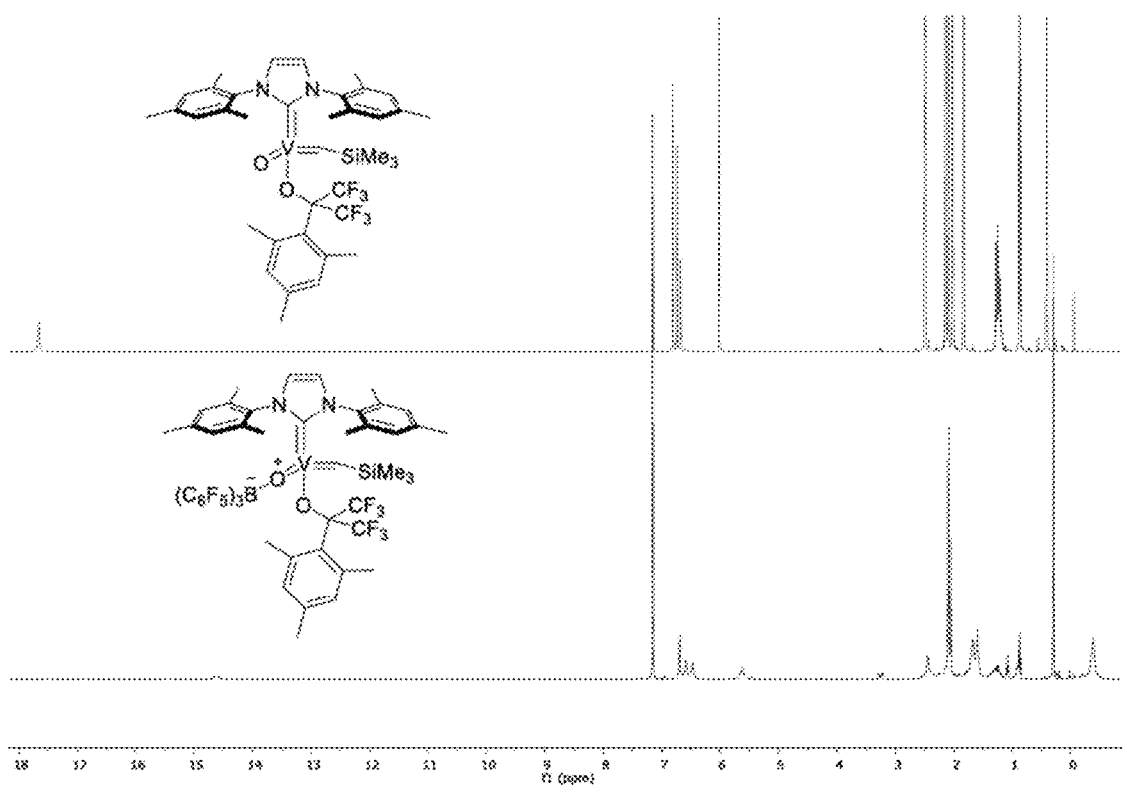
FIG. 31 shows fragment of $^1$H NMR spectrum of reaction of 11' with B(C$_6$F$_5$)$_3$ (C$_6$D$_6$, 400 MHz, 24° C.).

Complex 11' (7.50 mg, 10.1 μmol, 1.0 equiv.) was dissolved in C6D6 (0.5 mL). B(C6F5)3 (7.8 mg, 15.2 μmol, 1.5 equiv.) was dissolved in C6D6 (0.5 mL) and added to a stirred solution of 11'. The solution was transferred to J. Young NMR tube and 1H NMR was checked as soon as possible (FIG. 31).

Alkylidene Exchange (NMR Experiments)

Figure 32A:
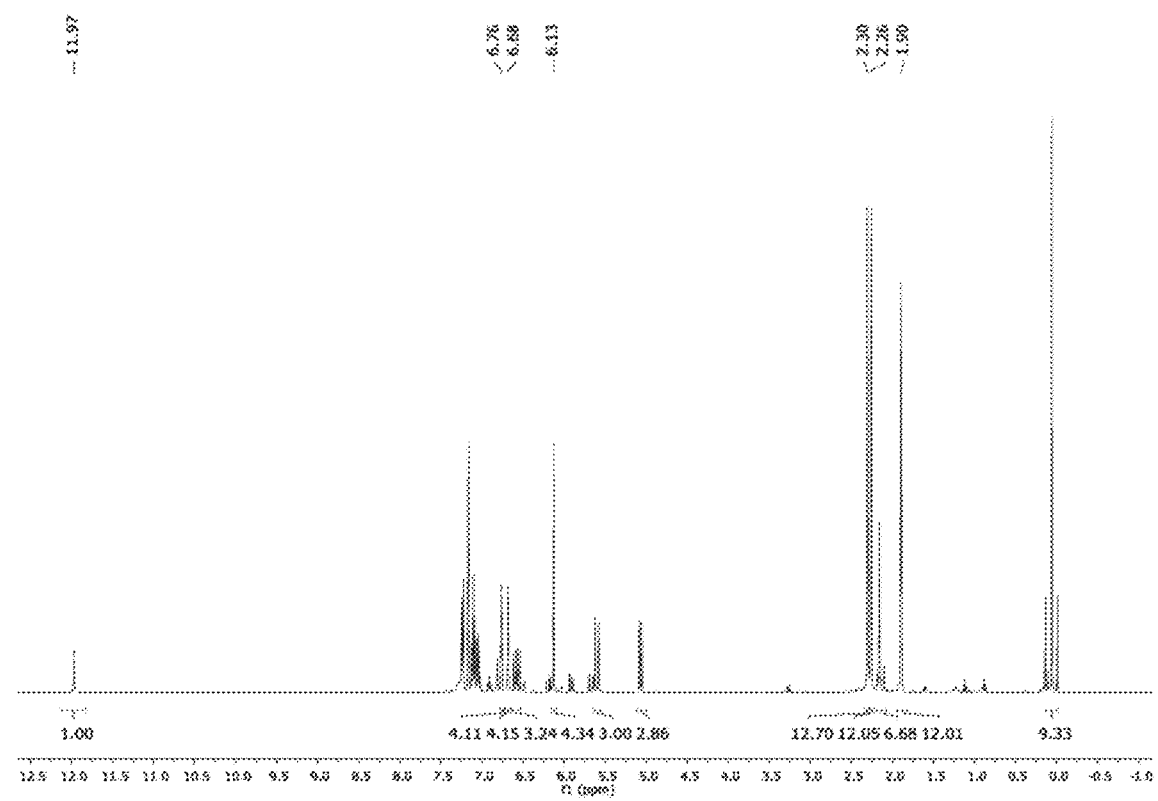
FIG. 32A shows $^1$H NMR spectrum of alkylidene exchange experiment (C$_6$D$_6$, 400 MHz, 24° C.).
Figure 32B:
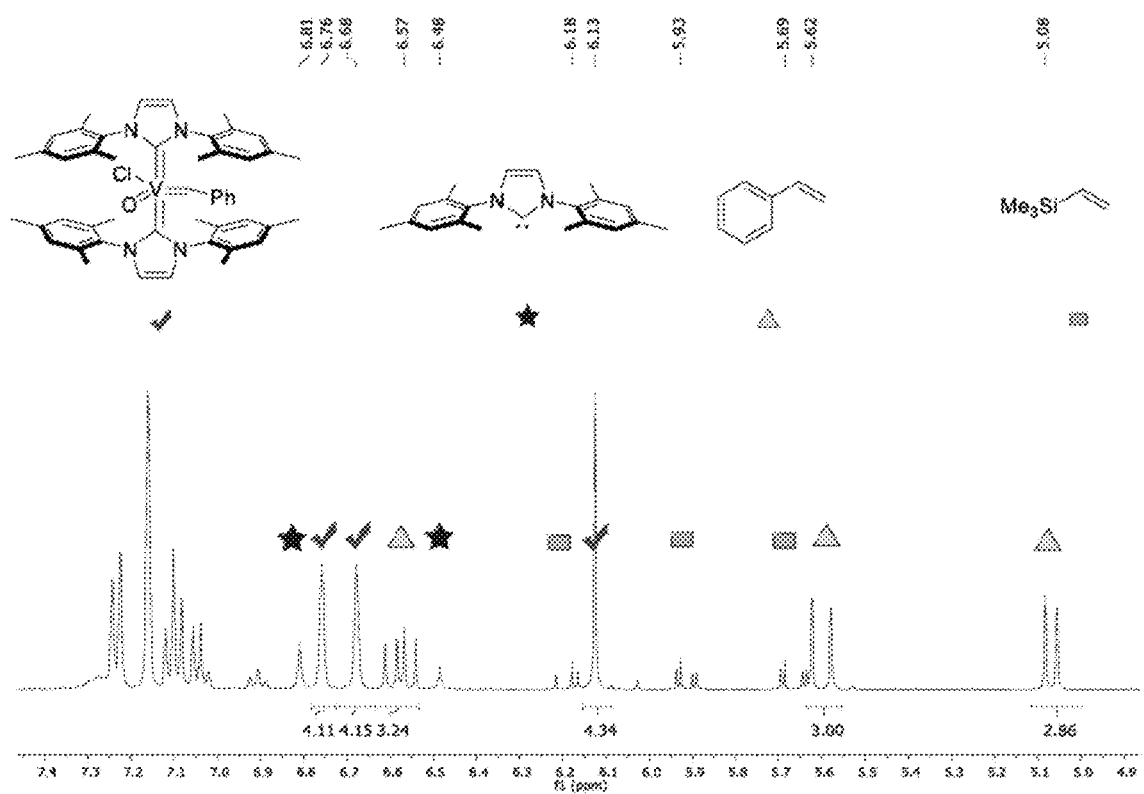
FIG. 32B shows fragments of $^1$H NMR spectrum of alkylidene exchange experiment (C$_6$D$_6$, 400 MHz, 24° C.).

10' (20 mg, 25.08 μmol, 1.0 equiv.) was dissolved in $C_6D_6$ (0.8 mL) and styrene (8.62 μL, 75.24 μmol, 3.0 equiv.) was added. The solution was transferred to J. Young NMR tube and $^1$H NMR was checked after ~24 hours at room temperature. See FIG. 32 for $^1$H NMR.

$^1$H NMR: ($C_6D_6$, 400 MHz): δ=11.97 (s, 1H), 7.30-6.85 (m, 5H), 6.76 (s, 4H), 6.68 (s, 4H), 6.13 (s, 4H), 2.30 (s, 12H), 2.26 (s, 12H), 1.90 (s, 12H).

Scheme 6. Synthesis of of 10'-OMe.

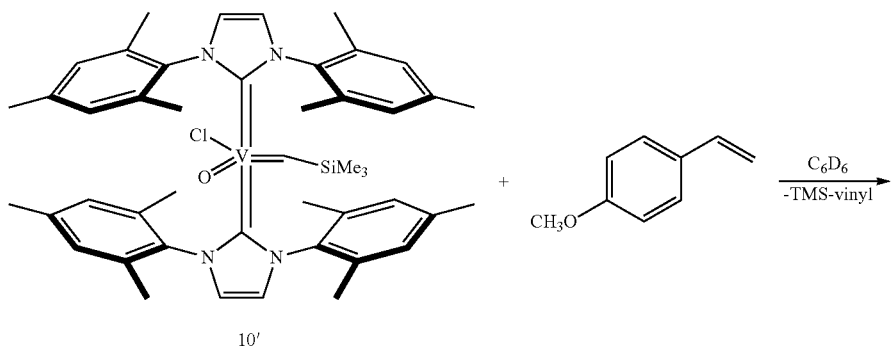

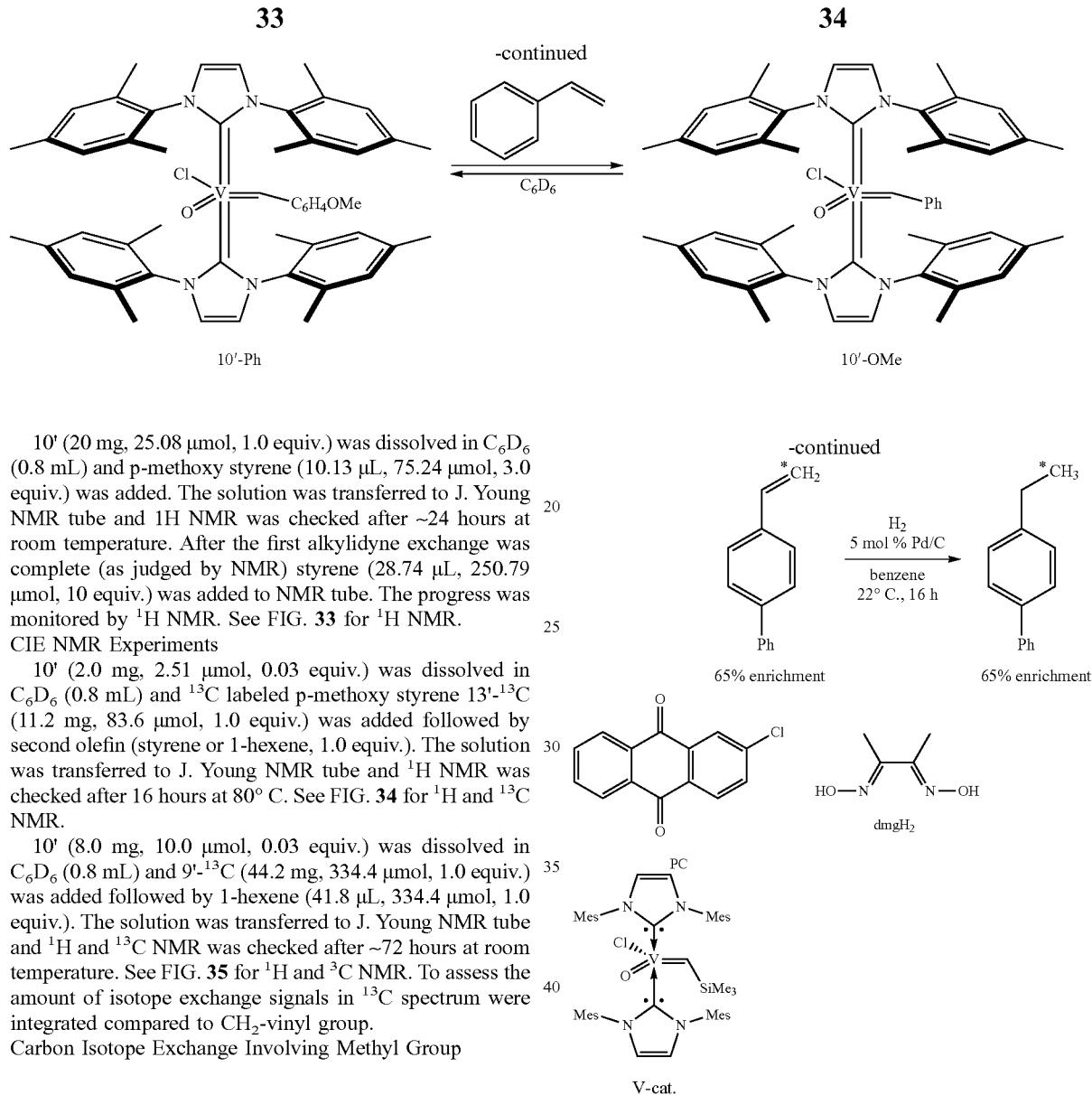

Figure 33:
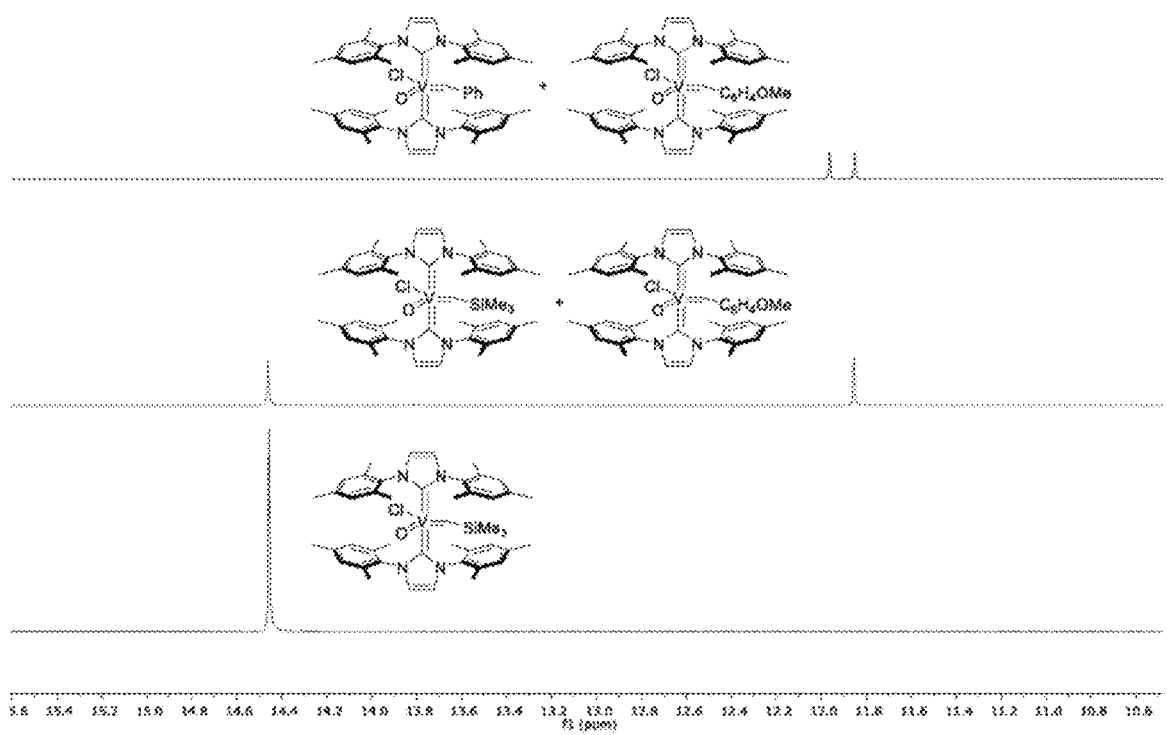
FIG. 33 shows fragments of $^1$H NMR spectrum of alkylidene exchange experiment (C$_6$D$_6$, 400 MHz, 24° C.).
Figure 34A:
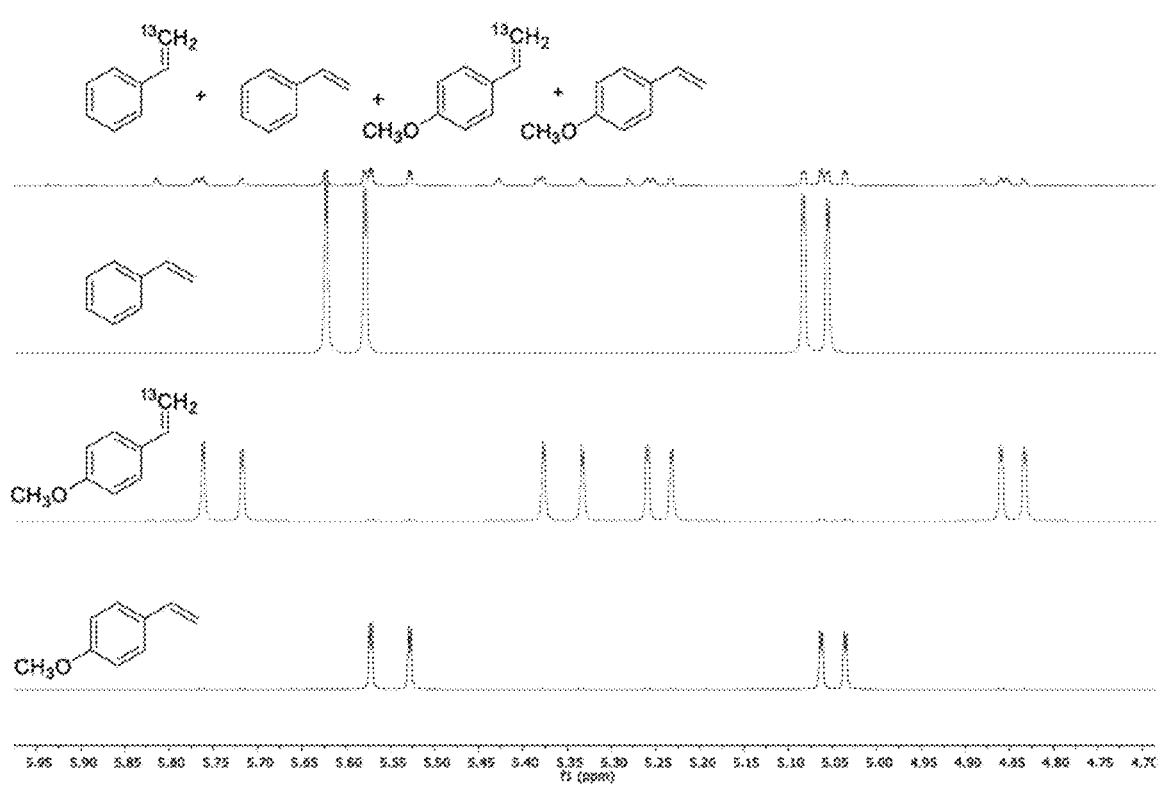
FIG. 34A shows fragments of $^1$H NMR spectrum of CIE experiment with styrene (C$_6$D$_6$, 400 MHz, 24° C.).
Figure 34B:
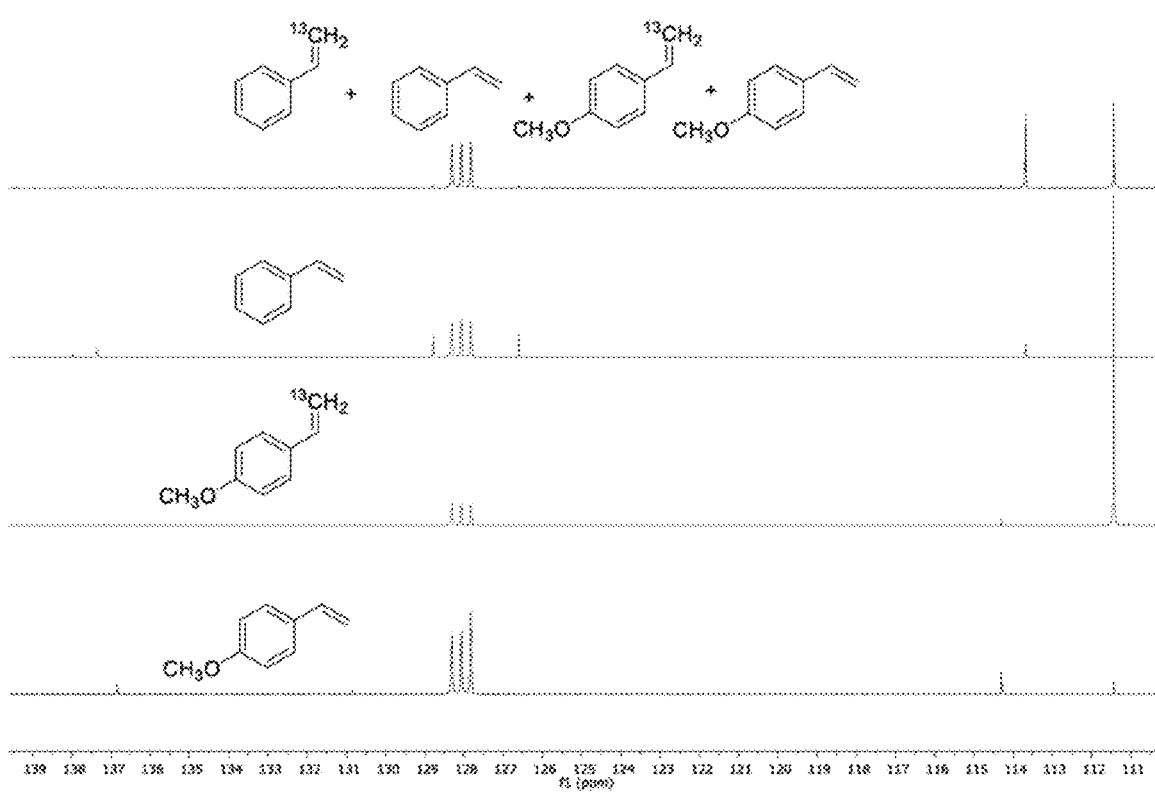
FIG. 34B shows fragments of $^{13}$C NMR spectrum of CIE experiment with styrene (C$_6$D$_6$, 400 MHz, 24° C.).
Figure 34C:
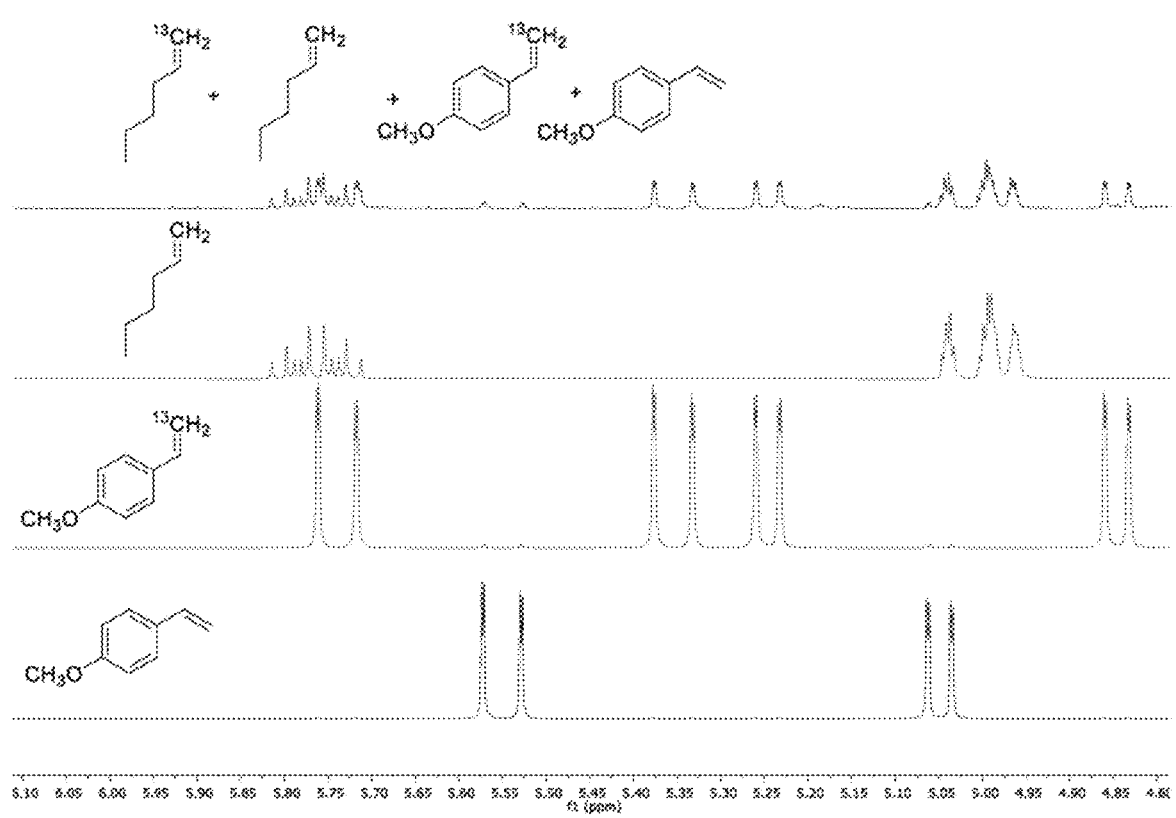
FIG. 34C shows fragments of $^1$H NMR spectrum of CIE experiment with hexene-1 (C$_6$D$_6$, 400 MHz, 24° C.).
Figure 34D:
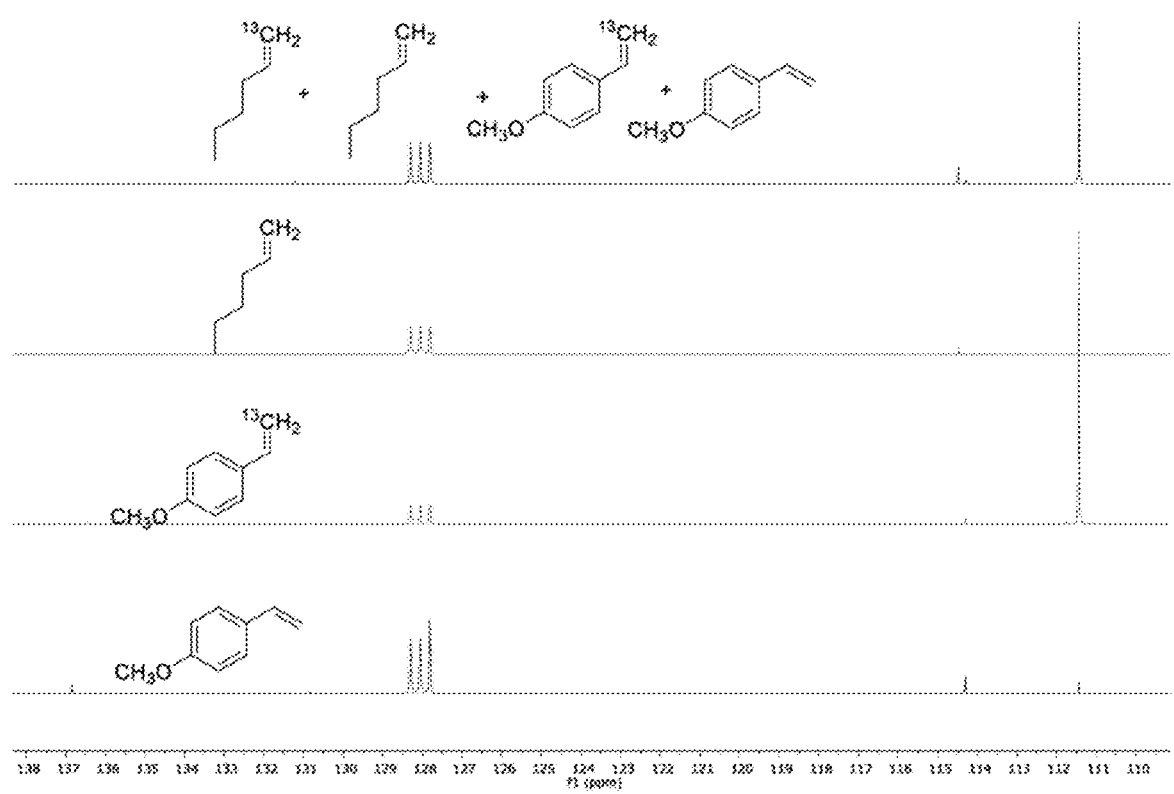
FIG. 34D shows fragments of $^{13}$C NMR spectrum of CIE experiment with hexene-1 (C$_6$D$_6$, 400 MHz, 24° C.).

10' (20 mg, 25.08 μmol, 1.0 equiv.) was dissolved in $C_6D_6$ (0.8 mL) and p-methoxy styrene (10.13 μL, 75.24 μmol, 3.0 equiv.) was added. The solution was transferred to J. Young NMR tube and 1H NMR was checked after ~24 hours at room temperature. After the first alkylidyne exchange was complete (as judged by NMR) styrene (28.74 μL, 250.79 μmol, 10 equiv.) was added to NMR tube. The progress was monitored by $^1$H NMR. See FIG. 33 for $^1$H NMR.

CIE NMR Experiments

10' (2.0 mg, 2.51 μmol, 0.03 equiv.) was dissolved in $C_6D_6$ (0.8 mL) and $^{13}$C labeled p-methoxy styrene 13'-$^{13}$C (11.2 mg, 83.6 μmol, 1.0 equiv.) was added followed by second olefin (styrene or 1-hexene, 1.0 equiv.). The solution was transferred to J. Young NMR tube and $^1$H NMR was checked after 16 hours at 80° C. See FIG. 34 for $^1$H and $^{13}$C NMR.

Figure 35A:
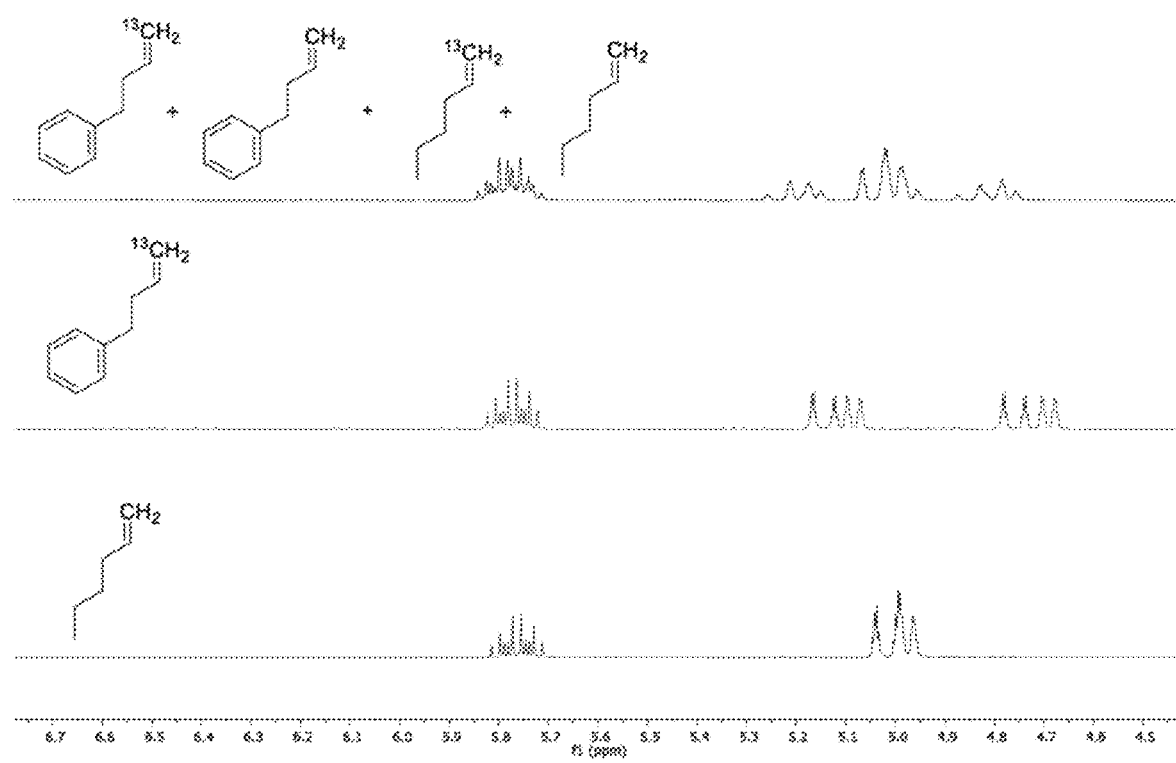
FIG. 35A shows fragments of $^1$H NMR spectrum of CIE of 9'-$^{13}$C with hexene-1 (C$_6$D$_6$, 400 MHz, 24° C.).
Figure 35B:
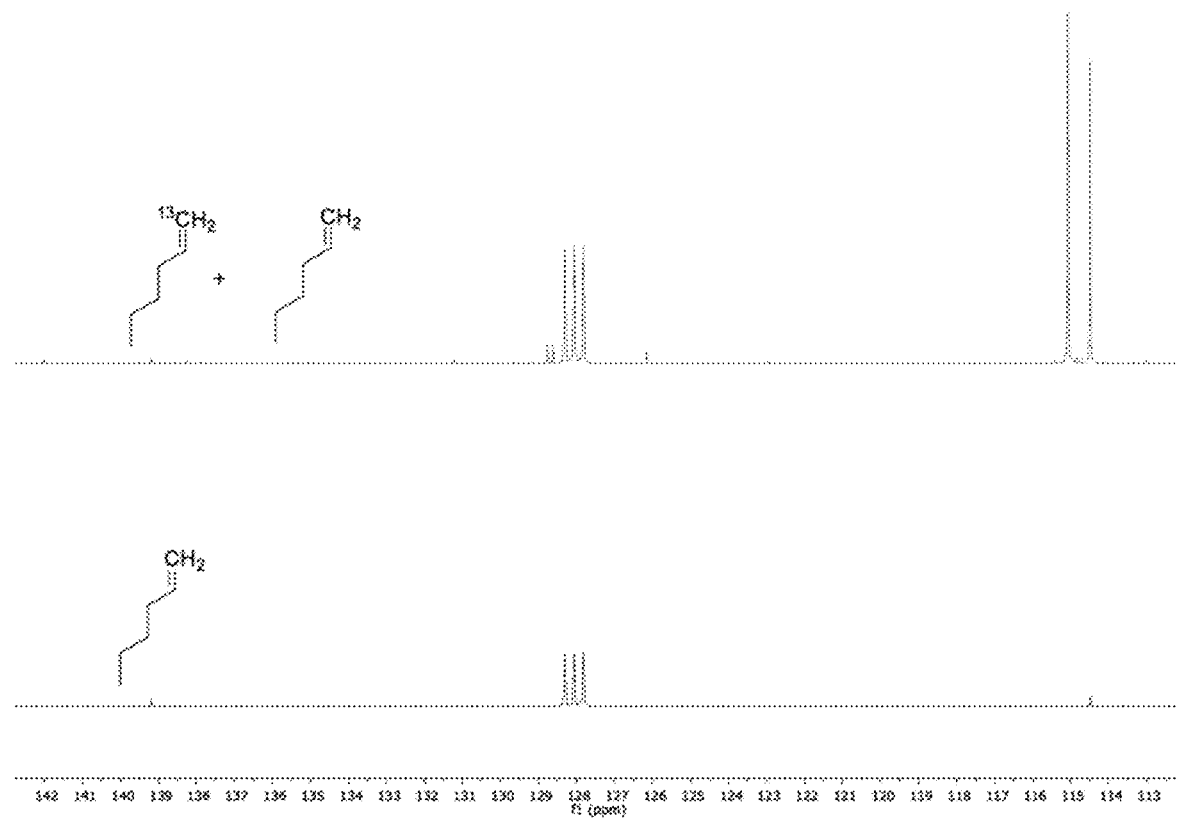
FIG. 35B shows fragment of $^{13}$C NMR spectrum of CIE of 9'-$^{13}$C with hexene-1 (C$_6$D$_6$, 400 MHz, 24° C.).

10' (8.0 mg, 10.0 μmol, 0.03 equiv.) was dissolved in $C_6D_6$ (0.8 mL) and 9'-$^{13}$C (44.2 mg, 334.4 μmol, 1.0 equiv.) was added followed by 1-hexene (41.8 μL, 334.4 μmol, 1.0 equiv.). The solution was transferred to J. Young NMR tube and $^1$H and $^{13}$C NMR was checked after ~72 hours at room temperature. See FIG. 35 for $^1$H and $^3$C NMR. To assess the amount of isotope exchange signals in $^{13}$C spectrum were integrated compared to $CH_2$-vinyl group.

Carbon Isotope Exchange Involving Methyl Group

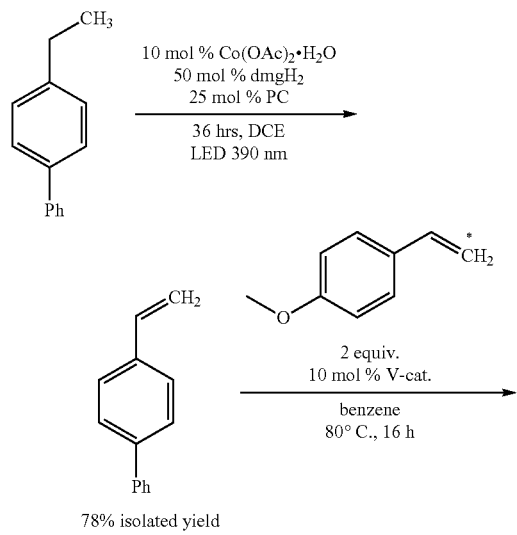

Scheme 7. CIE involving methyl group.

Step 1. Dehydrogenation: In the glovebox, a vial equipped with a stir bar was added 4-ethyl-1,1'-biphenyl (90.00 mg, 0.493 mmol, 1.00 equiv.), 2-chloroanthraquinone PC (6.10 mg, 0.025 mmol, 0.05 equiv.), Co(OAc)$_2$·4H$_2$O (12.30 mg, 0.050 mmol, 0.10 equiv.), dimethylglyoxime dmgH$_2$ (28.67 mg, 0.247 mmol, 0.50 equiv.), and dichloroethane (40 mL). The reaction mixture was sealed and stirred under 390 nm irradiation for 36 hours. After that, the solvent of the reaction mixture was removed on a rotary evaporator under reduced pressure, and the residue was purified by silica gel column chromatography in hexane to obtain 4-vinyl-1,1'-biphenyl as a white solid. (69 mg, 78% yield).

Figure 36:
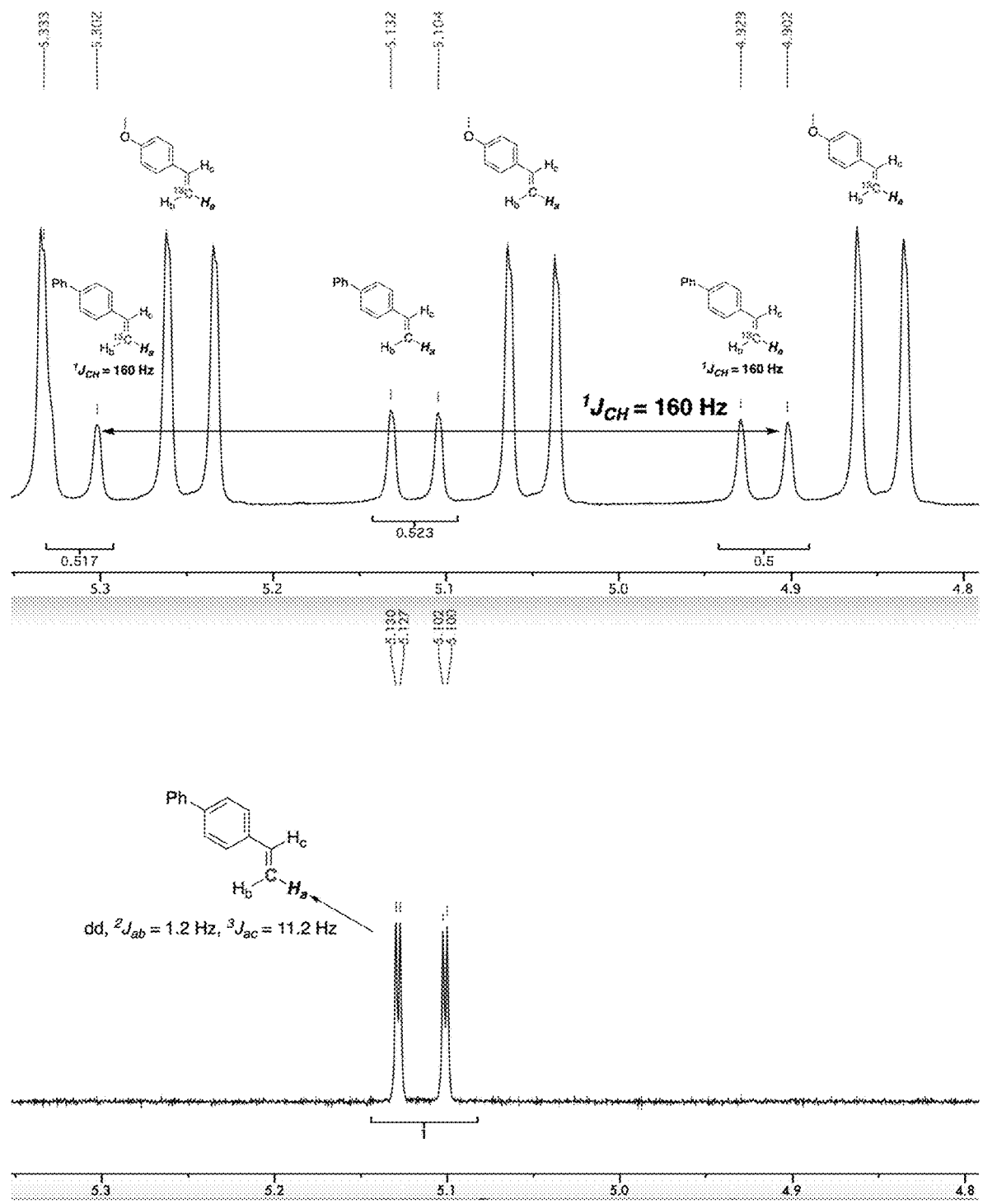
FIG. 36 shows fragments of $^1$H NMR spectrum of CIE of 10' with $^{13}$C-4-methoxystyrene in C$_6$D$_6$.

Step 2. Carbon Isotope Exchange: In the glovebox, 4-vinyl-1,1'-biphenyl (20.0 mg, 0.111 mmol, 1.0 equiv.), $^{13}$C-4-methoxystyrene (30.0 mg, 0.222 mmol, 2.0 equiv.), and VO(CHSiMe$_3$)(IMes)$_2$Cl V-cat. (8.9 mg, 0.011 mmol, 0.1 equiv.) were dissolved in 1.0 ml of $C_6D_6$. The solution was placed in a J. Young NMR tube, sealed, and heated at 80° C. for 12 hours. After that, $^1$H and $^{13}$C NMR were taken. 65% of carbon exchange was confirmed by $^1$H NMR (see FIG. 36).

Step 3. Hydrogenation: Under air, the solution from the previous step was transferred to a round bottom flask equipped with a magnetic stirring bar. 2 mg of Pd/C was added to the solution, and the flask was closed with a septum. A balloon filled with hydrogen was connected to the flask via a needle. The reaction mixture was stirred under a hydrogen atmosphere at 22° C. for 16 hours. The reaction mixture was filtered through a pad of silica and washed with benzene. The solvent of the reaction mixture was removed on a rotary evaporator under reduced pressure. The $^{13}$C enrichment was confirmed by $^1$H NMR.

Example 1—Synthesis of V Oxo Trialkyl Complex

The synthesis of V oxo alkylidene from the corresponding trialkyloxovanadium complex seems straightforward in analogy to V imido complexes. However, complex 12 (Scheme 8) is not readily available. Unlike the reaction of 1 with 2 or 3 (Scheme 9), direct alkylation of 10 leads to the reduction and formation of V(IV) complex 11.

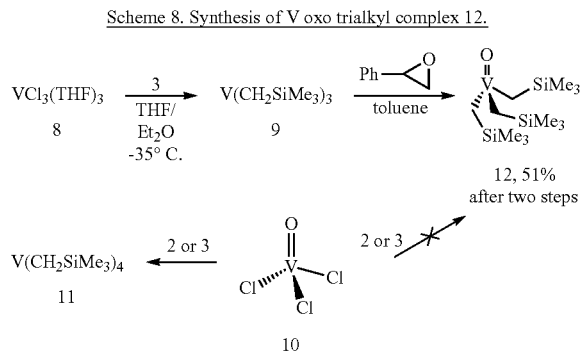

Scheme 8. Synthesis of V oxo trialkyl complex 12.

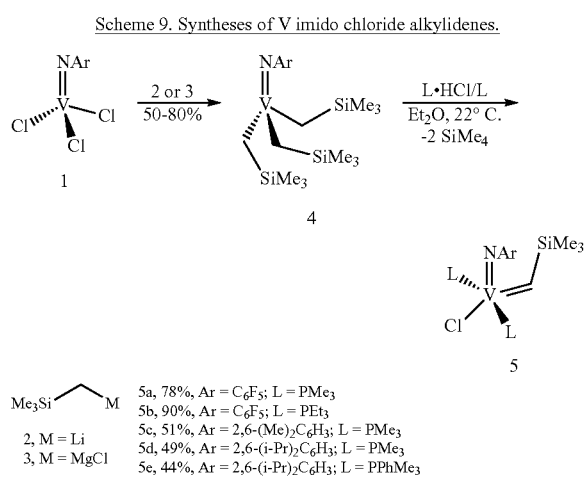

Scheme 9. Syntheses of V imido chloride alkylidenes.

Eventually, a procedure for the preparation of (t-BuCH$_2$)$_3$VO was adapted. Alkylation of 8 with 3 produced 9, which was used for the next step immediately due to the limited stability. The latter can be oxidized by several reagents, and styrene oxide was found to give the highest yield of 12.

Example 2—Synthesis of Oxo Alkylidene Complexes

With the complex 12 in hand, optimized conditions were tried to prepare V alkylidenes. Unfortunately, this mostly led to the decomposition of staring material into unidentified paramagnetic compounds. However, a small amount of desired alkylidene complex was observed by $^1$H NMR (the presence of V=C$\underline{\text{H}}$ signal, 16.07 ppm, C$_6$D$_6$). After considerable optimization, which included searching for appropriate phosphine and anionic ligands, solvent, and a proton source, optimal reaction conditions were found.

Treatment of 12 with PEt$_3$·TfOH in the presence of five equivalents of PEt$_3$ in CH$_2$Cl$_2$ resulted in two V alkylidenes 13 and 14 observed by $^1$H NMR (Scheme 10). Initially, it was proposed that a mixture of syn and anti-alkylidenes were formed. However, the ratio of two products varied from one experiment to another. Compound 14 was crystallized and undergone X-ray studies. Surprisingly, the isolated complex contained chloride ligand instead of triflate. Complex 13 can be quickly converted to 14 by adding a Cl$^-$ source, such as BnNEt$_3$Cl. Formation of complex 14 can be explained by slow release of Cl$^-$ by the reaction of CH$_2$Cl$_2$ and PEt$_3$.

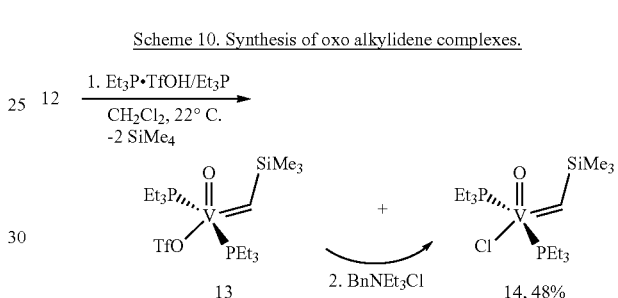

Scheme 10. Synthesis of oxo alkylidene complexes.

Example 3—Mechanism of the Formation of V Oxo Alkylidenes

The mechanism of the formation of V oxo alkylidenes includes protonation of one of three alkyl groups with acid (HX) to form 15 (Scheme 11). The second critical step of the alkylidene formation is the α-hydrogen abstraction induced by the coordination of the L-type ligand. The nature of the X group plays a crucial role in alkylidene formation. Some imido V complexes (Ar'O—V(NAr)(CH$_2$TMS)$_2$) are isolable and can be converted to alkylidenes upon the addition of PMe$_3$. In contrast, isolable Ph$_3$SiO—VO(CH$_2$TMS)$_2$ (15a) complex does not react with neutral ligands to form V oxo alkylidene. 15b has limited stability in solution. Still, it can react with neutral ligands to form alkylidenes 16. In the case of 15c, the rate of decomposition is higher than alkylidene formation.

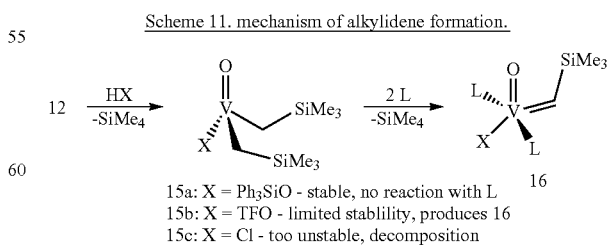

Scheme 11. mechanism of alkylidene formation.

Complex 14 is a mixture of syn and anti-alkylidenes in the ratio 97:3 in the solution by $^1$H NMR (C$_6$D$_6$). An X-ray structural study showed that syn-14 has a distorted trigonal bipyramidal geometry with phosphines in axial positions [V-P1 2.4884(8) Å, V-P2 2.4701(8) Å, P1-V-P2 164.89(2)°]. The V1-C1 distance is 1.8403(19) A and V1-O1 bond is 1.6079(15) A, that are similar to reported V oxo alkylidene. The large V=C—Si angle (140.01(12)°) is indicative of α-hydrogen agostic interactions with V center.

Example 4—Metathesis Activity of 14

The metathesis activity of 14 was explored with diallyl N-tosylamide 17 and its reactivity was compared with V imido complex 5b (entry 1 and 2, Table 2). Catalyst 14 outperforms 5b in reaction with 17. Notably, conversion to 18 is higher in an open vial in both cases, suggesting that the active species are sensitive to ethylene.

TABLE 2

RCM catalyzed by 14 and 5b.

17, Ts = p-CH$_3$C$_6$H$_4$SO$_2$ → catalyst 22° C., 24 h, open vial → 18 + ethylene

| # | cat. | solvent | cat, mol% | conv., %[a] | TON |
|---|------|---------|-----------|-------------|------|
| 1 | 5b | benzene | 5 | 63 (42)[b] | 12.6 |
| 2 | 14 | benzene | 5 | 87 (67)[b] | 17.4 |
| 3 | 14 | chloroform | 1 | 59 (56)[b] | 59.0 |
| 4 | 14 | chloroform | 2 | 83 (66)[b] | 41.5 |
| 5 | 14 | chloroform | 3 | 91 (69)[b] | 30.3 |
| 6 | 14 | chloroform | 4 | 94 (73)[b] | 23.5 |
| 7 | 14 | chloroform | 5 | 96 (76)[b] | 19.2 |
| 8 | 14 | chloroform | 6 | 97 (76)[b] | 16.2 |

[a] by $^1$H NMR.
[b] closed vial.

To investigate the mechanism of catalyst deactivation, a reaction of 14 with ethylene was conducted. Initially, the formation of a small amount of new alkylidene signal (m, 13.8 ppm, C$_6$D$_6$, presumably V methylidene) and vinyl-TMS was observed. After several hours at room temperature, the complete decomposition of alkylidenes was observed. The reaction of 14 with ethylene produces only traces of propylene by $^1$H NMR, which is in contrast to the analogous reaction of 5b, where propylene is the primary decomposition product.

To examine the contribution of bimolecular decomposition in the deactivation of the catalysts, the reaction of 14 with 17 was tested at different catalysts loadings (entries 3-8, Table 2). Important to mention, reactions were performed in chloroform since it gives the highest conversion among tested solvents. The decrease of the catalyst loading led to an increase of TON, suggesting that bimolecular decomposition plays a role in the catalyst deactivation. Noteworthy, the TON of 59 is the highest TON for V-based OM involving terminal olefins.

Figure 11:
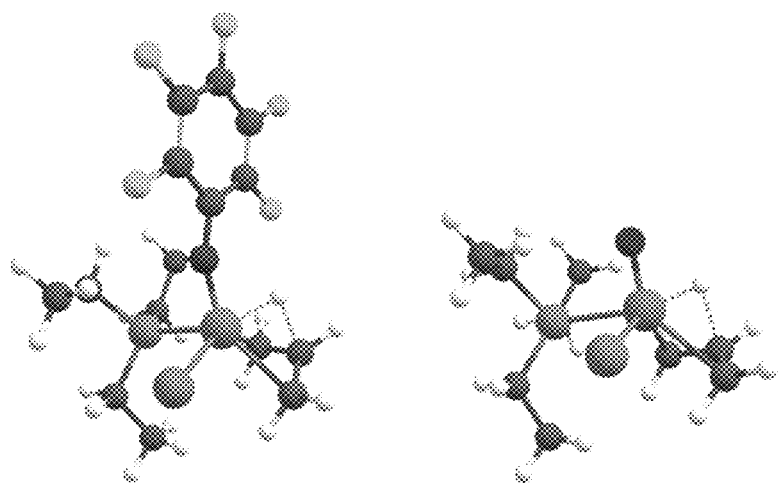
FIG. 11 shows Optimized structures (left: V imido; right: V oxo) for the β-H elimination transition states.

Mononuclear catalyst deactivation occurs through β-H elimination from MCB. This step has the highest energy barrier similar to other d$^0$ complexes. The β-H elimination transition state is 31.1 and 26.1 kcal mol$^{-1}$ above initial reactants for 14 and 5b, which agrees with the experimentally observed larger stability toward ethylene of V oxo complex. The β-H transfer imposes the allyl fragment almost trans to the oxo or imido ligand (FIG. 11), and this causes a strong trans influence between the two groups. Since the oxo acts as a stronger σ-donating ligand than the imido, the destabilization of the β-H transition state is more significant for 14, hindering its deactivation. The computed energy barriers are consistent with the deactivation taking place in a few hours for 5b and a few days for 14, suggesting that other deactivation processes, such as bimolecular decomposition, are important for 14.

The results show that V oxo alkylidene 14, the active catalysts for olefin metathesis, can be prepared directly from VO(CH$_2$SiMe$_3$)$_3$ complex. Furthermore, experimental and computational studies strongly suggest that the β-H elimination from metallacyclobutane is significantly disfavored for V oxo species compared to V imido counterparts. As a result, catalyst 14 exhibits the highest reported productivity among known V alkylidenes in ring-closing metathesis of various terminal dienes due to the greater tolerance to ethylene. 14 is a reliable V-based olefin metathesis catalyst.

Example 5—Other V Catalysts

Figure 12A:
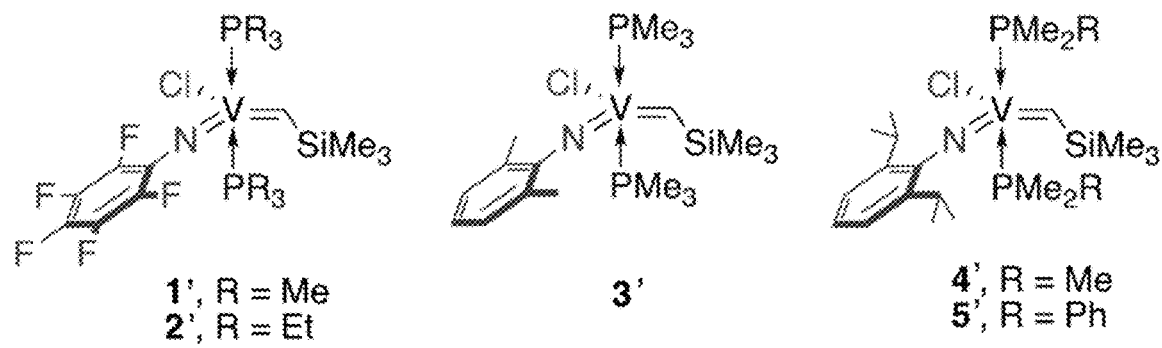
FIG. 12A shows examples of V imido phosphine catalysts.

V imido chloride phosphine alkylidenes (1'-5', FIG. 12A) have been synthesized in one step from readily available V trialkyl complexes utilizing α-H abstraction in the presence of phosphonium chlorides. Synthesized complexes are active OM catalysts. These complexes can be used in ring-closing metathesis (RCM). Also, V imido chloride alkylidenes tolerate multiple common functional groups, including ethers, tertiary amines and amides, and esters.

Figure 12B:
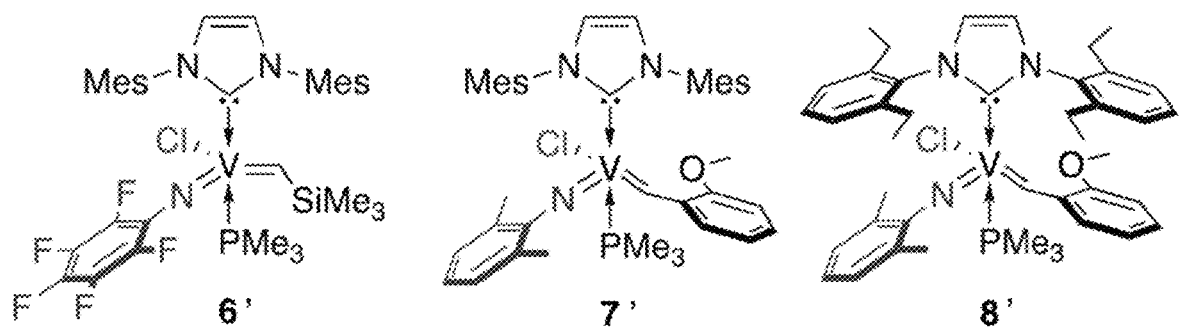
FIG. 12B shows examples of V imido NHC catalysts.

V imido N-heterocyclic carbene (NHC) chloride alkylidenes (6'-8', FIG. 12B) have also been synthesized. Complex 7' is the most effective catalyst among the studied, achieving a turnover number (TON) of 170 in reaction with 17 (FIG. 12C), the highest reported TON of V-based OM involving acyclic terminal olefins to date. Because CIE involves terminal olefins, the developed catalysts are excellent starting points for further productivity improvement.

Figure 12C:
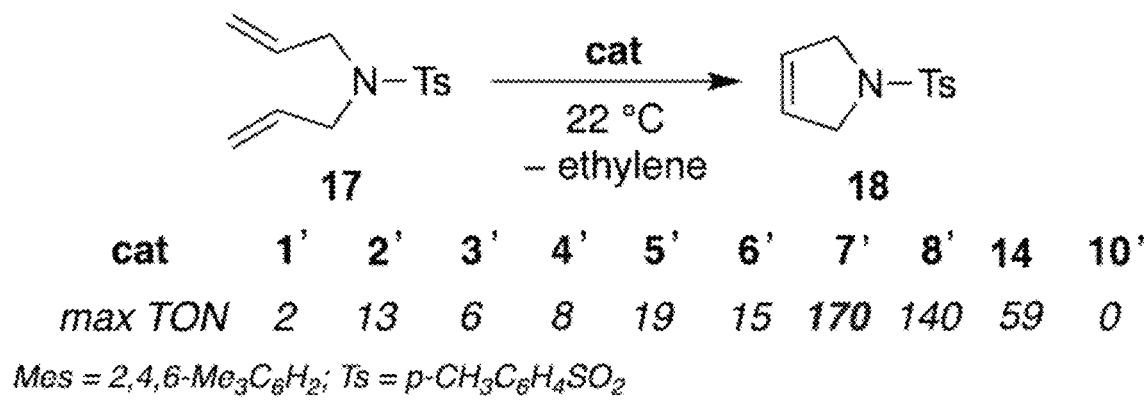
FIG. 12C shows the productivity in ring-closing metathesis of examples of V-based catalysts.
Figure 12D:
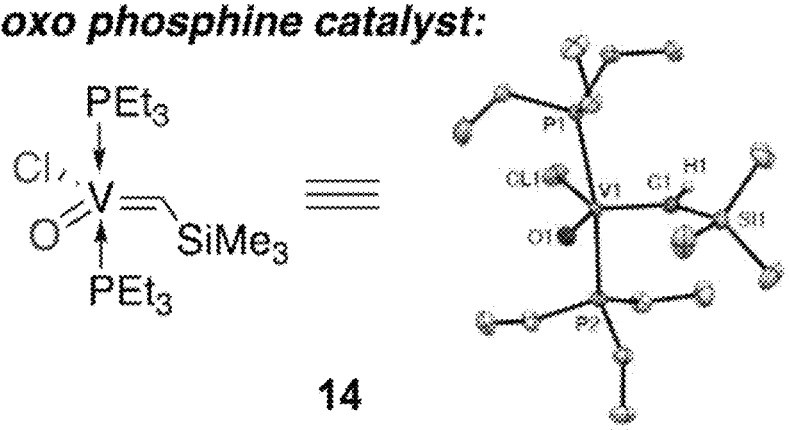
FIG. 12D shows a example of V oxo phosphine catalysts.
Figure 12E:
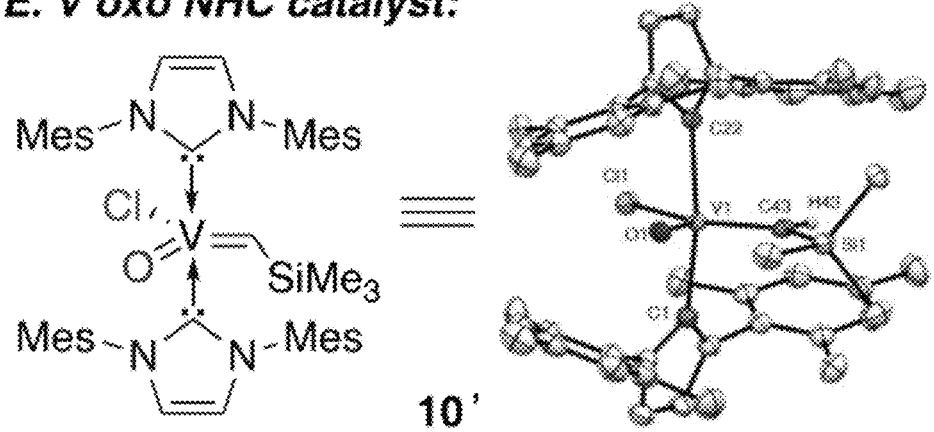
FIG. 12E shows a example of V NHC catalysts.

The catalytically active V oxo phosphine alkylidene 14 (FIG. 12D), its X-ray structure, activity in RCM of terminal olefins, and functional group tolerance have been discussed above. V oxo phosphine complex 14 outperforms its imido phosphine counterparts 1'-5' in RCM reactions involving terminal olefins (FIG. 12C). However, the relatively small oxo ligand can bridge two metal centers and encourage bimolecular decomposition, the primary degradation pathway for V oxo complex 14. To overcome this challenge, a large NHC ligand was introduced to obtain the V oxo NHC complex 10' (FIG. 12E). Complex 10' is inactive in the RCM reaction of 17 due to the high preference for degenerate metathesis (exchange of methylene groups).

Catalyst activity (turnover frequency, TOF) is essential for achieving equilibrium in a short time, preferably within minutes. The crucial factors that affect the TOF of active V catalysts are studied by varying neutral ligands (phosphines, NHCs, nitriles, and amines), imido (aryl/alkyl) and oxo groups, and anionic ligands (halides, pseudohalides, alkoxides) to tune the steric and electronic properties of metal center to study their influence on the activation barrier of each step of the catalytic cycle. In addition, decomposition studies are focused to find an optimal ligand set around V to increase the productivity (TON) and stability of V complexes to create robust and reliable catalysts.

Figure 12F:
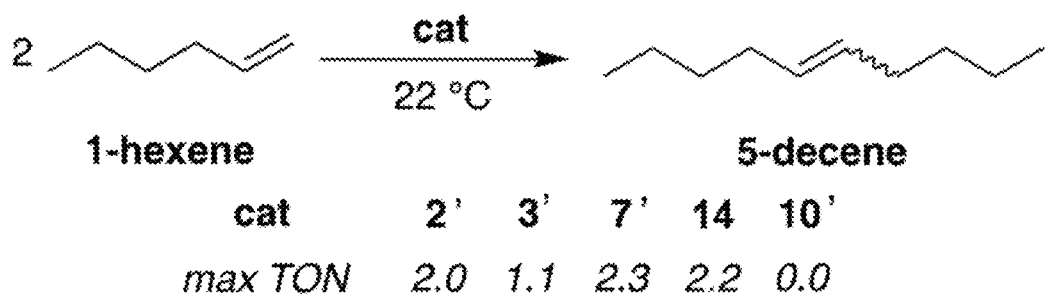
FIG. 12F shows the productivity in cross-metathesis of examples of V-based catalysts.
Figure 12G:
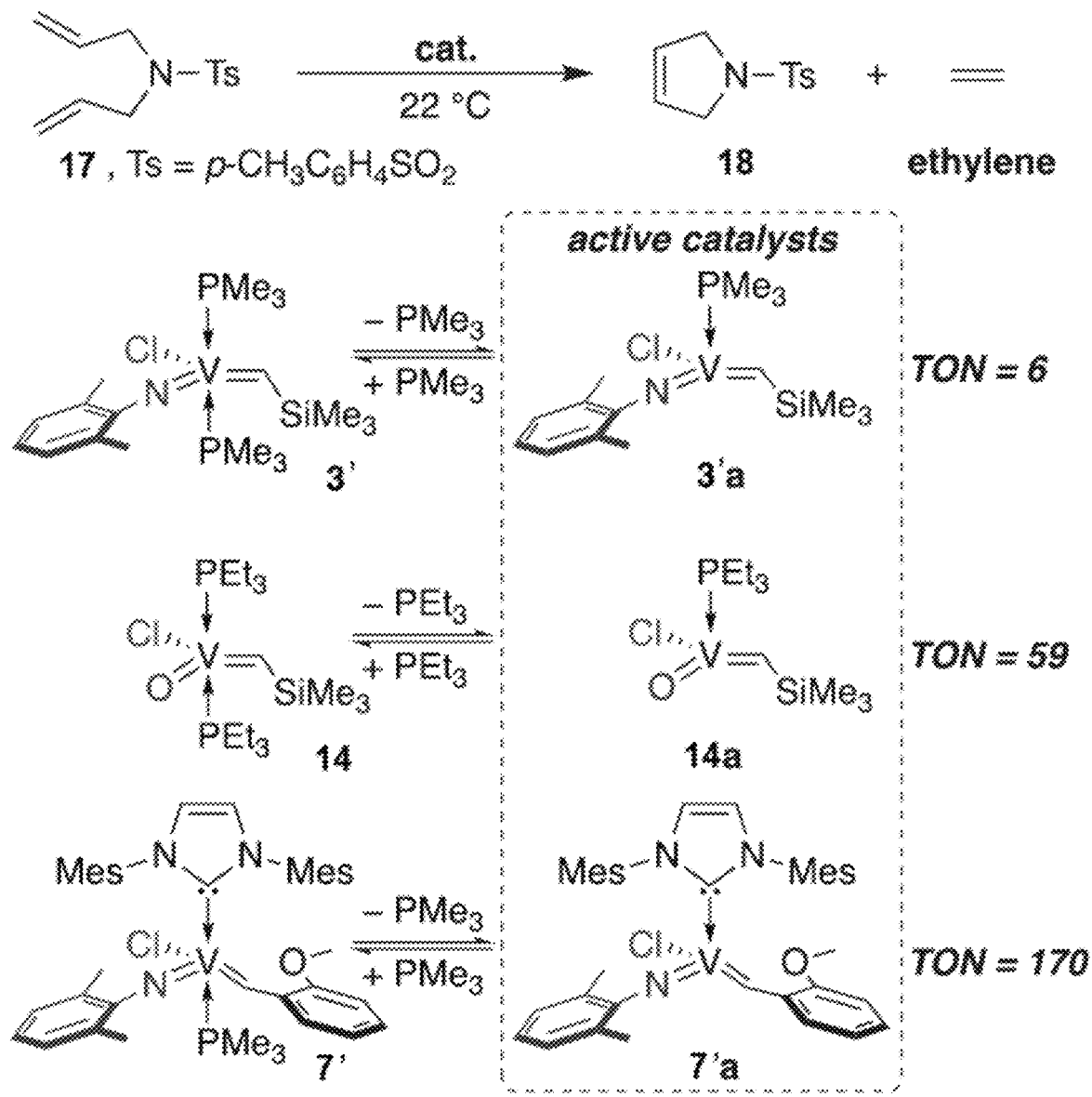
FIG. 12G shows maximum Turnover Numbers (TONs) for Synthesized V Catalysts in the model RCM reaction.

Representative V alkylidene complexes 3', 14, 7' and their productivities (turnover numbers, TONs) in RCM involving the model substrate 17 are shown in FIG. 12G. The dissociation of one neutral ligand is required to access four-coordinate 14-electron active catalysts 3'a, 14a and 7'a during the reaction. Catalyst 3' exhibits a low RCM productivity with 17 due to limited stability toward ethylene. The main decomposition pathway involves the β-hydride (β-H) elimination at an unsubstituted metallacyclobutane (MCB) formed during the catalysis. Substitution of an imido group to oxo significantly disfavors β-H elimination, leading to a higher RCM productivity with catalyst 14. However, the bimolecular decomposition of V oxo phosphine alkylidenes becomes the primary reason for catalyst degradation. Exchange of phosphine in imido complex 3' to an N-heterocyclic carbene (NHC) ligand increases the TON from 6 to 170 in the reaction with 17 by suppressing both β-H elimination from MCB and bimolecular decomposition. The main degradation pathway for catalysts 7' is the exchange of NHC to phosphine that forms during the initiation step, leading to a bis phosphine complex analogous to 3', which is unstable toward ethylene.

To preserve remarkable stability toward β-H elimination of V oxo complexes and disfavor bimolecular decomposition, V oxo NHC alkylidenes were synthesized by introducing a large NHC ligand. The shift to phosphine-free V oxo alkylidenes would improve catalyst performance, since phosphines can participate in side reactions and deactivation pathways, such as reduction of high-oxidation-state V complexes and reaction with alkylidenes.

Complex 10' has been synthesized in 78% yield from 14 and 2 equiv of IMes utilizing a ligand exchange reaction (Scheme 12).

Surprisingly, complex 10' does not exhibit RCM activity with 17. It is possible that one NHC ligand does not dissociate readily to form a four-coordinate 14-electron active catalyst. To overcome this challenge, V oxo NHC complexes was synthesized bearing bulky alkoxide ligands to facilitate the dissociation of one NHC. Screening various alkoxides (e.g.,

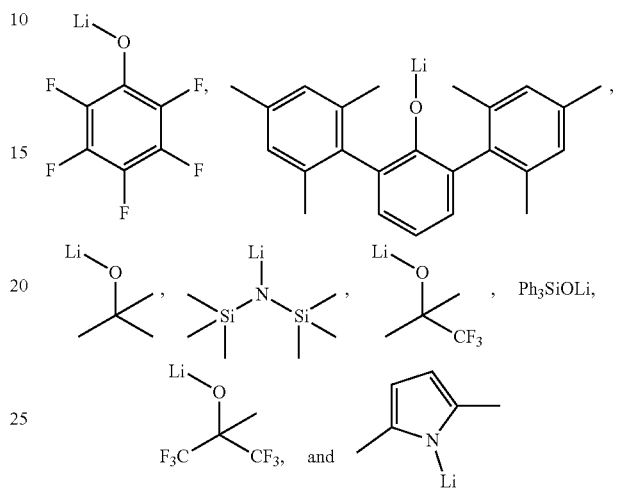

) led to the synthesis and isolation of complex 11' in 89% yield (Scheme 13).

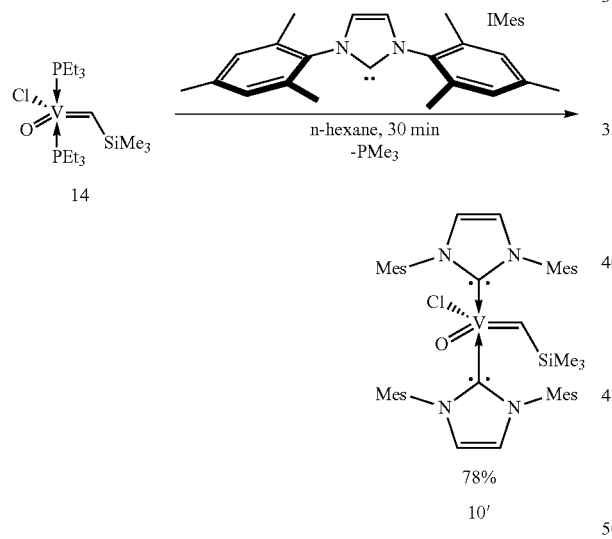

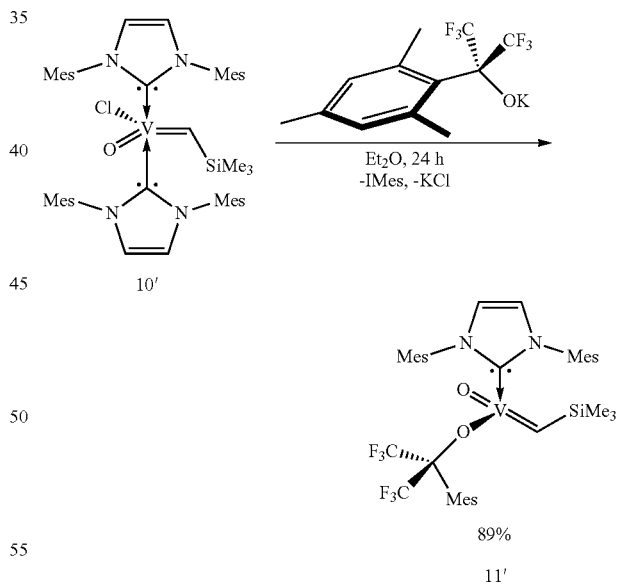

A 1H NMR spectrum of 10' in $C_6D_6$ showed that the alkylidene proton resonance is a singlet at 14.45 ppm ($^1J_{CH}$=114 Hz). An X-ray structural study revealed that 10' is a syn isomer (FIG. 12E) and has a distorted-trigonal-bipyramidal geometry with NHCs in axial positions (V1-C1 2.173(2) Å, V1-C22 2.191(2) Å, C11-V1-C22 156.52(10)°), which is similar to that of the imido NHC complex 7' (V—C(NHC) 2.1828(11) Å and P-V1-C(NHC) 154.52(3)°). The V1-C43 distance is 1.889(3) Å, and the V1-O1 bond length is 1.586(2) Å, which are similar to those in 14. It is worth noting that the V=C—Si angle (133.01(15)°) is lower than the V=C—Si angle in 14 (140.03(9)°). This can be explained by less extent of an α-hydrogen agostic interaction with the metal center due to the lower electrophilicity of V in 10' resulting from the high σ-donating abilities of two NHC ligands.

Figure 12H:
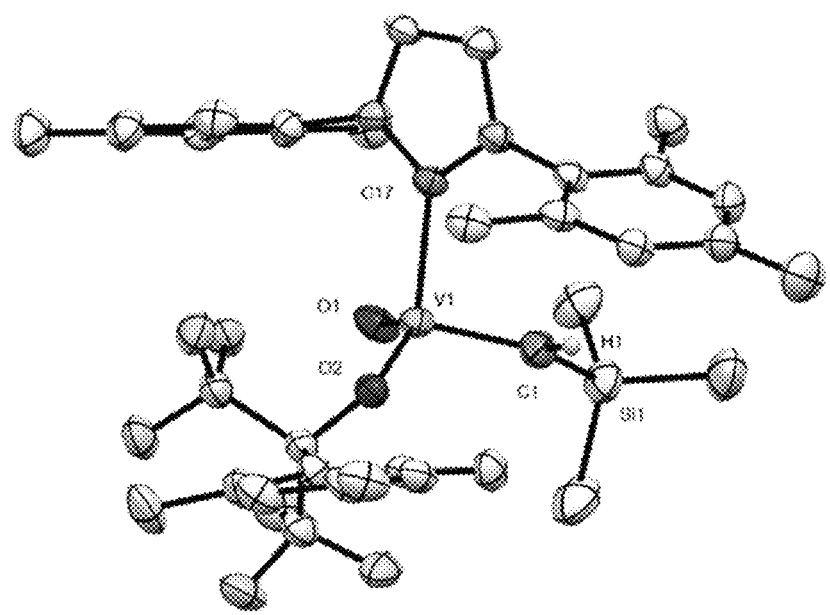
FIG. 12H shows perspective view of the crystal structure of complex 11' with thermal ellipsoids shown at 30% probability.

The proton NMR spectrum of complex 11' in $C_6D_6$ revealed a singlet resonance for the alkylidene proton at 17.66 ppm ($^1J_{CH}$=112 Hz). X-ray studies showed that 11' is a four-coordinate complex (syn isomer) with a distorted-tetrahedral geometry (FIG. 12H). Four-coordinate V alkylidenes are rare. Complex 11' is the first crystallographically characterized four-coordinate V alkylidene that contains oxo or alkoxide ligands. The relevant bond distances are V1-C1=1.853(10) Å, V1-C17=2.140(7) Å, V1-O1=1.588(5) Å, and V1-O2=1.845(5) Å. The V=C—Si angle is 130.5(5)°, and the V1-O2-C angle is 145.9(5)°.

Figure 13:
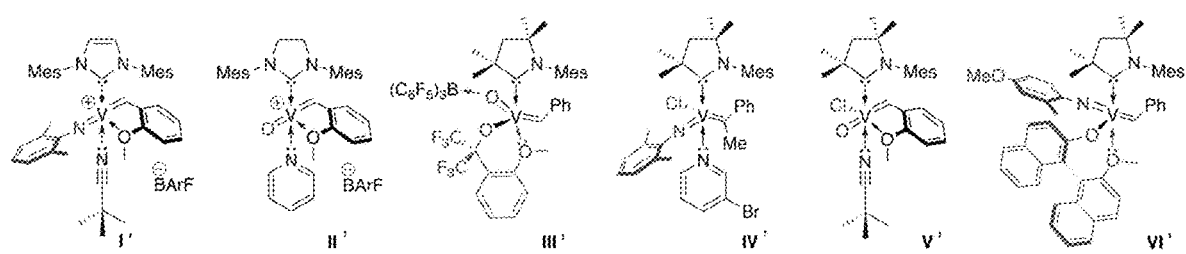
FIG. 13 shows additional V-based catalysts.

Other representative V complexes are shown in FIG. 13. Cationic Mo and W alkylidenes are among the most active OM catalysts. Some of them are air-stable and exhibit remarkable functional group tolerance. Cationic V alkylidene complexes (I' and II') contain two neutral ligands. Increased electrophilicity of a cationic metal center can improve reactivity toward sterically hindered (disubstituted terminal olefins) and electron-deficient olefins. Air-stability and functional group tolerance are evaluated. Another approach that is utilized to increase the electrophilicity of the metal center in V oxo complexes is a coordination of a Lewis acid to oxo ligand (III'). It has been shown that the coordination of $B(C_5F_6)_3$ to oxo ligand can improve the activity of the OM catalysts. Coordination of a Lewis acid lowers the oxo ligand's donor ability to the metal, increases electrophilicity of the metal center, and results in higher OM activity.

Also, the disubstituted V alkylidenes (IV') is synthesized for exploring the transfer of =$CH_2$ fragment to disubstituted terminal olefins. The chelating strategy is utilized to increase the activity and stability of V catalysts (I', II', III', V', and VI').

Figure 14:
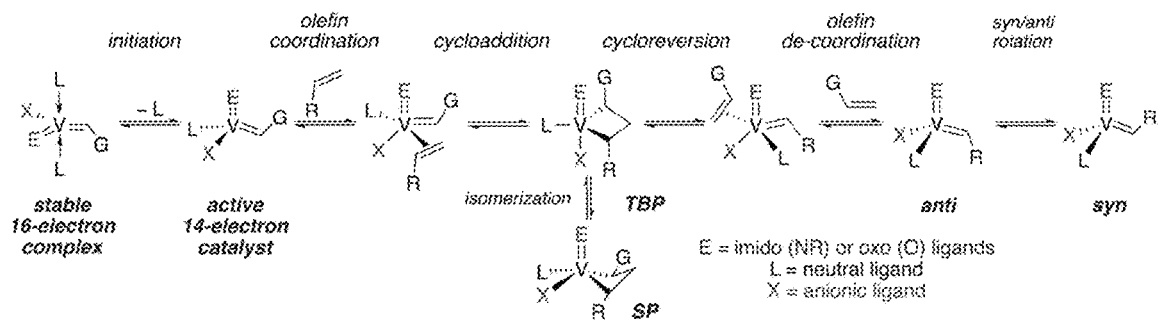
FIG. 14 shows distinctive steps in V-based olefin metathesis.

All steps of V-based OM shown in FIG. 14 are studied for the design of efficient and reliable catalysts by integration of experiments with theoretical research efforts. The study of the intrinsic activity of V-based catalysts is important. Kinetic studies are performed for 4-coordinated active catalysts in the presence of substrates. An essential aspect of the catalyst design is the evaluation of decomposition pathways. Those studies lead to the necessary catalyst modifications to increase TON and functional group tolerance. Decomposition products are isolated, and their structures are determined by X-ray crystallography.

Noteworthy, V MCBs have never been observed. Spectroscopic observation of $^{13}C$ labeled V MCB (TBP, SP, or both) by NMR at low temperature is a breakthrough achievement in the field and is essential from a fundamental standpoint for comparison with known MCBs of Mo, W, Ru, and Re. Interconversions between labeled methylidene/MCB (TBP), TBP/SP, and syn/anti isomers at different temperatures by VT NMR make it possible to experimentally determine the rates and activation parameters of cycloaddition/cycloreversion and TBP/SP steps for V catalysts.

Example 6—Carbon Isotope Exchange

Figure 15:
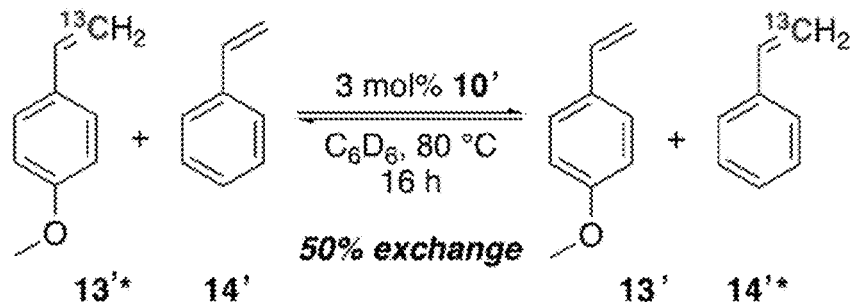
FIG. 15 shows a representative CIE.

Complexes 1'-8', 10' and 14 have limited activity in cross-metathesis (CM) of 1-hexene (FIG. 12F). This supports the preferential formation of 1,3-MCB for V alkylidenes in reaction with terminal olefins. The higher reactivity of complexes 1'-8' and 14 toward dienes can be explained by the intramolecular formation of 1,2-MCB. Exceptional preference for degenerate metathesis for 10' has been confirmed computationally and experimentally. Thus, CIE occurs between terminal olefins using $^{13}C$-labeled compounds that have been prepared from commercially available $^{13}CH_3I$ and aldehydes utilizing the Wittig reaction. Representative CIE between 13'* and styrene 14' is shown in FIG. 15. 50% isotope exchange is achieved as expected at equilibrium conditions (assuming no isotope effect).

Figure 16:
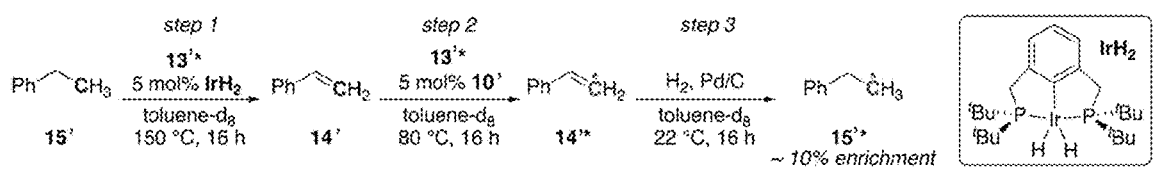
FIG. 16 shows a model tandem alkane dehydrogenation/olefin metathesis.

Alkane dehydrogenation/olefin metathesis strategy involving ethylbenzene 15' and 13'* as model substrates was tested in the presence of 5 mol % of $IrH_2$ and 10' (FIG. 16). Alkane dehydrogenation is a highly endothermic process and requires high temperatures (>125° C.). Complex 10' decomposes at temperatures above 120° C. To overcome this challenge, the one-pot sequential alkane dehydrogenation—olefin metathesis—hydrogenation approach was performed. First, 15' and 13'* were heated in the presence of 5 mol % of $IrH_2$ at 150° C. for 16 hours to obtain 14'. Then 5 mol % of 10' was added, followed by heating the reaction mixture at 80° C. for 16 hours to form 14'*. Finally, the reaction mixture was exposed to $H_2$ in the presence of Pd/C at 22° C. to produce 15'*. ~10% $^{13}C$-enrichment of 15' can be observed by NMR. However, GCMS studies are required to quantify the enrichment precisely.

Although the reaction involves three steps, there is no need for the isolation of intermediates, which will be essential for reactions involving radioactive materials. Noteworthy, a high percentage of isotope enrichment is unnecessary for ADME studies. Thus, clinical and preclinical radiolabeling studies require $^{14}C$ specific activity of ~20 µCi/mg, corresponding to 10-20% of $^{14}C$ enrichment of target compounds depending on MW.

The results show that a highly polarized V=C bond enables high regioselectivity in the formation of metallacyclobutane, leading to an efficient transfer of isotopically labeled =*$CH_2$ group between terminal olefins. In combination with the dehydrogenation reaction, CIE involving the methyl group was presented. The introduced V-catalyzed carbon isotope exchange serves as a new platform to incorporate labeled carbon atoms into a wide range of bioactive molecules without developing new multi-step synthetic strategies.

Figure 17:
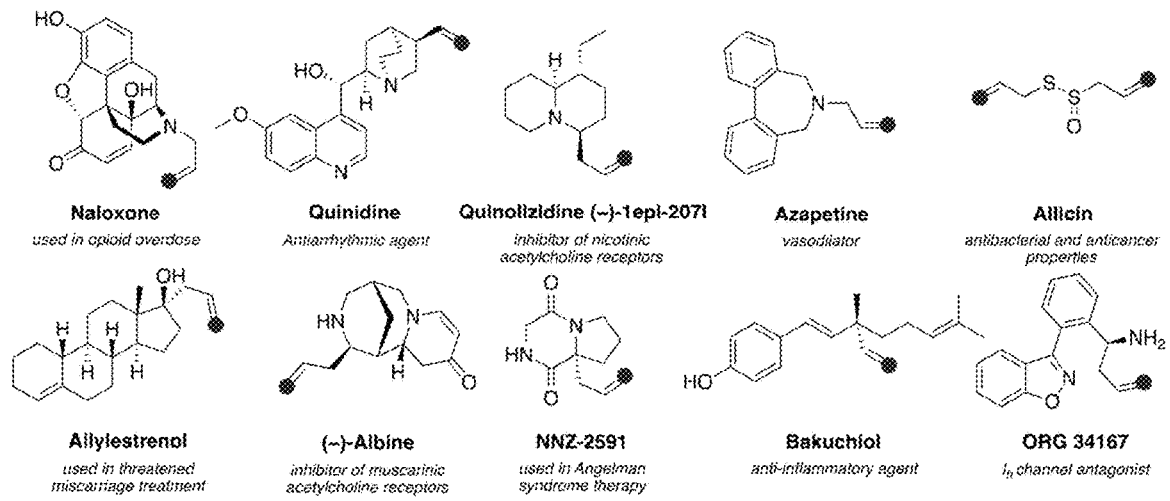
FIG. 17 shows selected biologically active compounds for CIE through the transfer of terminal CH$_2$ moiety.

The utility of the developed V catalysts is demonstrated through application to a concise synthesis of isotopically labeled biologically active molecules containing terminal olefins, including naloxone, quinidine, quinolizidine (−)-1epi-207I, azapetine, allicin, allylestrenol, (−)-albine, NNZ-2591, bakuchiol, and ORG 34167 (FIG. 17).

V-based OM catalysts can tolerate many functional groups present in selected target molecules, such as ethers, thioethers, tertiary amines, amides, and common heterocycles quinoline and isoxazole. Traditional and traceless protecting strategies can be used for compounds containing OH- and NH-groups. Noteworthy, catalyst 10' has limited activity toward 1,2-disubstituted and trisubstituted olefins. Therefore, only the terminal $CH_2$ moiety will be affected by V-promoted CIE in the case of bakuchiol in reaction with 10'.

Alkenes are versatile compounds that can be converted to numerous functional groups present in bioactive compounds. Pharmaceuticals and natural products that have been made from precursors containing terminal =$CH_2$ group in a late stage of their synthesis can be targeted. Although the CIE is preferred on the target molecules, late-stage incorporation of labeled carbon atoms does not require the development of new multi-step synthetic strategies. Therefore, it is an attractive approach when other alternatives are limited.

Figure 18A:
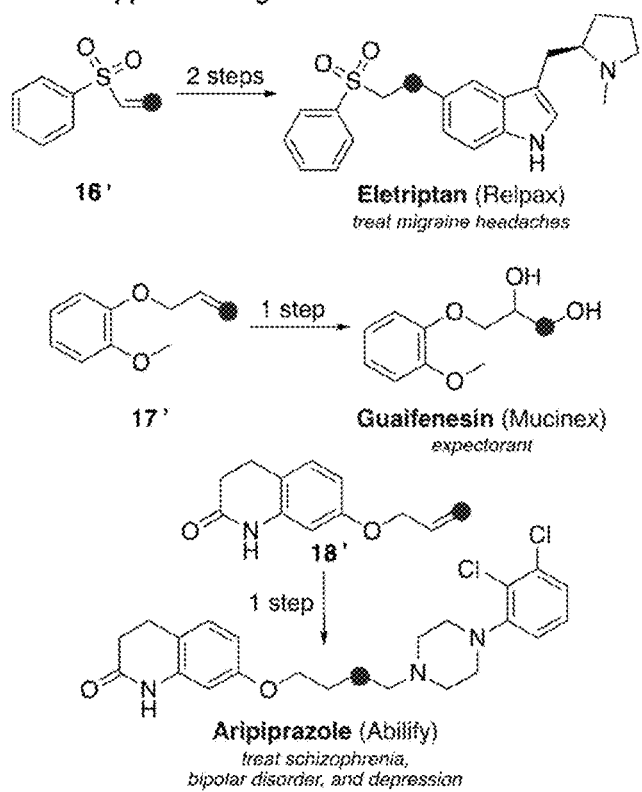
FIG. 18A shows selected FDA approved drugs for late-stage CIE.
Figure 18B:
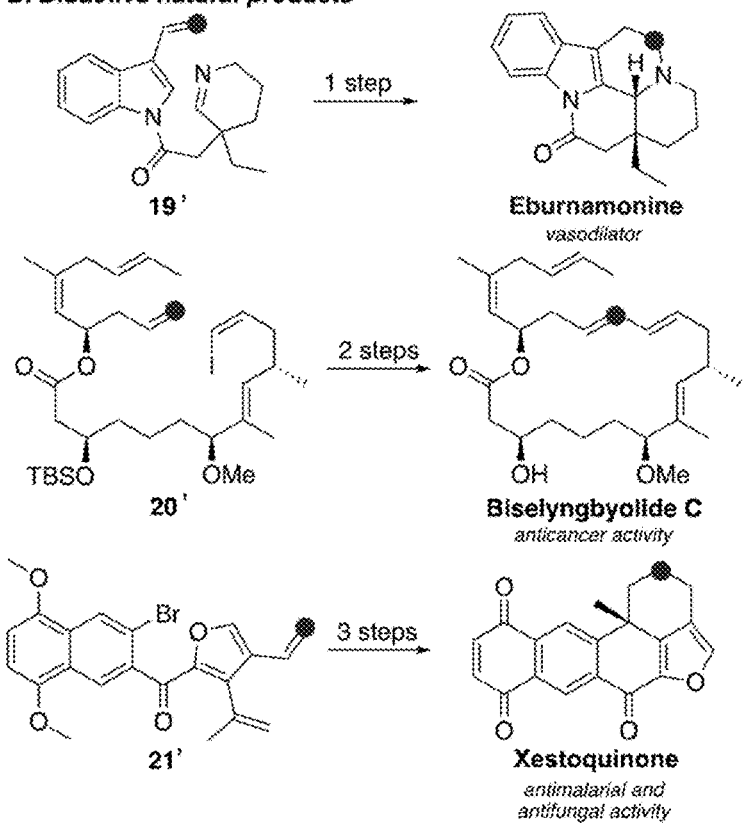
FIG. 18B shows selected biologically active compounds for late-stage CIE.

Selected biologically active compounds for late-stage CIE are shown in FIG. 18. Intermolecular Mizoroki-Heck reaction of 16' followed by deprotection step leads to eletriptan. Guaifenesin can be obtained by dihydroxylation of 17'. Rh-catalyzed hydroaminomethylation of 18' results in aripiprazole in one step. Intramolecular aza-Diels-Alder reaction will be used to obtain labeled eburnamonine from 19'. Intramolecular macrocyclization of 20' via Mizoroki-Heck reaction followed by deprotection leads to Biselyngbyolide C. Xestoquinone can be synthesized from 21' by cascade intramolecular Mizoroki-Heck reaction followed by reduction and oxidation sequence.

Figure 19:
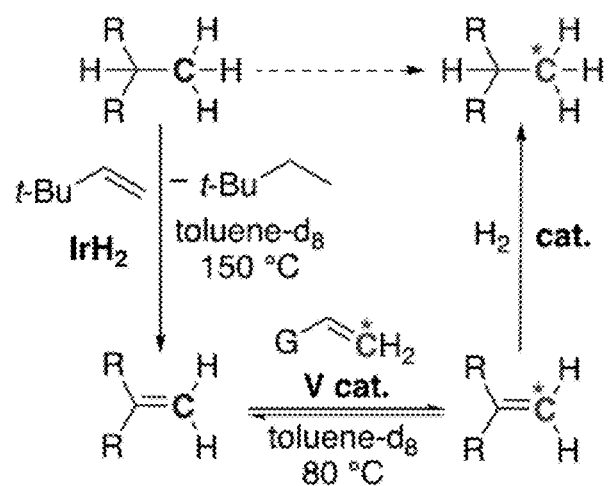
FIG. 19 shows a strategy of one-pot CIE.

CIE involving the methyl group has been shown above. To further optimize the procedure, a one-pot alkane dehydrogenation—olefin metathesis—hydrogenation sequence is utilized as shown in FIG. 19. Hydrogen acceptors such as t-BuCH=CH$_2$ or norbornene can be used, which will make the dehydrogenation step irreversible. Next, V catalyst and labeled terminal olefin are added to perform CIE. Finally, hydrogenation in the presence of hydrogen gas and appropriate catalyst completes the sequence. In accordance with the present invention, the present Ir-catalyst can serve as a hydrogenation catalyst. Alternatively, Ru or Co catalysts can be applied for selective hydrogenation of terminal olefins when other olefinic groups are present.

Figure 20:
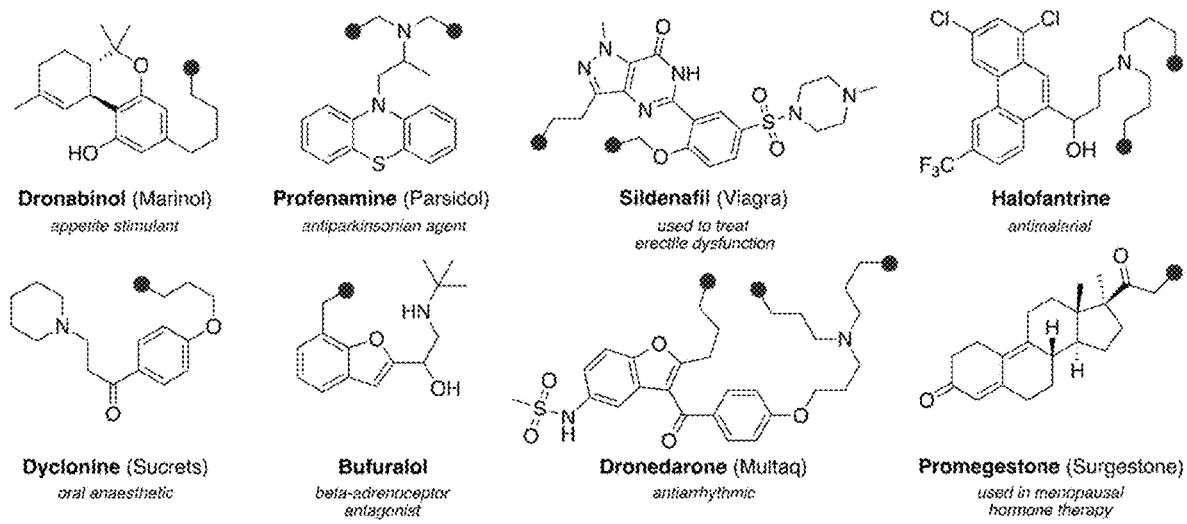
FIG. 20 shows selected pharmaceuticals for CIE utilizing tandem dehydrogenation/olefin metathesis strategy.

The utility of the instant method can be expanded to various isotopically labeled pharmaceuticals and natural products containing alkyl groups, including dronabinol, profenamine, sildenafil, halofantrine, dyclonine, bufuralol, dronedarone, and promegestone (FIG. 20). Traditional and traceless protecting strategies can be utilized for compounds containing OH- and NH-groups.

Example 7—Reactivity of Complexes 10' and 11'

An important feature of an oxo ligand is the ability to coordinate Lewis acids. It has been shown that the coordination of B(C$_6$F$_5$)$_3$ to a W oxo alkylidene can improve the activity and selectivity of the OM catalysts. However, adding B(C$_6$F$_5$)$_3$ to 10' in C$_6$D$_6$ led to the rapid decomposition of 10'. The reaction between B(C$_6$F$_5$)$_3$ and 11' resulted in the formation of a new alkylidene as shown by 1H NMR (singlet, 14.63 ppm, C$_6$D$_6$), presumably due to the coordination of B(C$_6$F$_5$)$_3$ to an oxo ligand followed by slow degradation of the 11'·B(C$_6$F$_5$)$_3$ adduct.

Complex 11' does not react with 17, 1,7-cyclooctadiene, 1-hexene, styrene, or ethylene at 22° C. However, 11' slowly catalyzes the RCM reaction of 17 and 1,7-cyclooctadiene and a CM reaction of 1-hexene at 100° C. (1-4 TON after 3-4 days). Heating of 11' in the presence of ethylene led to slow decomposition of 11'. The corresponding methylidene and MCBs have not been observed by NMR. It is believed that the bulky Mes(CF$_3$)$_2$CO alkoxide prevents the coordination of an olefin to the metal center, suppressing the catalytic activity.

Figure 21A:
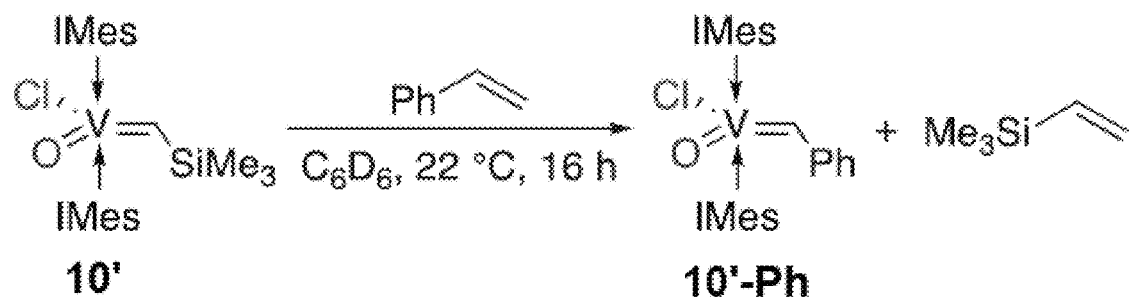
FIG. 21A shows reactivity of complex 10' in alkylidene exchange.
Figure 21B:
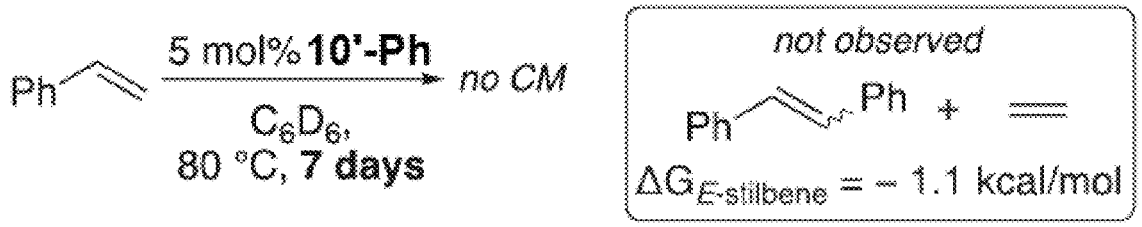
FIG. 21B shows reactivity of complex 10' in cross-metathesis.

Complex 10' does not catalyze the RCM of 17 or 1,7-cyclooctadiene and CM of 1-hexene or allylbenzene. However, 10' reacts with styrene to form V benzylidene complex 10'-Ph (FIG. 21A). The previously reported V imido alkylidene reacts with styrene to produce metallacyclopropane. 10'-Ph does not catalyze the RCM of 17 and the CM of 1-hexene or styrene. Thus, heating of 10'-Ph in the presence of 20 equiv of styrene at 80° C. for 7 days does not lead to thermodynamically favorable (E)-stilbene (FIG. 21B). It is worth noting that 10'-Ph is relatively thermally stable in solution. Thus, ~50% decomposition of 10'-Ph at 80° C. after 7 days was observed.

Figure 21C:
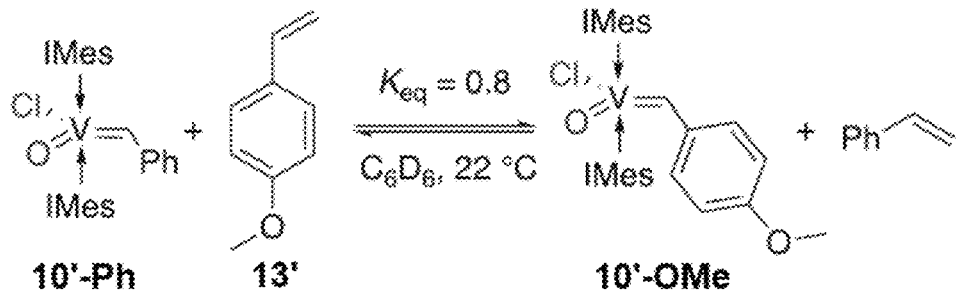
FIG. 21C shows reactivity of complex 10' in degenerate metathesis.

The addition of 4-MeO-styrene to 10'-Ph results in an equilibrium between 10'-Ph and 10'-OMe (FIG. 21C); the K$_{eq}$ value is 0.8 in C6D6 at 22° C. It is worth noting benzylidene 10'-OMe can be formed directly from 10' and 4-MeO-styrene 13'. The addition of styrene to 10'-OMe leads to the same equilibrium between 10'-Ph and 10'-OMe. The presence of electron-donating groups in the phenyl ring destabilizes the negative charge on the α-C atom, explaining the preference for 10'-Ph.

V oxo NHC complexes 10', 10'-Ph, and 10'-OMe are readily involved in cycloaddition/cycloreversion steps with styrenes. However, the absence of CM products indicates that degenerate metathesis is remarkably favorable for V oxo NHC species.

To investigate whether the formation of a 1,3-MCB is significantly more favorable than that of a 1,2-MCB for the studied systems, DFT (B3LYP-D3) studies were performed on the cross (via 1,2-MCB) and degenerate (via 1,3-MCB) metathesis of styrene and propene. Dissociation of one neutral ligand in 10'-Ph is required to form the active four-coordinate complex 10'-Ph-1 (FIG. 22). Cycloaddition between 10'-Ph-1 and styrene can lead to eight possible pathways depending on the relative position of the substituents. Similarly, the reactivity of the four-coordinated ethylidene 10'-Me-1 with propene follows equivalent pathways. The eight different pathways were computationally explored assuming the accepted OM reaction mechanism with d0 alkylidenes. The productive MCB has a trigonal-bipyramidal structure with apical oxo and chlorine ligands. The accuracy of the computational methodology was analyzed by reproducing the equilibrium constant between 10'-Ph and 10'-OMe. Calculations predict the thermodynamically favorable formation of 10'-Ph and 10'-OMe from 10'. Moreover, the reaction of 10'-Ph with 13' to form 10'-OMe is computed to be endergonic by 0.3 kcal mol-1. The computed equilibrium constant is thus 0.6, in excellent agreement with the experimentally determined value.

Figure 22A:
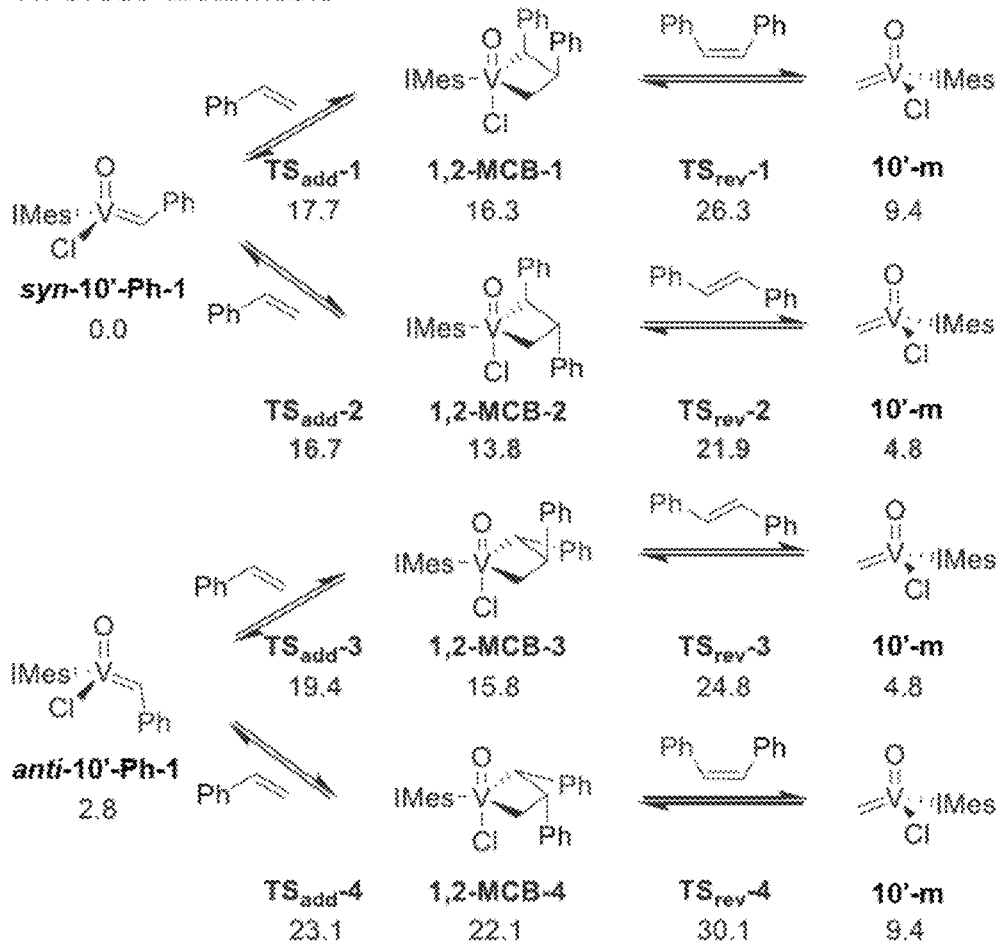
FIG. 22A shows calculated relative Gibbs free energies under benzene solvation (B3LYP-D3) in kcal/mol with respect to syn-10'-Ph-1 in cross-metathesis. Gray values show the most favorable paths via 1,2- and 1,3-MCBs.
Figure 22B:
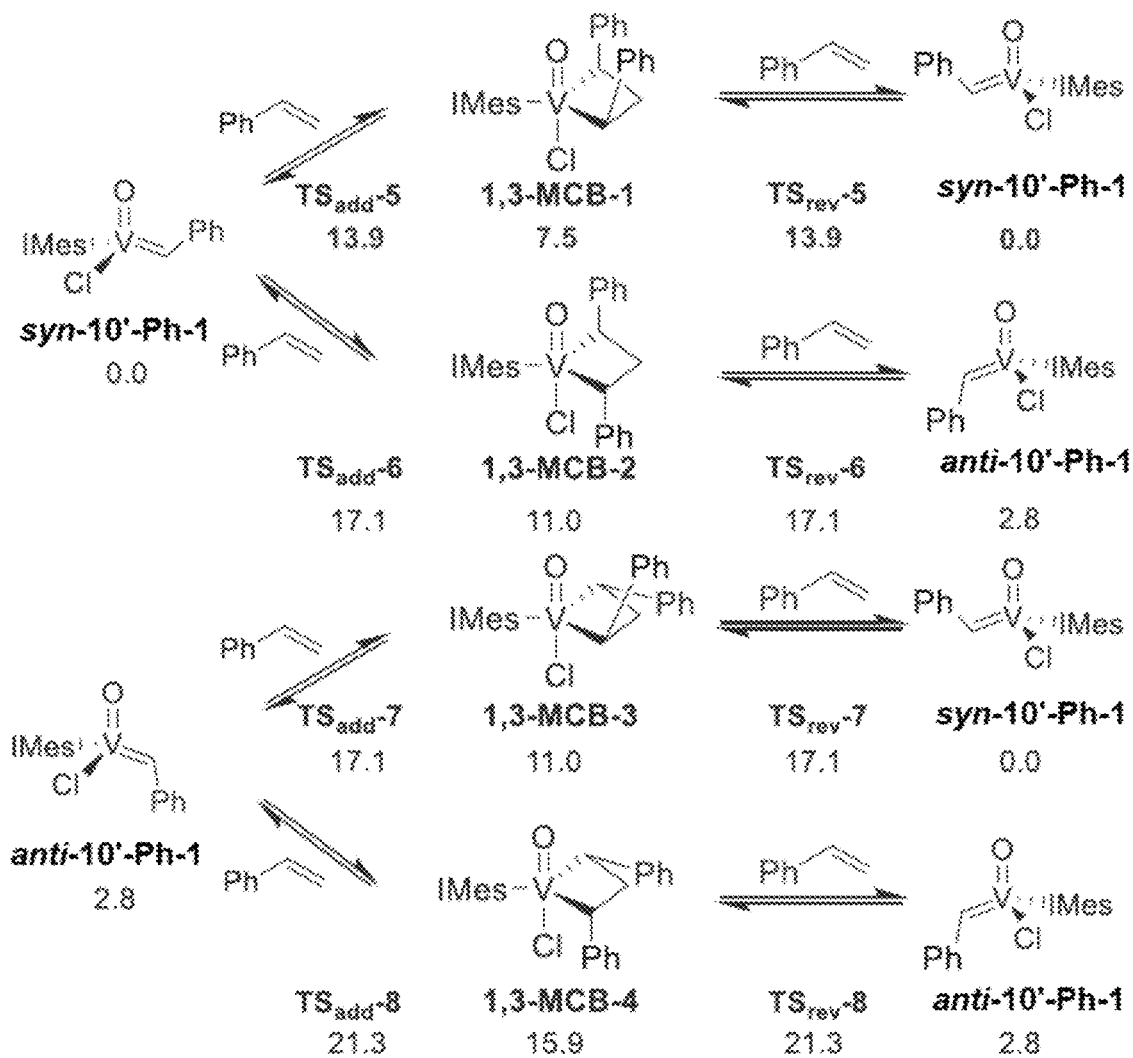
FIG. 22B shows calculated relative Gibbs free energies under benzene solvation (B3LYP-D3) in kcal/mol with respect to syn-10'-Ph-1 in degenerate metathesis. Gray values show the most favorable paths via 1,2- and 1,3-MCBs.

FIG. 22 shows the Gibbs energies of the eight pathways involved in the reaction of 10'-Ph-1 with styrene. syn-10'-Ph-1+styrene is used as the origin of energies. For the reaction of 10'-Ph-1 with styrene, calculations show that the preferred CM pathway is 1,2-MCB-2, which implies syn-10'-Ph-1 and trans-stilbene as the final product (FIG. 22A). The preferred degenerate pathway implies that the phenyls point toward the oxo ligand (1,3-MCB-1, FIG. 22B). The transition state for cyclo-reversion determines in both cases the feasibility of the two processes. This transition state is lower for the degenerate metathesis by 8.0 kcal mol-1, and this corresponds to a 10$^{-6}$ ratio between the corresponding kinetic constants (k$_{1,2}$/k$_{1,3}$). The reaction of 10'-Me-1 with propene presents lower energy barriers in general. The most favorable CM pathways involve 1,2-MCB-1 and 1,2-MCB-2, but they are still 4.1 and 4.3 kcal mol-1 higher in energy than the degenerate metathesis (10$^{-3}$ k$_{1,2}$/k$_{1,3}$ ratio). For comparison, reported data on Ru NHC alkylidenes have shown that 1,3-MCB is ~2 kcal/mol more favorable than 1,2-MCB. α-C atoms in V MCBs have a higher negative charge than those in Ru MCBs due to the lower V electronegativity. The higher polarization of the V=C bond favors that the substituted moiety of the reacting olefin interacts with the positively charged metal and, thus, overall 1,3-MCB.

To further support the high preference for degenerate metathesis, $^{13}$C-labeled 4-MeO-styrene (13'-$^{13}$C) was utilized for CIE with styrene in the presence of 3 mol % of 10' (Scheme 14). CIE is slow at room temperature. Heating the reaction mixture at 80° C. for 16 h led to 50% isotope exchange as expected under equilibrium conditions (assuming no isotope effect).

Scheme 14. Carbon Isotope Exchange Catalyzed by 10'.

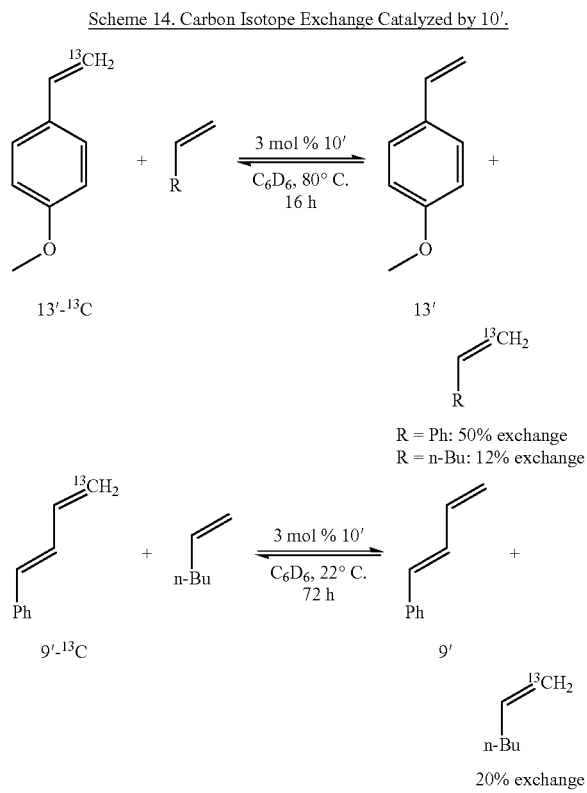

CIE involving alkyl olefins is less efficient. Thus, the reaction between 13'-$^{13}$C and 1-hexene led to 12% exchange after 16 h at 80° C. It is worth noting that only the formation of benzylidene from 4-MeO-styrene during the reaction by 1H NMR. This can be explained by the higher stabilization of a negative charge at the α-C atom by the aryl group in benzylidene than by the alkyl group in butylidene (alkylidene derived from 1-hexene). To overcome the bias in forming alkylidenes, CIE was performed between $^{13}$C-labeled 4-phenyl-1-butene (9'-$^{13}$C) and 1-hexene. However, the corresponding alkylidenes are not thermally stable. As a result, the reaction at elevated temperatures led to the catalyst's decomposition. CIE at room temperature resulted in 20% exchange after 72 h. CM products were not observed in any of the cases, confirming the preference for 1,3-MCBs for substrates containing alkyl groups.

V oxo NHC chloride complex 10' can be prepared from the corresponding phosphine complex by a ligand exchange reaction. The subsequent salt metathesis leads to the V oxo NHC alkoxide 11'. However, the bulky alkoxide ligand precludes the activity in olefin metathesis. Complex 10' is readily involved in cycloaddition/cycloreversion steps with terminal olefins. Unlike previously studied V oxo phosphine complexes and V imido NHC and phosphine complexes, the V oxo NHC chloride complex strongly prefers the formation of 1,3-MCB. This unusual reactivity can be applied to carbon isotope exchange reactions via degenerate metathesis.

The subject invention focuses on developing carbon isotope exchange methods via vanadium-catalyzed degenerate olefin metathesis involving terminal =CH$_2$ groups that can be applied to a diverse array of biologically active compounds for preclinical and clinical studies. The novel method eliminates tedious, time-consuming, and costly practices where the development of new multi-step synthetic strategies for each specific target molecule is required.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and that various modifications or changes in light thereof will be suggested to persons skilled in the art and are to be included within the spirit and purview of this application.

I claim:

1. A method for exchanging a carbon isotope (*C) in a compound comprising a terminal methyl group, the method comprising converting the terminal methyl group of the compound to a terminal =CH$_2$ moiety, exchanging the terminal =CH$_2$ moiety to a terminal =*CH$_2$ moiety in the presence of a *C-containing compound and a vanadium (V) complex catalyst, and optionally, converting the terminal =*CH$_2$ moiety to a terminal —*CH$_3$.

2. The method of claim 1, the conversion of terminal —CH$_3$ to =CH$_2$ occurring in the presence of a first catalyst with or without a hydrogen acceptor, the hydrogen acceptor being an olefin.

3. The method of claim 2, the first catalyst being an Ir- or Co-based catalyst.

4. The method of claim 1, the *C-containing compound being selected from *C-containing methylation reagents and *C-containing terminal olefins, the *C being $^{11}$C, $^{13}$C or $^{14}$C.

5. The method of claim 1, the conversion of the terminal =*CH$_2$ to the terminal —*CH$_3$ occurring in the presence of a hydrogen donor, and a second catalyst.

6. The method of claim 5, the second catalyst being an Ir-based catalyst or Pd/C.

7. The method of claim 1, the V complex catalyst having a general structure of formula (I):

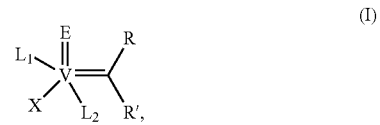

wherein E is O, NR" or S; L$_1$ and L$_2$ are each independently selected from phosphines, N-heterocyclic carbenes (NHC), pyridines, and nitriles, wherein one of L$_1$ and L$_2$ can be absent; X is selected from halogens, alkoxides, thioalkoxides, sulfonates, NCO, NCS, CN, NO$_3$, and pyrrolides; R and R' are each independently selected from hydrogen, alkyl, substituted alkyl, aryl, substituted aryl, heterocycles, substituted heterocycles, —OR$^a$, —Si(R$^b$)$_3$ and —NR$^c$R$^d$, wherein R$^a$, R$^b$, R$^c$ and R$^d$ are independently selected from hydrogen, alkyl, substituted alkyl, aryl, and substituted aryl; and R" is selected from hydrogen, alkyl, substituted alkyl, aryl, substituted aryl, heterocycles, and substituted heterocycles.

8. The method of claim 7, the V complex catalyst having a structure of (IV):

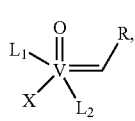
(IV)

wherein $L_1$ and $L_2$ are each independently selected from phosphines, NHC, pyridines, and nitriles, wherein one of $L_1$ and $L_2$ can be absent; X is selected from halogens, alkoxides, thioalkoxides, sulfonates, NCO, NCS, CN, $NO_3$, and pyrrolides; and R is selected from alkyl, substituted alkyl, aryl, substituted aryl, heterocycles, substituted heterocycles, $-OR^a$, $-Si(R^b)_3$ and $-NR^cR^d$, wherein $R^a$, $R^b$, $R^c$ and $R^d$ are independently selected from hydrogen, alkyl, substituted alkyl, aryl, and substituted aryl.

9. The method of claim 7, wherein $L_1$ and/or $L_2$ are phosphines having a general structure of $P(R_1)(R_2)(R_3)$, where $R_1$, $R_2$, and $R_3$ are each independently selected from hydrogen, alkyl, substituted alkyl, aryl and substituted aryl.

10. The method of claim 7, wherein $L_1$ and/or $L_2$ are NHCs selected from

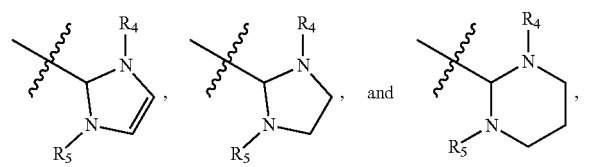

wherein $R_4$ and $R_5$ are independently selected from hydrogen, alkyl, substituted alkyl, cycloalkyl, substituted cycloalkyl, aryl, and substituted aryl.

11. The method of claim 7, wherein $L_1$ and/or $L_2$ are pyridines having a structure of

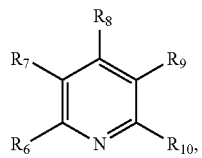

wherein $R_6$, $R_7$, $R_8$, $R_9$, $R_{10}$ are each independently selected from hydrogen, halogens, alkyl, substituted alkyl, hydorxyl, acyl, and $-NH_2$.

12. The method of claim 7, wherein $L_1$ and/or $L_2$ are nitriles selected from

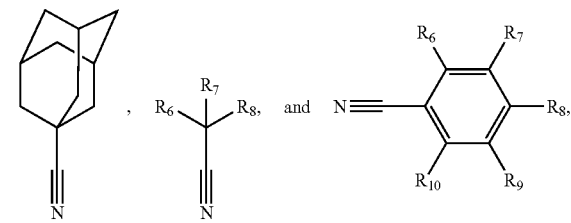

wherein $R_6$, $R_7$, $R_8$, $R_9$, $R_{10}$ are each independently selected from hydrogen, halogens, alkyl, substituted alkyl, hydorxyl, acyl, and $-NH_2$.

13. The method of claim 7, wherein X is selected from OAd, OPh, substituted OPh, $OSiPh_3$, substituted $OSiPh_3$, F, $OBu^tF_6$, $NO_3$, pyrroyl, substituted pyrroyl, SPh, substituted SPh, $OC_6F_5$, CN, NCO, NCS, Cl, Br, OTf, and I.

14. The method of claim 7, wherein $L_1$ and $L_2$ are phosphines; X is halogen; and R is $SiMe_3$ and R' is hydrogen.

15. The method of claim 7, the V complex catalyst being

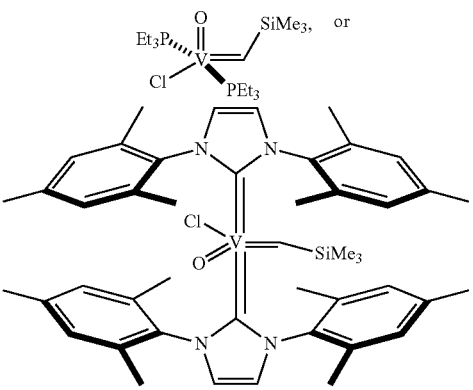

16. The method of claim 7, the V complex catalyst being selected from V imido phosphine catalysts, V imido NHC catalysts, V oxo phosphine catalysts and V oxo NHC catalysts.

17. The method of claim 1, further comprising reacting the compound comprising the terminal $=*CH_2$ with a molecule or functional group to form a compound having an internal *C.

18. A method for exchanging a carbon isotope (*C) in a compound having a terminal methyl group, the method comprising 1) contacting the compound having the terminal methyl group with a catalyst in the presence or absence of a hydrogen acceptor; 2) adding a V complex catalyst and a *C-containing compound to step 1); and optionally, adding a hydrogen donor to step 2).

19. The method of claim 18, the *C-containing compound being selected from *C-containing methylation reagents and *C-containing terminal olefins, the *C being $^{11}C$, $^{13}C$ or $^{14}C$.

20. The method of claim 1, the *C-containing compound being selected from *C-containing alkylation reagents and *C-containing terminal olefins.

* * * * *